US010640571B2

(12) United States Patent
Ho et al.

(10) Patent No.: US 10,640,571 B2
(45) Date of Patent: *May 5, 2020

(54) HUMAN MONOCLONAL ANTIBODIES SPECIFIC FOR GLYPICAN-3 AND USE THEREOF

(71) Applicant: The U.S.A., as represented by the Secretary, Department of Health and Human Services, Bethesda, MD (US)

(72) Inventors: Mitchell Ho, Urbana, MD (US); Mingqian Feng, Rockville, MD (US); Dimiter S. Dimitrov, Frederick, MD (US); Wei Gao, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 90 days.

This patent is subject to a terminal disclaimer.

(21) Appl. No.: 15/843,256

(22) Filed: Dec. 15, 2017

(65) Prior Publication Data

US 2018/0134800 A1    May 17, 2018

Related U.S. Application Data

(60) Continuation of application No. 15/090,873, filed on Apr. 5, 2016, now Pat. No. 9,932,406, which is a continuation of application No. 14/837,903, filed on Aug. 27, 2015, now Pat. No. 9,394,364, which is a division of application No. 14/111,860, filed as application No. PCT/US2012/034186 on Apr. 19, 2012, now Pat. No. 9,206,257.

(60) Provisional application No. 61/477,020, filed on Apr. 19, 2011.

(51) Int. Cl.
| | | |
|---|---|---|
| *C07K 16/30* | (2006.01) | |
| *A61K 47/68* | (2017.01) | |
| *A61K 39/395* | (2006.01) | |
| *G01N 33/68* | (2006.01) | |
| *C07K 16/28* | (2006.01) | |
| *G01N 33/574* | (2006.01) | |
| *C07K 14/21* | (2006.01) | |
| *A61K 39/00* | (2006.01) | |

(52) U.S. Cl.
CPC .... *C07K 16/3076* (2013.01); *A61K 39/39558* (2013.01); *A61K 47/6803* (2017.08); *A61K 47/6813* (2017.08); *A61K 47/6829* (2017.08); *A61K 47/6849* (2017.08); *A61K 47/6851* (2017.08); *C07K 14/21* (2013.01); *C07K 16/28* (2013.01); *C07K 16/303* (2013.01); *C07K 16/3092* (2013.01); *G01N 33/57438* (2013.01); *G01N 33/57492* (2013.01); *G01N 33/6893* (2013.01); *A61K 2039/505* (2013.01); *C07K 2317/21* (2013.01); *C07K 2317/31* (2013.01); *C07K 2317/33* (2013.01); *C07K 2317/41* (2013.01); *C07K 2317/56* (2013.01); *C07K 2317/565* (2013.01); *C07K 2317/569* (2013.01); *C07K 2317/622* (2013.01); *C07K 2317/73* (2013.01); *C07K 2317/92* (2013.01); *C07K 2319/00* (2013.01); *C07K 2319/33* (2013.01); *C07K 2319/55* (2013.01); *G01N 2333/705* (2013.01); *G01N 2400/40* (2013.01)

(58) Field of Classification Search
None
See application file for complete search history.

(56) References Cited

U.S. PATENT DOCUMENTS

| | | | |
|---|---|---|---|
| 6,881,557 B2 | 4/2005 | Foote | |
| 7,488,802 B2 | 2/2009 | Collins et al. | |
| 7,531,522 B2 | 5/2009 | Peschen et al. | |
| 2004/0137506 A1 | 7/2004 | Bates et al. | |
| 2007/0166308 A1 | 7/2007 | Pullen et al. | |
| 2008/0274123 A1 | 11/2008 | Wright et al. | |
| 2009/0117124 A1 | 5/2009 | Liu et al. | |

FOREIGN PATENT DOCUMENTS

| | | |
|---|---|---|
| EP | 1 674 111 A1 | 6/2006 |
| WO | WO 2009/012394 | 1/2009 |
| WO | WO 2009/032954 | 3/2009 |
| WO | WO 2011/032022 | 3/2011 |

OTHER PUBLICATIONS

Cartellieri et al., "Chimeric Antigen Receptor-Engineered T Cells for Immunotherapy of Cancer," *J. Biomed. Biotech.*, vol. 2010, 13 pages, 2010.

(Continued)

*Primary Examiner* — Nelson B Moseley, II
(74) *Attorney, Agent, or Firm* — Klarquist Sparkman, LLP

(57) ABSTRACT

Described herein is the identification of human monoclonal antibodies that bind GPC3 or heparan sulfate (HS) chains on GPC3 with high affinity. The antibodies described herein are capable of inhibiting HCC cell growth and migration. Provided are human monoclonal antibodies specific for GPC3 or HS chains on GPC3, including immunoglobulin molecules, such as IgG antibodies, as well as antibody fragments, such as single-domain VH antibodies or single chain variable fragments (scFv). Further provided are compositions including the antibodies that bind GPC3 or HS chains on GPC3, nucleic acid molecules encoding these antibodies, expression vectors comprising the nucleic acids, and isolated host cells that express the nucleic acids. Methods of treating cancer and/or inhibiting tumor growth or metastasis are also provided. Further provided are methods of detecting cancer in a subject and confirming a diagnosis of cancer in a subject.

21 Claims, 38 Drawing Sheets
Specification includes a Sequence Listing.

(56) References Cited

OTHER PUBLICATIONS

U.S. Appl. No. 14/111,860, Chen et al. "Construction of a Large Phage-Displayed Human Antibody Domain Library with a Scaffold Based on a Newly Identified Highly Soluble, Stable Heavy Chain Variable Domain," *J. Mol. Biol.*, vol. 382:779-789, 2008.
U.S. Appl. No. 14/111,860, GenBank Accession No. CAL05293, Immunoglobulin Heavy Chain Variable Region [*Homo sapiens*], submitted Jun. 7, 2006.
U.S. Appl. No. 14/111,860, GenBank Accession No. CAL05658, Immunoglobulin Heavy Chain Variable Region [*Homo sapiens*], submitted Jun. 7, 2006.
U.S. Appl. No. 15/090,873, Mack et al., "A Small Specific Antibody Construct Expressed as a Functional Single-Chain Molecule with High Tumor Cell Cytotoxicity," *Proc. Natl. Acad. Sci. USA*, vol. 92:7021-7025, 1995.
U.S. Appl. No. 14/111,860, Onda et al., "An Immunotoxin with Greatly Reduced Immunogenicity by Identification and Removal of B Cell Epitopes," *Proc. Natl. Acad. Sci. USA*, vol. 105:11311-11316, 2008.
U.S. Appl. No. 14/111,860, Park et al., "Adoptive Transfer of Chimeric Antigen Receptor Re-directed Cytolytic T Lymphocyte Clones in Patients with Neuroblastoma," *Mol. Ther.*, vol. 15(4):825-833, 2007.
U.S. Appl. No. 14/111,860, Takai et al., "Histopathological Analyses of the Antitumor Activity of Anti-Glypican-3 Antibody (GC33) in Human Liver Cancer Xenograft Models," *Cancer Bio. Ther.*, vol. 8:930-938, 2009.
U.S. Appl. No. 14/111,860, Weldon et al., "A Protease-Resistant Immunotoxin Against CD22 with Greatly Increased Activity Against CLL and Diminished Animal Toxicity," *Blood*, vol. 113: 3792-3800, 2009.

FIG. 2

```
                 *        20         *        40         *        60
HN3       : QVQLVQSGGGLVQPGGSLRLSCAASYFDFDSYEMSWVRQAPGKGLEWIGSIYHSG-STYYNPS :  62
s0        : QVQLVQSGGGLVQPGGSLRLSCAASGFSFSTYEMSWVRQAPGKGLEWVSPISGSGGNSYYADS :  63
DP47      : EVQLLESGGGLVQPGGSLRLSCAASGFTFSSYAMSWVRQAPGKGLEWVSAISGSGGSTYYADS :  63
HEL4      : EVQLLESGGGLVQPGGSLRLSCAASGFRISDEDMGWVRQAPGKGLEWVSSIYGPSGSTYYADS :  63
AAY33275  : QVQLVQSGGGLVQPGGSLRLSCAASGFTVSSNYMSWVRQAPGKGLEWVSVIYHGG-TTYYTDS :  62
AAS19424  : QVQLVQSGGGLIQPGGSLRLSCAASGFTVSSNYMSWVRQAPGKGLEWVSVIYSGG-STYYADS :  62
AFI12402  : EVQLVESGGGLVQPGGSLRLSCAASGFTFSTYAMSWVRQAPGKGLEWVASISTGG-STYYPDS :  62
AAW67367  : QVQLVQSGGGLVQPGGSLRLSCAASGFTFSSYAMSWVRQAPGKGLEWVSAISGSGGSTYYADS :  63
ACS95198  : EVQLVESGGGLVQPGGSLRLSCAASGFTFSSYEMNWVRQAPGKGLEWVSYISSSGSTIYYADS :  63

*        80         *       100         *       120
HN3       : LKSRVTISRDNSKNTLYLQMNTLRAEDTATYYCARVNMDR---------FDYWGQGTLVTVSS- : 117  SEQ ID NO:2
s0        : VKGRFTISRDNSKNTLYLQMNTLRAEDTAVYYCAKGPPVWSGYYFADGFDIWGQGTMVTVSS- : 125  SEQ ID NO:3
DP47      : VKGRFTISRDNSKNTLYLQMNSLRAEDTAVYYCAKSYGA---------FDYWGQGTLVTVSS- : 116  SEQ ID NO:4
HEL4      : VKGRFTISRDNSKNTLYLQMNSLRAEDTAVYYCASALEPLSEP-----LGFWGQGTLVTVSS- : 120  SEQ ID NO:5
AAY33275  : VKGRFTISRDNSKNTLYLQMNSLRAEDTAVYYCARANGA---------FDIWGQGTMVTVSS- : 115  SEQ ID NO:6
AAS19424  : VKGRFTISRDNSKNTLYLQMNSLRAEDTAVYYCARNFGED--------FDYWGQGTLVTVSS- : 116  SEQ ID NO:7
AFI12402  : VKGRFTISRDNAKNTLYLQMNSLRAEDTAVYYCARDYDGY--------FDYWGQGTLVTVSS- : 116  SEQ ID NO:8
AAW67367  : VKGRFTISRDNSKNTLYLQMNSLRAEDTAVYYCAKGITMIVVVISD-AFDIWGQGTMVTVSS- : 124  SEQ ID NO:9
ACS95198  : VKGRFTISRDNAKNSLYLQMNSLRAEDTAVYYCARENIAA--------FDYWGQGTLVTVSS- : 117  SEQ ID NO:10
```

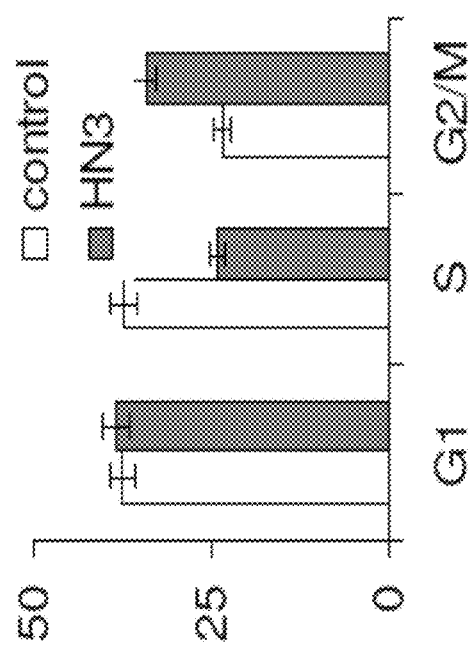
FIG. 7A

FIG. 10

```
HS20-VH     EVQLLESGGGLVQPGGSLRLSCAASGFTFSSYAMSWVRQAPGKGLEWVSTIQKQGIPIEY  60
ABQ50854.1  EVQLLESGGGLVQPGGSLRLSCAASGFTFSSYAMSWVRQAPGKGLEWVSSISRQISTRY  60
ADP21081.1  EVQLLESGGGLVQPGGSLRLSCAASGFTFSSYAMSWVRQAPGKGLEWVSTIRQGKATTY  60
            ************************************************:*:: * :

HS20-VH     ADSVKGRFTISRDNSKNTLYLQMNSLRAEDTAVYYCAKNRAKFDYWGQGTLVTVSS  116
ABQ50854.1  ADSVKGRFTISRDNSKNTLYLQMNSLRAEDTAVYYCAKGAGSEDYWGQGTLVTVSS  116
ADP21081.1  ADSVKGRFTISRDNSKNTLYLQMNSLRAEDTAVYYCAKGARVEDYWGQGTLVTVSS  116
            *************************************** .   :*********

HS20-VL     DIQMTQSPSSLSASVGDRVTITCRASQSISSYLNWYQQKPGKAPKLLIYNASMLQSGVPS  60
ABQ59019.1  DIQMTQSPSSLSASVGDRVTITCRASQSISSYLNWYQQKPGKAPKLLIYSASTLQSGVPS  60
ABQ50855.1  DIQMTQSPSSLSASVGDRVTITCRASQSISSYLNWYQQKPGKAPKLLIYKASSLQSGVPS  60
            ************************************************. *:*******

HS20-L      RFSGSGSGTDFTLTISSLQPEDFATYYCQQNRGPLITFGQGTKVEIK  107
ABQ59019.1  RFSGSGSGTDFTLTISSLQPEDFATYYCQQNSTYPATFGQGTKVEIK  107
ABQ50855.1  RFSGSGSGTDFTLTISSLQPEDFATYYCQQSRQFPSTFGQGTKVEIK  107
            ****************************** :  : :*********
```

Goat anti human kappa chain

FIG.15C

FIG. 18B
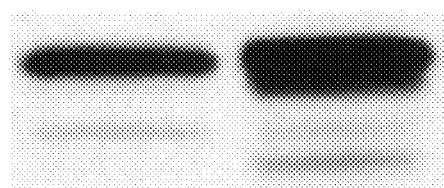 P-yap
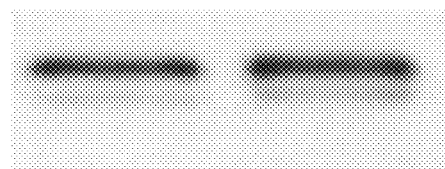 yap
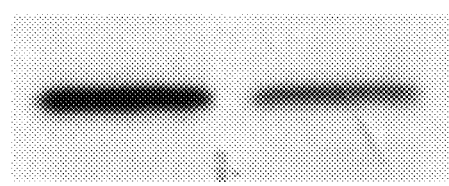 cyclin D1
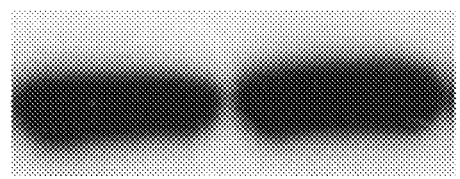 actin

SEQUENCE LISTING

```
<160> NUMBER OF SEQ ID NOS: 31

<210> SEQ ID NO 1
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 1
caggtgcagc tggtgcagtc tggggaggc ttggtacagc ctggagggtc cctgagactc      60
tcctgtgcag cctcttattt cgatttcgat tcttatgaaa tgagctgggt ccgccaggct    120
ccagggaagg gcctagagtg gattgggagt atctatcata gtgggagcac ctactacaac    180
ccgtccctca agagtcgagt caccatctcc agagacaatt ccaagaacac gctgtatctg    240
caaatgaaca ccctgagagc cgaggacaca gccacgtatt actgtgcgag agtaaatatg    300
gaccgatttg actactgggg ccagggaacc ctggtcaccg tctcctcaag t              351

<210> SEQ ID NO 2
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 2

Gln Val Gln Leu Val Gln Ser Gly Gly Gly Leu Val Gln Pro Gly Gly
 1               5                  10                  15

Ser Leu Arg Leu Ser Cys Ala Ala Ser Tyr Phe Asp Phe Asp Ser Tyr
            20                  25                  30

Glu Met Ser Trp Val Arg Gln Ala Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Val Asn Met Asp Arg Phe Asp Tyr Trp Gly Gln Gly Thr Leu Val
            100                 105                 110

Thr Val Ser Ser Ser
        115

<210> SEQ ID NO 3
<211> LENGTH: 125
```

```
<212> TYPE: PRT
<213> ORGANISM: Artificial Sequence
<220> FEATURE:
<223> OTHER INFORMATION: Synthetic polypeptide

<400> SEQUENCE: 3

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Ser Phe Ser Thr Tyr
            20                  25                  30

Glu Met Ser Trp Val Arg Gln Ala Pro Gly Lys Gly Leu Glu Trp Val
        35                  40                  45

Ser Pro Ile Ser Gly Ser Gly Asn Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Lys Gly Pro Pro Val Trp Ser Gly Tyr Tyr Phe Ala Asp Gly Phe
            100                 105                 110

Asp Ile Trp Gly Gln Gly Thr Met Val Thr Val Ser Ser
            115                 120                 125

<210> SEQ ID NO 4
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115

<210> SEQ ID NO 5
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Ile Ser Asp Glu
```

```
                    20                  25                  30
Asp Met Gly Trp Val Arg Gln Ala Pro Gly Lys Gly Leu Glu Trp Val
            35                  40                  45

Ser Ser Ile Tyr Gly Pro Ser Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Ala Leu Glu Pro Leu Ser Glu Pro Leu Gly Phe Trp Gly Gln
            100                 105                 110

Gly Thr Leu Val Thr Val Ser Ser
            115                 120

<210> SEQ ID NO 6
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 6

Gln Val Gln Leu Val Gln Ser Gly Gly Gly Leu Val Gln Pro Gly Gly
 1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Val Ile Tyr His Gly Gly Thr Thr Tyr Tyr Thr Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Ala Asn Gly Ala Phe Asp Ile Trp Gly Gln Gly Thr Met Val Thr
            100                 105                 110

Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 7

Gln Val Gln Leu Val Gln Ser Gly Gly Gly Leu Ile Gln Pro Gly Gly
 1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80
```

Gln Met Asn Ser Leu Arg Ala Glu Asp Thr Ala Val Tyr Tyr Cys Ala
                85                  90                  95

Arg Asn Phe Gly Glu Asp Phe Asp Tyr Trp Gly Gln Gly Thr Leu Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ala Ser Ile Ser Thr Gly Gly Ser Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Asp Gly Tyr Phe Asp Tyr Trp Gly Gln Gly Thr Leu Val
            100                 105                 110

Thr Val Ser Ser
        115

<210> SEQ ID NO 9
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 9

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ile Thr Met Ile Val Val Ile Ser Asp Ala Phe Asp
            100                 105                 110

Ile Trp Gly Gln Gly Thr Met Val Thr Val Ser Ser
        115                 120

<210> SEQ ID NO 10

<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Ile Ala Ala Phe Asp Tyr Trp Gly Gln Gly Thr Leu
            100                 105                 110

Val Thr Val Ser Ser
        115
```

<210> SEQ ID NO 11
<211> LENGTH: 717
<212> TYPE: DNA
<213> ORGANISM: Artificial Sequence
<220> FEATURE:
<223> OTHER INFORMATION: Synthetic polynucleotide

<400> SEQUENCE: 11

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaact attcagaagc agggtctgcc tacagagtac     180
gcagactccg tgaaggggcg gttcaccatc tccagagaca attccaagaa cacgctgtat     240
ctgcaaatga acagcctgag agccgaggac acggccgtat attactgtgc gaaaaatcgg     300
gctaagtttg actactgggg ccagggaacc ctggtcaccg tctcgagcgg tggaggcggt     360
tcaggcggag gtggcagcgg cggtggcggg tcgacggaca tccagatgac ccagtctcca     420 tcctcccctgt ctgcatctgt aggagacaga gtcaccatca cttgccgggc aagtcagagc     480
attagcagct atttaaattg gtatcagcag aaaccaggga agcccctaa gctcctgatc      540 tataatgcat ccatgttgca agtggggtc ccatcaaggt tcagtggcag tggatctggg     600
acagatttca ctctcaccat cagcagtctg caacctgaag attttgcaac ttactactgt     660
caacagaatc ggggttttcc tctgacgttc ggccaaggga ccaaggtgga aatcaaa       717
```

<210> SEQ ID NO 12
<211> LENGTH: 239
<212> TYPE: PRT
<213> ORGANISM: Artificial Sequence
<220> FEATURE:
<223> OTHER INFORMATION: Synthetic polypeptide

<400> SEQUENCE: 12

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Gln Lys Gln Gly Leu Pro Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Ala Lys Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Asn Ala Ser Met Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Asn Arg
    210                 215                 220

Gly Phe Pro Leu Thr Phe Gly Gln Gly Thr Lys Val Glu Ile Lys
225                 230                 235

<210> SEQ ID NO 13
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 13
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcaact attcagaagc agggtctgcc tacagagtac      180
gcagactccg tgaaggggcg gttcaccatc tccagagaca attccaagaa cacgctgtat    240
ctgcaaatga acagcctgag agccgaggac acggccgtat attactgtgc gaaaaatcgg    300
gctaagtttg actactgggg ccagggaacc ctggtcaccg tctcgagc                 348

<210> SEQ ID NO 14
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45

Ser Thr Ile Gln Lys Gln Gly Leu Pro Thr Glu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Arg Ala Lys Phe Asp Tyr Trp Gly Gln Gly Thr Leu Val
                100                 105                 110

Thr Val Ser Ser
        115

<210> SEQ ID NO 15
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 15
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctataat gcatccatgt tgcaaagtgg ggtcccatca    180
aggttcagtg gcagtggatc tgggacagat ttcactctca ccatcagcag tctgcaacct    240
gaagattttg caacttacta ctgtcaacag aatcggggtt ttcctctgac gttcggccaa    300
gggaccaagg tggaaatcaa a                                              321

<210> SEQ ID NO 16
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Asn Ala Ser Met Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Arg Gly Phe Pro Leu
                 85                  90                  95

Thr Phe Gly Gln Gly Thr Lys Val Glu Ile Lys
                100                 105

<210> SEQ ID NO 17
<211> LENGTH: 116
<212> TYPE: PRT
<213> ORGANISM: Artificial Sequence
<220> FEATURE:
<223> OTHER INFORMATION: Synthetic polypeptide
```

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gln Gly Thr Ser Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly Ser Phe Asp Tyr Trp Gly Gln Gly Thr Leu Val
            100                 105                 110

Thr Val Ser Ser
            115

<210> SEQ ID NO 18
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Arg Asp Gln Gly Leu His Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Arg Val Phe Asp Tyr Trp Gly Gln Gly Thr Leu Val
            100                 105                 110

Thr Val Ser Ser
            115

<210> SEQ ID NO 19
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ser Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Ser Tyr Pro Ala
                85                  90                  95

Thr Phe Gly Gln Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Lys Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Arg Gln Phe Pro Ser
                85                  90                  95

Thr Phe Gly Gln Gly Thr Lys Val Glu Ile Lys
            100                 105

<210> SEQ ID NO 21
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 21
cgacccgcca ccgccgctg                                             19

<210> SEQ ID NO 22
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 22
ctatgcggcc ccattca                                               17

<210> SEQ ID NO 23
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 23

Arg His Arg Gln Pro Arg Gly Trp Glu Gln Leu Pro Thr Gly Ala Glu
```

```
                 1               5                  10                 15
              Phe Leu Gly Asp Gly Gly Asp Val Ser Phe Ser Thr Arg Gly Thr Gln
                              20                  25                 30

Asn Trp Thr Val Glu Arg Leu Leu Gln Ala His Arg Gln Leu Glu Glu
                          35                  40                 45

Arg Gly Tyr Val Phe Val Gly Tyr His Gly Thr Phe Leu Glu Ala Ala
                      50                  55                 60

Gln Ser Ile Val Phe Gly Gly Val Arg Ala Arg Ser Gln Asp Leu Asp
              65                  70                  75                 80

Ala Ile Trp Arg Gly Phe Tyr Ile Ala Gly Asp Pro Ala Leu Ala Tyr
                              85                  90                 95

Gly Tyr Ala Gln Asp Gln Glu Pro Asp Ala Arg Gly Arg Ile Arg Asn
                          100                  105                110

Gly Ala Leu Leu Arg Val Tyr Val Pro Arg Ser Ser Leu Pro Gly Phe
                      115                  120                125

Tyr Arg Thr Ser Leu Thr Leu Ala Ala Pro Glu Ala Ala Gly Glu Val
                  130                  135                 140

Glu Arg Leu Ile Gly His Pro Leu Pro Leu Arg Leu Asp Ala Ile Thr
              145                  150                  155                160

Gly Pro Glu Glu Glu Gly Arg Leu Glu Thr Ile Leu Gly Trp Pro
                              165                  170                175

Leu Ala Glu Arg Thr Val Val Ile Pro Ser Ala Ile Pro Thr Asp Pro
                          180                  185                190

Arg Asn Val Gly Gly Asp Leu Asp Pro Ser Ser Ile Pro Asp Lys Glu
                      195                  200                205

Gln Ala Ile Ser Ala Leu Pro Asp Tyr Ala Ser Gln Pro Gly Lys Pro
                  210                  215                 220

Pro Arg Glu Asp Leu Lys
              225                  230

<210> SEQ ID NO 24
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 24

Arg His Arg Gln Pro Arg Gly Trp Glu Gln Leu Pro Thr Gly Ala Glu
              1               5                  10                 15

Phe Leu Gly Asp Gly Gly Asp Val Ser Phe Ser Thr Arg Gly Thr Gln
                              20                  25                 30

Asn Trp Thr Val Glu Arg Leu Leu Gln Ala His Arg Gln Leu Glu Glu
                          35                  40                 45

Gly Gly Tyr Val Phe Val Gly Tyr His Gly Thr Phe Leu Glu Ala Ala
                      50                  55                 60

Gln Ser Ile Val Phe Gly Gly Val Arg Ala Arg Ser Gln Asp Leu Asp
              65                  70                  75                 80

Ala Ile Trp Ala Gly Phe Tyr Ile Ala Gly Asp Pro Ala Leu Ala Tyr
                              85                  90                 95

Gly Tyr Ala Gln Asp Gln Glu Pro Asp Ala Ala Gly Arg Ile Arg Asn
                          100                  105                110

Gly Ala Leu Leu Arg Val Tyr Val Pro Arg Ser Ser Leu Pro Gly Phe
                      115                  120                125

Tyr Ala Thr Ser Leu Thr Leu Ala Ala Pro Glu Ala Ala Gly Glu Val
```

-continued

```
               130                 135                 140
Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
                180                 185                 190

Arg Asn Val Gly Gly Asp Leu Asp Pro Ser Ser Ile Pro Asp Ser Glu
                195                 200                 205

Gln Ala Ile Ser Ala Leu Pro Asp Tyr Ala Ser Gln Pro Gly Lys Pro
                210                 215                 220

Pro Arg Glu Asp Leu Lys
225                 230

<210> SEQ ID NO 25
<211> LENGTH: 230
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (23)..(23)
<223> OTHER INFORMATION: Xaa = Gly, Ala or Ser
<220> FEATURE:
<221> NAME/KEY: MISC_FEATURE
<222> LOCATION: (49)..(49)
<223> OTHER INFORMATION: Xaa = Gly, Ala or Ser
<220> FEATURE:
<221> NAME/KEY: MISC_FEATURE
<222> LOCATION: (84)..(84)
<223> OTHER INFORMATION: Xaa = Gly, Ala or Ser
<220> FEATURE:
<221> NAME/KEY: MISC_FEATURE
<222> LOCATION: (107)..(107)
<223> OTHER INFORMATION: Xaa = Gly, Ala or Ser
<220> FEATURE:
<221> NAME/KEY: MISC_FEATURE
<222> LOCATION: (130)..(130)
<223> OTHER INFORMATION: Xaa = Gly, Ala or Ser
<220> FEATURE:
<221> NAME/KEY: MISC_FEATURE
<222> LOCATION: (165)..(165)
<223> OTHER INFORMATION: Xaa = Gly, Ala or Ser
<220> FEATURE:
<221> NAME/KEY: MISC_FEATURE
<222> LOCATION: (207)..(207)
<223> OTHER INFORMATION: Xaa = Gly, Ala or Ser
<220> FEATURE:
<221> NAME/KEY: MISC_FEATURE
<222> LOCATION: (209)..(209)
<223> OTHER INFORMATION: Xaa = Gly, Ala or Ser

<400> SEQUENCE: 25

Arg His Arg Gln Pro Arg Gly Trp Glu Gln Leu Pro Thr Gly Ala Glu
1               5                   10                  15

Phe Leu Gly Asp Gly Gly Xaa Val Ser Phe Ser Thr Arg Gly Thr Gln
                20                  25                  30

Asn Trp Thr Val Glu Arg Leu Leu Gln Ala His Arg Gln Leu Glu Glu
                35                  40                  45

Xaa Gly Tyr Val Phe Val Gly Tyr His Gly Thr Phe Leu Glu Ala Ala
                50                  55                  60

Gln Ser Ile Val Phe Gly Gly Val Arg Ala Arg Ser Gln Asp Leu Asp
65                  70                  75                  80

Ala Ile Trp Xaa Gly Phe Tyr Ile Ala Gly Asp Pro Ala Leu Ala Tyr
                85                  90                  95
```

Gly Tyr Ala Gln Asp Gln Glu Pro Asp Ala Xaa Gly Arg Ile Arg Asn
            100                 105                 110

Gly Ala Leu Leu Arg Val Tyr Val Pro Arg Ser Ser Leu Pro Gly Phe
        115                 120                 125

Tyr Xaa Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Xaa Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Xaa Glu
        195                 200                 205

Xaa Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 26
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 26

Arg His Arg Gln Pro Arg Gly Trp Glu Gln Leu Pro Thr Gly Ala Glu
1               5                   10                  15

Phe Leu Gly Asp Gly Gly Ala Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Gly Gly Tyr Val Phe Val Gly Tyr His Gly Thr Phe Leu Glu Ala Ala
    50                  55                  60

Gln Ser Ile Val Phe Gly Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
        115                 120                 125

Tyr Ala Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
        195                 200                 205

Ala Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 27
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 27

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Asp Val Ser Phe Ser Thr Arg
        130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
        275                 280                 285

Gly Trp Pro Leu Ala Glu Arg Thr Val Val Ile Pro Ser Ala Ile Pro
    290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345

<210> SEQ ID NO 28
<211> LENGTH: 738
<212> TYPE: DNA
<213> ORGANISM: Artificial Sequence
<220> FEATURE:
<223> OTHER INFORMATION: Synthetic polynucleotide

<400> SEQUENCE: 28

```
caggtgcagc tggtgcagtc tggggaggc ttggtacagc ctggagggtc cctgagactc      60
tcctgtgcag cctcttattt cgatttcgat tcttatgaaa tgagctgggt ccgccaggct     120
ccagggaagg gcctagagtg gattgggagt atctatcata gtgggagcac ctactacaac     180
ccgtccctca agagtcgagt caccatctcc agagacaatt ccaagaacac gctgtatctg     240
caaatgaaca ccctgagagc cgaggacaca gccacgtatt actgtgcgag agtaaatatg     300
gaccgatttg actactgggg ccagggaacc ctggtcaccg tctcctcaag tgcggccaaa     360
gcttccggag gtcccgaggg cggcagcctg gccgcgctga ccgcgcacca ggcttgccac     420
ctgccgctgg agactttcac ccgtcatcgc cagccgcgcg gctgggaaca actggagcag     480
tgcggctatc cggtgcagcg gctggtcgcc ctctacctgg cggcgcggct gtcgtggaac     540
caggtcgacc aggtgatccg caacgccctg ccagccccg gcagcggcgg cgacctgggc     600
gaagcgatcc gcgagcagcc ggagcaagcc cgtctggccc tgaccctggc cgccgccgag     660
agcgagcgct tcgtccggca gggcaccggc aacgacgagg ccggcgcggc caacggcccg     720
gcggacagcg gcgacgcc                                                   738
```

<210> SEQ ID NO 29
<211> LENGTH: 247
<212> TYPE: PRT
<213> ORGANISM: Artificial Sequence
<220> FEATURE:
<223> OTHER INFORMATION: Synthetic polypeptide

<400> SEQUENCE: 29

```
Gln Val Gln Leu Val Gln Ser Gly Gly Gly Leu Val Gln Pro Gly Gly
1               5                   10                  15

Ser Leu Arg Leu Ser Cys Ala Ala Ser Tyr Phe Asp Phe Asp Ser Tyr
            20                  25                  30

Glu Met Ser Trp Val Arg Gln Ala Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Val Asn Met Asp Arg Phe Asp Tyr Trp Gly Gln Gly Thr Leu Val
            100                 105                 110

Thr Val Ser Ser Ala Ala Lys Ala Ser Gly Gly Pro Glu Gly Gly
        115                 120                 125

Ser Leu Ala Ala Leu Thr Ala His Gln Ala Cys His Leu Pro Leu Glu
    130                 135                 140

Thr Phe Thr Arg His Arg Gln Pro Arg Gly Trp Glu Gln Leu Glu Gln
145                 150                 155                 160

Cys Gly Tyr Pro Val Gln Arg Leu Val Ala Leu Tyr Leu Ala Ala Arg
                165                 170                 175
```

```
Leu Ser Trp Asn Gln Val Asp Gln Val Ile Arg Asn Ala Leu Ala Ser
            180                 185                 190

Pro Gly Ser Gly Gly Asp Leu Gly Glu Ala Ile Arg Glu Gln Pro Glu
            195                 200                 205

Gln Ala Arg Leu Ala Leu Thr Leu Ala Ala Ala Glu Ser Glu Arg Phe
    210                 215                 220

Val Arg Gln Gly Thr Gly Asn Asp Glu Ala Gly Ala Ala Asn Gly Pro
225                 230                 235                 240

Ala Asp Ser Gly Asp Ala Pro
                245

<210> SEQ ID NO 30
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 30
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccatgt tgcaaagtgg ggtcccatca     180
aggttcagtg gcagtggatc tgggacagat ttcactctca ccatcagcag tctgcaacct     240
gaagattttg caacttacta ctgtcaacag aatcggggtt ttcctctgac gttcggccaa     300
gggaccaagg tggaaatcaa a                                               321

<210> SEQ ID NO 31
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Met Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Arg Gly Phe Pro Leu
                85                  90                  95

Thr Phe Gly Gln Gly Thr Lys Val Glu Ile Lys
                100                 105
```

HUMAN MONOCLONAL ANTIBODIES SPECIFIC FOR GLYPICAN-3 AND USE THEREOF

CROSS REFERENCE TO RELATED APPLICATIONS

This is a continuation of U.S. application Ser. No. 15/090,873, filed Apr. 5, 2016, issue as U.S. Pat. No. 9,932,406 on Apr. 3, 2018, which is a continuation of U.S. patent application Ser. No. 14/837,903, filed Aug. 27, 2015, issued as U.S. Pat. No. 9,394,364 on Jul. 19, 2016, which is a divisional of U.S. patent application Ser. No. 14/111,860, filed Oct. 15, 2013, issued as U.S. Pat. No. 9,206,257 on Dec. 8, 2015, which is the U.S. National Stage of International Application No. PCT/US2012/034186, filed Apr. 19, 2012, which claims the benefit of U.S. Provisional Application No. 61/477,020, filed Apr. 19, 2011. The above-listed applications are herein incorporated by reference in their entirety.

ACKNOWLEDGMENT OF GOVERNMENT SUPPORT

This invention was made with government support under project number Z01 BC010891 awarded by the National Institutes of Health, National Cancer Institute. The government has certain rights in the invention.

FIELD

This disclosure concerns antibodies specific for glypican-3 (GPC3) or heparan sulfate on GPC3, and their use for the treatment of cancer.

BACKGROUND

Liver cancer is the fifth most prevalent neoplasm in the world and the third most common cause of cancer-related mortality (Bosch et al., *Gastroenterology* 127:S5-S16, 2004; El-Serag et al., *Gastroenterology* 132:2557-76, 2007). According to the American Cancer Society, hepatocellular carcinoma (HCC) accounts for about 75 percent of liver cancer cases. There are often no symptoms of liver cancer until the later stages. Surgery is the standard treatment for liver cancer as this type of cancer does not respond well to most chemotherapy drugs. Thus, there is an urgent need to develop new drugs with different mechanisms of action. Immunotherapy represents one new approach, but it remains a challenge primarily due to a lack of good tumor-specific targets.

The glypican family of heparan sulfate proteoglycans are anchored to the cell-surface via a covalent linkage to glycosylphosphatidylinositol (GPI). In vertebrates, six family members have been identified (GPC1-6). Glypican proteins are capable of modifying cell signaling pathways and contribute to cellular proliferation and tissue growth. Glypican-3 (GPC3) is highly expressed in HCC and some other human cancers including melanoma, squamous cell carcinomas of the lung, and clear cell carcinomas of the ovary, but is not expressed in normal tissues (Ho and Kim, *Eur J Cancer* 47(3):333-338, 2011). The GPC3 gene encodes a 70-kDa precursor core protein, which can be cleaved by furin to generate a 40-kDa amino (N) terminal fragment and a 30-kDa membrane-bound carboxyl (C) terminal fragment. The C terminus has two heparin sulfate (HS) glycan chains. The GPC3 protein is attached to the cell membrane by a glycosyl-phosphatidylinositol anchor. GPC3 binds Wnt and Hedgehog signaling proteins (Capurro et al., *Dev Cell* 14:700-711, 2008; Capurro et al., *Cancer Res* 65:6245-6254, 2005), and is also able to bind basic growth factors such as fibroblast growth factor 2 through its HS glycan chains (Song et al., *J Biol Chem* 272:7574-7577, 1997).

Loss-of-function mutations of GPC3 cause Simpson-Golabi-Behmel syndrome, a rare X-linked overgrowth disease (Pilia et al., *Nat Genet* 12: 241-247, 1996). GPC3-deficient mice have similar symptoms (Cano-Gauci et al., *J Cell Biol* 146: 255-264, 1999). In transgenic mice, over-expression of GPC3 suppresses hepatocyte proliferation and liver regeneration (Liu et al., *Hepatology* 52(3):1060-1067, 2010). In addition, Zittermann et al. recently showed that HCC cells infected with lentivirus expressing soluble GPC3 (sGPC3) have a lower cell proliferation rate (Zittermann et al., *Int J Cancer* 126:1291-1301, 2010). This finding may indicate that the sGPC3 protein secreted by infected cells inhibits cell proliferation in an autocrine manner. A recent study using recombinant sGPC3 (GPC3ΔGPI, amino acid residues Q25-H559) that lacks the GPI-anchoring domain in human HEK-293 cells provided direct evidence that sGPC3 protein can inhibit the growth of HCC in vitro (Feng et al., *Int J Cancer* 128(9):2246-2247, 2011). However, the precise biological functions of GPC3 and its role in tumorigenesis remain unknown.

HS proteoglycans (HSPGs) are key molecular effectors and have multiple functions in cancer and angiogenesis by their ability to interact with many important molecules. Most of the protein binding activity of HSPGs is due to the HS chains (Kim et al., *J Endocrinol* 209(2):139-151, 2011). The average HS chain is 50-200 repeating disaccharide units in length. Tumor metastasis is the leading cause of cancer-related death, but the molecular mechanisms underlying tumor metastasis remain poorly understood. It has been widely accepted that cancer metastasis is facilitated by the proteolytic activity of proteases such as matrix metalloproteinases. Recently, emerging evidence shows that cancer metastasis is also accompanied by the activities of the enzymes (e.g., heparanase) capable of cleaving HS side chains of HS proteoglycans (Arvatz et al., *Cancer Metastasis Rev* 30(2):253-268, 2011).

SUMMARY

Provided herein are human monoclonal antibodies that bind, for example specifically bind, GPC3 or HS chains on GPC3. The provided antibodies include immunoglobulin molecules, such as IgG antibodies, as well as antibody fragments, such as single-domain VH antibodies or single chain variable fragments (scFv). Further provided are compositions including the antibodies that bind, for example specifically, to GPC3 or HS chains on GPC3, nucleic acid molecules encoding these antibodies, expression vectors comprising the nucleic acid molecules, and isolated host cells that express the nucleic acid molecules. Also provided are immunoconjugates comprising the antibodies disclosed herein and an effector molecule, such as a toxin.

The antibodies and compositions provided herein can be used for a variety of purposes, such as for confirming the diagnosis of a cancer that expresses GPC3, for example HCC, in a subject. Thus, provided herein is a method of confirming the diagnosis of cancer in a subject by contacting a sample from the subject diagnosed with cancer with a human monoclonal antibody that binds GPC3 or HS chains on GPC3, and detecting binding of the antibody to the sample. An increase in binding of the antibody to the sample relative to binding of the antibody to a control sample confirms the cancer diagnosis. In some embodiments, the method further comprises contacting a second antibody that specifically recognizes the GPC3-specific antibody with the sample, and detecting binding of the second antibody.

Similarly, provided herein is a method of detecting a cancer that expresses GPC3, such as HCC, in a subject that includes contacting a sample from the subject with a human monoclonal antibody described herein, and detecting binding of the antibody to the sample. An increase in binding of the antibody to the sample relative to a control sample detects cancer in the subject. In some embodiments, the methods further comprise contacting a second antibody that specifically recognizes the GPC3-specific antibody with the sample, and detecting binding of the second antibody.

Further provided is a method of treating a subject with cancer, for example HCC, by selecting a subject with a cancer that expresses GPC3 and administering to the subject a therapeutically effective amount of a monoclonal antibody specific for GPC3 or HS chains on GPC3, or an immunoconjugate comprising the antibody.

In other embodiments, the cancer is treated or diagnosed by administering a monoclonal antibody that includes amino acid residues 26-33, 51-57 and 96-105 of SEQ ID NO: 2; or by administering a monoclonal antibody that includes amino acid residues 26-33, 51-58 and 97-105 of SEQ ID NO: 14 and residues 27-32, 50-52 and 89-97 of SEQ ID NO: 16 or SEQ ID NO: 31. In specific embodiments, a method is provided for inhibiting tumor growth or metastasis in a subject by selecting a subject with a cancer that expresses GPC3 and administering to the subject a therapeutically effective amount of the compositions disclosed herein.

The foregoing and other objects, features, and advantages of the invention will become more apparent from the following detailed description, which proceeds with reference to the accompanying figures.

BRIEF DESCRIPTION OF THE DRAWINGS

(FIG. 1A) SDS-PAGE of the wild type GPC3 protein and mutant GPC3 without the HS chains. (FIG. 1B) Western blot analysis. wt=wild-type sGPC3-hFc; mu=mutant sGPC3(AA)-hFc without HS chain.

FIG. 2 shows a sequence alignment of clone HN3 VH with known human VH from public databases (SEQ ID NOs: 2-10).

(FIG. 4A) ELISA assay using purified GPC3 proteins coated on 96-well plate. (FIG. 4B) Flow cytometry on the G1 cell line.

(FIG. 6A) Immunoblot analysis of GPC3 protein levels in Hep3B cell line 72 h after exposure to lentivirus-transfected GPC3-targeting shRNA or scrambled (scr) shRNA. Lentiviral GPC3-targeted shRNAs sh-1 and sh-2 efficiently inhibited GPC3 protein expression. (FIG. 6B) and (FIG. 6C) HCC cells treated with GPC3-shRNA or scrambled shRNA (scr) were evaluated by WST-8 assay. (FIG. 6D) Four HCC cell lines (Huh-7, Huh-4, Hep3B and A431) were treated with the HN3 human mAb or HN125 for 5 days. Cell proliferation was measured by WST-8 method. HN125 was used as an irrelevant hFc control.

FIGS. 7A-7D are a series of figures showing HN3 induced cell cycle arrest, apoptosis and inactivation of yap. (FIG. 7A) Cell cycle analysis. Cells were treated with HN3 or HN125 for 48 hours, cell cycle profiling was performed by FACS. p<0.05 compared to untreated cell (media). (FIG. 7B) Apoptosis analysis. Cells were treated with HN3 or IAB-hFc for 72 hours, followed by Annexin V/PI dual staining. p<0.05 compared to untreated cells. (FIG. 7C) HN3 induced PARP cleavage in Hep3B cells. Cells were incubated with HN3 or IAB-hFc for the indicated time. Lane1, HN3; Lane 2, HN125; Lane 3, media only. HN125 was used as an irrelevant hFc control. (FIG. 7D) Western blot showing inactivation of yap and down-regulation of cyclin D1 in HN3-treated HCC cells in vitro. Ctrl=HN125

(FIG. 9A) Output colonies were counted after each round of panning with $2 \times 10^{12}$ input phage. (FIG. 9B) Each phage clone was tested against different sources of GPC3s by ELISA (bars from left to right for each clone are GPC3, GPC3(NSO), rFc-GPC3, rFc-MSLN and BSA). rFc-MSLN (rabbit Fc control) and BSA were used as negative controls.

FIG. 10 shows an alignment of the amino acid sequence of selected scFvs and the HS20 variable heavy (SEQ ID NO: 14) and light (SEQ ID NO: 16) domains. CDRs are shaded. Shown are the sequences of ABQ50854.1 (a peptide mimotope of the group B Streptococcus type III polysaccharide; SEQ ID NO: 17); ADP21081.1 (canine dendritic cells; SEQ ID NO: 18); ABD59019.1 (TREM-like transcript-1; SEQ ID NO: 19) and ABQ50855.1 (a peptide mimotope of the group B Streptococcus type III polysaccharide; SEQ ID NO: 20). CDR regions were determined according to Kabat (underlined) and IMGT (shaded).

(FIG. 13A) The HS20 mAb was tested for its binding to GPC3-hFc, GPC3(AA)-hFc and GPC3 alone. 1G12 was used as a positive control. 1AB-hFc (the human Fc control) and BSA were used as negative controls. (FIG. 13B) Binding specificity of HS20 on GPC3 and HS alone. HS20 binds the GPC3 at least 1000-fold stronger than the HS alone. (FIG. 13C) Immunoprecipitation. G1 (A431.GPC3+) cells or Hep3B cells were lysed and pulled down by HS20 or isotype control and then detected by the mouse anti-GPC3 antibody (left). The arrow indicates the GPC3 core protein and the bracket indicates glycosylated GPC3. GPC3 knock-down cells were also examined by the same strategy (right). (FIG. 13D) Competition ELISA. The indicated concentration of heparan sulfate or heparin was pre-incubated with HS20 mAb (5 μg/ml). ELISA assay was then performed to detect HS20/GPC3 binding affinity.

FIGS. 14A-14E are a series of figures that show HS20 inhibited cell migration in HCC cells by disturbing the interaction between GPC3 and Wnt3a. (FIG. 14A) Hep3B cells and Huh-4 cells were treated with 100 μg/ml HS20 or isotype control. The images show the results of the wound healing assay using Hep3B (top) and Huh4 (bottom) cells. (FIG. 14B) Graphs showing a dose response (left) and time course (right) of wound healing assays on Hep3B cells. Data are represented as the percentage of open wound area, as mean±s.d. of three replicates (*$p<0.05$). (FIG. 14C) Hep3B cells were pretreated with 50 μg/ml IgG control or HS20 for 3 days and GPC3 was then immunoprecipitated with mouse anti-GPC3 antibody. The interaction between GPC3 and Wnt3a was detected. (FIG. 14D) Hep3B cells were pre-treated with 50 μg/ml IgG control or HS20 for 3 days and RT-PCR was performed to measure the RNA expression levels of the indicated Wnt-target genes. (FIG. 14E) Hep3B cells were pretreated with 50 μg/ml IgG control or HS20 for 3 days and then β-catenin expression was measured by Western blot.

FIG. 15C shows the HS20 $V_L$ sequence (SEQ ID NO: 16) in comparison with the $V_L$ of ABD59019.1 (TREM-like transcript-1; SEQ ID NO: 19) and ABQ50855.1 (a peptide mimotope of the group B *Streptococcus* type III polysaccharide; SEQ ID NO: 20). The HS20 mutant (Mt) was generated by mutating an asparagine (N) residue to an alanine (A) residue in CDR2 of the $V_L$ domain.

(FIG. 17A) 10 million HepG2 cells were implanted to nude mice by subcutaneous injection. When the tumor reached a volume of 100 mm³, mice were treated with 20 mg/kg HS20 by intravenous injection twice a week. Tumor volume (V) was quantified using the formula V=ab²/2 (where a and b represent tumor length and width, respectively). (FIG. 17B) Detection of the interaction between GPC3 and Wnt3A by co-IP assay with the tumor tissues. (FIG. 17C) RT-PCR to detect the downstream genes of Wnt signaling.

FIGS. 18A-18B show HN3 inhibits tumor growth in mice using Huh-7 cell as xenograft. (FIG. 18A) Graph showing the results using the HCC xenograft model in nude mice. Arrows indicate injection of HN3 (60 mg/kg). (FIG. 18B) Inactivation of yap and down-regulation of cyclin D1 in HN3-treated HCC tumors in mice. Ctrl: vehicle.

FIG. 19A is a schematic of the HN3(VH)-PE38 immunotoxin. To make an anti-GPC3 immunotoxin, the HN3 VH was fused to a truncated PE38.

SEQUENCE LISTING

Figure 1A:
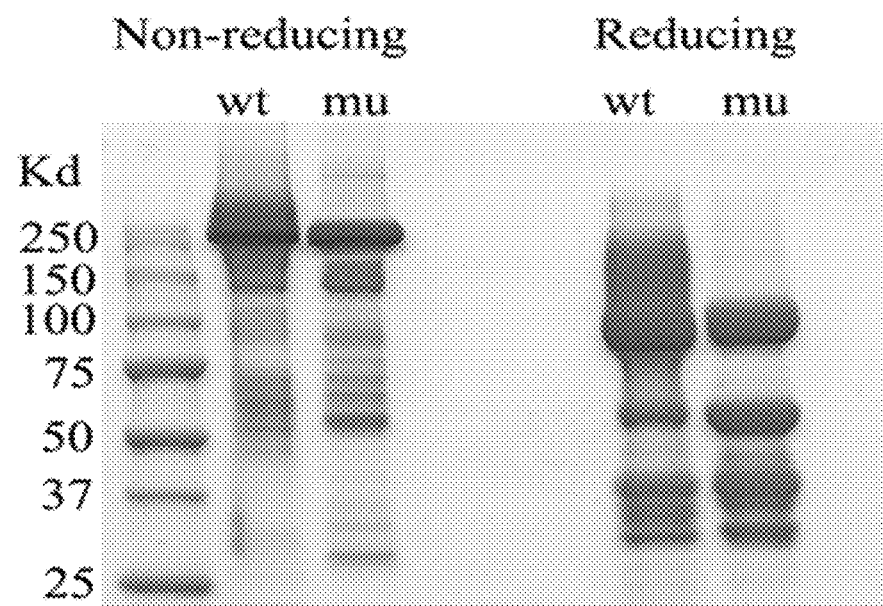
FIGS. 1A and 1B show production of recombinant GPC3 proteins.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Nov. 20, 2017, 38.5 KB, which is incorporated by reference herein. In the accompanying sequence listing:

SEQ ID NO: 1 is the nucleotide sequence of single domain (VH) antibody HN3.

SEQ ID NO: 2 is the amino acid sequence of single domain (VH) antibody HN3.

SEQ ID NOs: 3-10 are amino acid sequences of the VH domain of human antibodies.

SEQ ID NO: 11 is the nucleotide sequence of HS20 scFv.

SEQ ID NO: 12 is the amino acid sequence of HS20 scFv.

SEQ ID NO: 13 is the nucleotide sequence of the VH domain of HS20 (Wt).

SEQ ID NO: 14 is the amino acid sequence of the VH domain of HS20 (Wt).

SEQ ID NO: 15 is the nucleotide sequence of the VL domain of HS20 (Wt).

SEQ ID NO: 16 is the amino acid sequence of the VL domain of HS20 (Wt).

SEQ ID NO: 17 is the amino acid sequence of a VH domain that binds a peptide mimotope of the group B Streptococcus type III polysaccharide (GENBANK™ Accession No. ABQ50854.1).

SEQ ID NO: 18 is the amino acid sequence of a VH domain that binds canine dendritic cells (GENBANK™ Accession No. ADP21081.1).

SEQ ID NO: 19 is the amino acid sequence of the VL domain of an anti-TREM-like transcript-1 antibody (GENBANK™ Accession No. ABD59019.1).

SEQ ID NO: 20 is the amino acid sequence of a VL domain that binds a peptide mimotope of the group B Streptococcus type III polysaccharide (GENBANK™ Accession No. ABQ50855.1).

SEQ ID NOs: 21 and 22 are primer sequences.

SEQ ID NO: 23 is the amino acid sequence of PE-LR.

SEQ ID NO: 24 is the amino acid sequence of PE-LR/6x.

SEQ ID NO: 25 is the amino acid sequence of PE with reduced immunogenicity.

SEQ ID NO: 26 is the amino acid sequence of PE-LR/8M.

SEQ ID NO: 27 is the amino acid sequence of PE38.

SEQ ID NO: 28 is the nucleotide sequence of HN3-PE38.

SEQ ID NO: 29 is the amino acid sequence of HN3-PE38.

SEQ ID NO: 30 is the nucleotide sequence of the VL domain of HS20 Mt.

SEQ ID NO: 31 is the amino acid sequence of the VL domain of HS20 Mt.

DETAILED DESCRIPTION

I. Abbreviations

BSA bovine serum albumin
CDR complementarity determining region
cfu colony forming units
CTL cytotoxic T lymphocyte
ECM extracellular matrix
ELISA enzyme linked immunosorbent assay
FACS fluorescence activated cell sorting
GPC3 glypican-3
HCC hepatocellular carcinoma
hFc human Fc
HS heparin sulfate
HSPG heparan sulfate proteoglycan
Ig immunoglobulin
mAb monoclonal antibody
PBS phosphate buffered saline
PE Pseudomonas exotoxin
pfu plaque forming units
rFc rabbit Fc
sGPC3 soluble glypican-3

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A polypeptide ligand comprising at least a light chain or heavy chain immunoglobulin variable region which recognizes and binds (such as specifically recognizes and specifically binds) an epitope of an antigen, such as GPC3, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined according to Kabat et al. (see, Kabat et al., *Sequences of Proteins of Immunological Interest*, U.S. Department of Health and Human Services, 1991) and ImMunoGeneTics database (IMGT) (see, Lefranc, *Nucleic Acids Res* 29:207-9, 2001; and http://imgt.cines.fr/IMGT_vquest/vquest?livret=0&Option=humanIg). The Kabat database is maintained online (http://www.ncbi.nlm.nih.gov/igblast/). The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds GPC3, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds GPC3.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen (such as GPC3) is an antibody that binds the antigen with high affinity and does not significantly bind other unrelated antigens.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating liver cancer, such as HCC, or another tumor. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds GPC3 (or HS chain on GPC3) used in combination with a radioactive or chemical compound.

Conservative variants: "Conservative" amino acid substitutions are those substitutions that do not substantially affect or decrease the affinity of a protein, such as an antibody to GPC3. For example, a human antibody that specifically binds GPC3 can include at most about 1, at most about 2, at most about 5, and most about 10, or at most about 15 conservative substitutions and specifically bind the GPC3 polypeptide. The term conservative variation also includes the use of a substituted amino acid in place of an unsubstituted parent amino acid, provided that antibody specifically binds GPC3. Non-conservative substitutions are those that reduce an activity or binding to GPC3.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a GPC3 polypeptide or an antibody that binds GPC3 (or HS chains on GPC3) that includes a sequence that is degenerate as a result of the genetic code. There are 20 natural amino acids, most of which are specified by more than one codon. Therefore, all degenerate nucleotide sequences are included as long as the amino acid sequence of the GPC3 polypeptide or antibody that binds GPC3 encoded by the nucleotide sequence is unchanged.

Diagnostic: Identifying the presence or nature of a pathologic condition, such as, but not limited to, liver cancer, ovarian cancer, melanoma or lung cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as liver cancer or metastasis.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-GPC3 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as GPC3.

Framework region: Amino acid sequences interposed between CDRs. Framework regions include variable light and variable heavy framework regions. The framework regions serve to hold the CDRs in an appropriate orientation for antigen binding.

Glypican-3 (GPC3): A member of the glypican family of heparan sulfate (HS) proteoglycans that are attached to the cell surface by a glycosylphosphatidylinositol anchor (Filmus and Selleck, *J Clin Invest* 108:497-501, 2001). The GPC3 gene codes for a core protein of approximately 70 kD, which can be cleaved by furin to produce an N-terminal 40 kD fragment and a C-terminal 30 kD fragment. Two HS chains are attached on the C-terminal portion of GPC3. GPC3 and other glypican family proteins play a role in cell division and cell growth regulation. GPC3 is highly expressed in HCC and some other human cancers including melanoma, squamous cell carcinomas of the lung, and clear cell carcinomas of the ovary (Ho and Kim, *Eur J Cancer* 47(3):333-338, 2011), but is not expressed in normal tissues. GPC3 is also known as SGB, DGSX, MXR7, SDYS, SGBS, OCI-5, SGBS1 and GTR2-2.

There are four known isoforms of human GPC3 (isoforms 1-4). Nucleic acid and amino acid sequences of the four isoforms of GPC3 are known, including GENBANK™ Accession numbers: NM_001164617 and NP_001158089 (isoform 1); NM_004484 and NP_004475 (isoform 2); NM_001164618 and NP_001158090 (isoform 3); and NM_001164619 and NP_001158091 (isoform 4). In some embodiments of the present disclosure, the antibodies disclosed herein bind one or more of the four human GPC3 isoforms, or a conservative variant thereof.

HAMA (human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Heparan sulfate (HS): A member of the glycosaminoglycan family of carbohydrates that is very closely related in structure to heparin. HS is a linear polysaccharide found in all animal tissues. HS is found as a proteoglycan (PG) in which two or three HS chains are attached in close proximity to cell surface or extracellular matrix proteins. It is in this form that HS binds to a variety of protein ligands and regulates a wide variety of biological activities, including developmental processes, angiogenesis, blood coagulation and tumor metastasis.

Hepatocellular carcinoma (HCC): A primary malignancy of the liver typically occurring in patients with inflammatory livers resulting from viral hepatitis, liver toxins or hepatic cirrhosis (often caused by alcoholism). HCC is also called malignant hepatoma.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4$^+$ response or a CD8$^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Melanoma: A form of cancer that originates in melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma and uveal melanoma.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, a tumor is a liver cancer, such HCC or hepatoblastoma, melanoma, a squamous cell carcinoma, such as squamous cell carcinoma of the lung, a clear cell carcinoma, such as clear cell carcinoma of the ovary, thyroid cancer, Wilms' tumor, neuroblastoma, or a testicular germ cell tumor.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E.W. Martin, Mack Publishing Co., Easton, Pa., 15th Edition, 1975, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter). Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which GPC3 is expressed.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a HCC tissue biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a GPC3 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Squamous cell carcinoma: A type of cancer that originates in squamous cells, thin, flat cells that form the surface of the skin, eyes, various internal organs, and the lining of hollow organs and ducts of some glands. Squamous cell carcinoma is also referred to as epidermoid carcinoma. One type of squamous cell carcinoma is squamous cell carcinoma of the lung.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GENBANK™ Accession numbers are herein incorporated by reference as they appear in the database on Apr. 14, 2011. In case of conflict, the present specification, including explanations of terms, will control. In addition, the materials, methods, and examples are illustrative only and not intended to be limiting.

III. Introduction

The present disclosure describes the identification of monoclonal antibodies that bind a GPC, such as GPC3 or heparan sulfate (HS) chains on GPC3. Particular embodiments disclose the isolation and characterization of a single-domain VH human mAb (named HN3) targeting human GPC3. Particular data disclosed herein demonstrate that HN3 binds cell surface-associated GPC3 with high affinity. It is further shown that HN3 binds a conformation-sensitive epitope in the core protein of GPC3. HN3 inhibits HCC cell growth in vitro and in vivo, providing evidence that a GPC3 binder can directly inhibit HCC cell proliferation.

Further disclosed herein is the generation and characterization of a human mAb (named HS20) specific for the HS chains on GPC3. The HS20 single-chain variable fragment (scFv) was isolated by phage display and converted into a human IgG molecule. HS20 bound GPC3, but not a mutant form GPC3 lacking the HS chains, indicating the epitope of HS20 is located on the HS chain. Immunohistochemistry analysis showed strong immunostaining on the cell membrane of HCC cells and no staining on non-cancer cells such as stroma cells. Moreover, results of wound healing assays disclosed herein demonstrate that HS20 inhibits HCC cell migration, and xenograft studies demonstrate that HS20 inhibits HCC tumor growth in vivo.

IV. Human Monoclonal Antibodies that Bind GPC3 or HS Chains on GPC3

Disclosed herein are human monoclonal antibodies that bind (for example, specifically bind) the GPC3 core protein, or HS chains on GPC3. In some embodiments, the human monoclonal antibody is an antibody fragment, such as a single domain antibody, for example a VH domain. In other embodiments, the antibody functional fragment is a scFv. In other embodiments, the antibody is an immunoglobulin molecule, such as IgG.

A. HN3—Single (VH) Domain Monoclonal Antibody Specific for GPC3

In some embodiments of the present disclosure, the human monoclonal antibody specific for GPC3 is a single domain (VH) antibody referred to as HN3. The DNA and protein sequences for HN3 are shown below and are set forth in the sequence listing as SEQ ID NO: 1 and SEQ ID NO: 2, respectively. Tables 1A and 1B lists the nucleotide and amino acid positions of the HN3 CDRs, as determined by Kabat (Table 1A) and IMGT (Table 1B).

HN3 DNA Sequence
(SEQ ID NO: 1)
CAGGTGCAGCTGGTGCAGTCTGGGGGAGGCTTGGTACAGCCTGGAGGGTC

CCTGAGACTCTCCTGTGCAGCCTCTTATTTCGATTTCGATTCTTATGAAA

TGAGCTGGGTCCGCCAGGCTCCAGGGAAGGGCCTAGAGTGGATTGGGAGT

ATCTATCATAGTGGGAGCACCTACTACAACCCGTCCCTCAAGAGTCGAGT

CACCATCTCCAGAGACAATTCCAAGAACACGCTGTATCTGCAAATGAACA

CCCTGAGAGCCGAGGACACAGCCACGTATTACTGTGCGAGAGTAAATATG

GACCGATTTGACTACTGGGGCCAGGGAACCCTGGTCACCGTCTCCTCAAG

T

HN3 Protein Sequence
(SEQ ID NO: 2)
QVQLVQSGGGLVQPGGSLRLSCAASYFDFDSYEMSWVRQAPGKGLEWIGS

IYHSGSTYYNPSLKSRVTISRDNSKNTLYLQMNTLRAEDTATYYCARVNM

DRFDYWGQGTLVTVSSS

TABLE 1A

Locations of the CDRs in the HN3 Sequence (according to Kabat)

| CDR | DNA Sequence (SEQ ID NO: 1) | Protein Sequence (SEQ ID NO: 2) |
|---|---|---|
| CDR1 | nucleotides 91-105 | amino acids 31-35 |
| CDR2 | nucleotides 148-195 | amino acids 50-65 |
| CDR3 | nucleotides 286-315 | amino acids 96-105 |

TABLE 1B

Locations of the CDRs in the HN3 Sequence (according to IMGT)

| CDR | DNA Sequence (SEQ ID NO: 1) | Protein Sequence (SEQ ID NO: 2) |
|---|---|---|
| CDR1 | nucleotides 76-99 | amino acids 26-33 |
| CDR2 | nucleotides 151-171 | amino acids 51-57 |
| CDR3 | nucleotides 286-315 | amino acids 96-105 |

Provided herein are isolated human monoclonal antibodies that bind (for example, specifically bind) GPC3, wherein the heavy chain of the antibody comprises at least a portion of the amino acid sequence set forth herein at SEQ ID NO: 2 (the amino acid sequence of VH domain antibody HN3), such as one or more CDRs of SEQ ID NO: 2. In some embodiments, the antibodies comprise one or more (such as all three) CDR sequences from SEQ ID NO: 2 as determined using the Kabat method. In other embodiments, the antibodies comprise one or more (such as all three) CDR sequences from SEQ ID NO: 2 as determined by IMGT.

In some embodiments, the heavy chain of the human monoclonal antibody that binds, for example specifically binds, GPC3 comprises amino acid residues 31-35 of SEQ ID NO: 2, amino acid residues 50-65 of SEQ ID NO: 2, amino acid residues 96-105 of SEQ ID NO: 2, or any combination thereof. In some examples, the heavy chain of the human monoclonal antibody comprises amino acid residues 31-35, 50-65 and 96-105 of SEQ ID NO: 2.

In some embodiments, the heavy chain of the human monoclonal antibody that specifically binds GPC3 comprises amino acid residues 26-33 of SEQ ID NO: 2, amino acid residues 51-57 of SEQ ID NO: 2, or amino acid residues 96-105 of SEQ ID NO: 2, or any combination thereof. In some examples, the heavy chain of the human monoclonal antibody comprises amino acid residues 26-33, 51-57 and 96-105 of SEQ ID NO: 2.

In particular non-limiting examples, the heavy chain of the antibody comprises the amino acid sequence of SEQ ID NO: 2.

In some embodiments, the human monoclonal antibody is a VH single-domain antibody, a Fab fragment, a Fab' fragment, a F(ab)'2 fragment, a single chain variable fragment (scFv), or a disulfide stabilized variable fragment (dsFv). In one non-limiting example, the antibody is a VH single-domain antibody. In other examples, the antibody is a scFv or an IgG.

In some embodiments, the disclosed antibodies bind GPC3 (recombinant protein or cell-surface GPC3) with a dissociation constant ($K_d$) of about 2 nM or less. In several embodiments, the human monoclonal antibodies bind GPC3 with a binding affinity of about 2 nM, about 1 nM, about 0.7 nM, about 0.6 nM, about 0.5 nM, about 0.4 nM, about 0.3 nM, about 0.2 nM, about 0.15 nM or about 0.1 nM.

The isolated human monoclonal antibodies disclosed herein can be labeled, such as with a fluorescent, enzymatic, or radioactive label.

Further provided herein are compositions comprising a therapeutically effective amount of the disclosed antibodies and a pharmaceutically acceptable carrier.

Immunoconjugates comprising the human monoclonal antibodies disclosed herein and an effector molecule are also provided. The effector molecule can be, for example, a toxin or a detectable label. In some examples, the immunoconjugate comprises HN3 fused to a toxin, such as a *Pseudomonas* exotoxin or variant thereof, for example PE38. In particular examples, the immunoconjugate comprises an amino acid sequence at least 85%, at least 90%, at least 95%, at least 96%, at least 97%, at least 98% or at least 99% identical to SEQ ID NO: 29. In one non-limiting example, the amino acid sequence of the immunoconjugate comprises or consists of SEQ ID NO: 29. Examples of immunoconjugates are discussed in greater detail in section V below. Also provided are compositions comprising a therapeutically effective amount of the immunoconjugates disclosed herein and a pharmaceutically acceptable carrier.

Further provided herein are isolated nucleic acid molecules encoding the disclosed human monoclonal antibodies. In some embodiments, the nucleotide sequence encoding the heavy chain of the human monoclonal antibody comprises at least a portion of SEQ ID NO: 1, such as the portion encoding one or more CDRs of SEQ ID NO: 1. In some examples, the heavy chain of the human monoclonal antibody comprises the nucleic acid sequence of SEQ ID NO: 1. In some examples, the isolated nucleic acid molecule is operably linked to a promoter.

Also provided are expression vectors comprising the isolated nucleic acid molecules disclosed herein. Isolated host cells comprising the nucleic acid molecules or vectors are also provided herein. In some examples, the host cell is a T cell, such as a cytotoxic T lymphocyte (CTL).

B. HS20—Monoclonal Antibody Specific for HS Chains on GPC3

In some embodiments of the present disclosure, the human monoclonal antibody specific for HS chains on GPC3 comprises a scFv antibody referred to as H520. The DNA and protein sequences for HS20 scFv are shown below and are set forth in the sequence listing as SEQ ID NO: 11 and SEQ ID NO: 12, respectively. The VH and VL sequences for the wild-type (Wt) and mutated (Mt) versions of HS20 are also designated below. Tables 2A-2B and 3A-3B list the nucleotide and amino acid positions of the HS20 CDRs, as determined by Kabat (Tables 2A and 3A) and IMGT (Tables 2B and 3B).

```
HS20 scFv DNA sequence (SEQ ID NO: 11):
GAGGTGCAGCTGTTGGAGTCTGGGGGAGGCTTGGTACAGCCTGGGGGGTCCCTGAGAC

TCTCCTGTGCAGCCTCTGGATTCACCTTTAGCAGCTATGCCATGAGCTGGGTCCGCCAG

GCTCCAGGGAAGGGGCTGGAGTGGGTCTCAACTATTCAGAAGCAGGGTCTGCCTACAgA

GTACGCAGACTCCGTGAAGGGGCGGTTCACCATCTCCAGAGACAATTCCAAGAACACG

CTGTATCTGCAAATGAACAGCCTGAGAGCCGAGGACACGGCCGTATATTACTGTGCGAA

AAATCGGGCTAAGTTTGACTACTGGGGCCAGGGAACCCTGGTCACCGTCTCGAGCGGTG

GAGGCGGTTCAGGCGGAGGTGGCAGCGGCGGTGGCGGGTCGACGGACATCcAGATGAC

CCAGTCTCCATCCTCCCTGTCTGCATCTGTAGGAGACAGAGTCACCATCACTTGCCGGG

CAAGTCAGAGCATTAGCAGCTATTTAAATTGGTATCAGCAGAAACCAGGGAAAGCCCC

TAAGCTCCTGATCTATAATGCATCCATGTTGCAAAGTGGGGTCCCATCAAGGTTCAGTG

GCAGTGGATCTGGGACAGATTTCACTCTCACCATCAGCAGTCTGCAACCTGAAGATTTT

GCAACTTACTACTGTCAACAGAATCGGGGTTTTCCTCTGACGTTCGGCCAAGGGACCAA

GGTGGAAATCAAA

HS20 scFv Protein Sequence (SEQ ID NO: 12):
EVQLLESGGGLVQPGGSLRLSCAASGFTFSSYAMSWVRQAPGKGLEWVSTIQKQGLPTEYA

DSVKGRFTISRDNSKNTLYLQMNSLRAEDTAVYYCAKNRAKFDYWGQGTLVTVSSGGGGS

GGGGSGGGGSTDIQMTQSPSSLSASVGDRVTITCRASQSISSYLNWYQQKPGKAPKLLIYNA

SMLQSGVPSRFSGSGSGTDFTLTISSLQPEDFATYYCQQNRGFPLTFGQGTKVEIK

HS20 (Wt) VH and VL DNA Sequences
VH (SEQ ID NO: 13):
GAGGTGCAGCTGTTGGAGTCTGGGGGAGGCTTGGTACAGCCTGGGGGGTCCCTGAGAC

TCTCCTGTGCAGCCTCTGGATTCACCTTTAGCAGCTATGCCATGAGCTGGGTCCGCCAG

GCTCCAGGGAAGGGGCTGGAGTGGGTCTCAACTATTCAGAAGCAGGGTCTGCCTACAC

AGTACGCAGACTCCGTGAAGGGGCGGTTCACCATCTCCAGAGACAATTCCAAGAACAC

GCTGTATCTGCAAATGAACAGCCTGAGAGCCGAGGACACGGCCGTATATTACTGTGCGA

AAAATCGGGCTAAGTTTGACTACTGGGGCCAGGGAACCCTGGTCACCGTCTCGAGC

VL (SEQ ID NO: 15):
GACATCCAGATGACCCAGTCTCCATCCTCCCTGTCTGCATCTGTAGGAGACAGAGTCAC

CATCACTTGCCGGGCAAGTCAGAGCATTAGCAGCTATTTAAATTGGTATCAGCAGAAAC

CAGGGAAAGCCCCTAAGCTCCTGATCTATAATGCATCCATGTTGCAAAGTGGGGTCCCA

TCAAGGTTCAGTGGCAGTGGATCTGGGACAGATTTCACTCTCACCATCAGCAGTCTGCA

ACCTGAAGATTTTGCAACTTACTACTGTCAACAGAATCGGGGTTTTCCTCTGACGTTCGG

CCAAGGGACCAAGGTGGAAATCAAA

H520 (Wt) VH and VL Protein Sequences
VH (SEQ ID NO: 14):
EVQLLESGGGLVQPGGSLRLSCAASGFTFSSYAMSWVRQAPGKGLEWVSTIQKQGLPTQY

ADSVKGRFTISRDNSKNTLYLQMNSLRAEDTAVYYCAKNRAKFDYWGQGTLVTVSS
```

VL (SEQ ID NO: 16):
DIQMTQSPSSLSASVGDRVTITCRASQSISSYLNWYQQKPGKAPKLLIYNASMLQSGVPSRFS

GSGSGTDFTLTISSLQPEDFATYYCQQNRGFPLTFGQGTKVEIK

As described below in Example 3, a modified version of the HS20
mAb (referred to as HS20 Mt) was generated to remove an
N-glycosylation site in the VL domain. The nucleotide and amino
acid sequences of the VL domain of HS20 Mt are shown below.
The mutated nucleotides and amino acid residue are underlined.
H520 MtVL-nucleotide sequence (SEQ ID NO: 30)
GACATCcAGATGACCCAGTCTCCATCCTCCCTGTCTGCATCTGTAGGAGACAGAGTCAC

CATCACTTGCCGGGCAAGTCAGAGCATTAGCAGCTATTTAAATTGGTATCAGCAGAAAC

CAGGGAAAGCCCCTAAGCTCCTGATCTATGCTGCATCCATGTTGCAAAGTGGGGTCCCA

TCAAGGTTCAGTGGCAGTGGATCTGGGACAGATTTCACTCTCACCATCAGCAGTCTGCA

ACCTGAAGATTTTGCAACTTACTACTGTCAACAGAATCGGGGTTTTCCTCTGACGTTCGG

CCAAGGGACCAAGGTGGAAATCAAA

H520 Mt VL-amino acid sequence (SEQ ID NO: 31)
DIQMTQSPSSLSASVGDRVTITCRASQSISSYLNWYQQKPGKAPKLLIYAASMLQSGVPSRFS

GSGSGTDFTLTISSLQPEDFATYYCQQNRGFPLTFGQGTKVEIK

TABLE 2A

Locations of the CDRs in the HS20 VH Sequence (according to Kabat)

| CDR | DNA Sequence (SEQ ID NO: 13) | Protein Sequence (SEQ ID NO: 14) |
| --- | --- | --- |
| CDR1 | nucleotides 91-105 | amino acids 31-35 |
| CDR2 | nucleotides 148-198 | amino acids 50-66 |
| CDR3 | nucleotides 289-315 | amino acids 97-105 |

TABLE 2B

Locations of the CDRs in the HS20 VH Sequence (according to IMGT)

| CDR | DNA Sequence (SEQ ID NO: 13) | Protein Sequence (SEQ ID NO: 14) |
| --- | --- | --- |
| CDR1 | nucleotides 76-99 | amino acids 26-33 |
| CDR2 | nucleotides 151-174 | amino acids 51-58 |
| CDR3 | nucleotides 289-315 | amino acids 97-105 |

TABLE 3A

Locations of the CDRs in the HS20 VL Sequence (according to Kabat)

| CDR | DNA Sequence (SEQ ID NO: 15 or SEQ ID NO: 30) | Protein Sequence (SEQ ID NO: 16 or SEQ ID NO: 31) |
| --- | --- | --- |
| CDR1 | nucleotides 70-102 | amino acids 24-34 |
| CDR2 | nucleotides 148-168 | amino acids 50-56 |
| CDR3 | nucleotides 265-291 | amino acids 89-97 |

TABLE 3B

Locations of the CDRs in the HS20 VL Sequence (according to IMGT)

| CDR | DNA Sequence (SEQ ID NO: 15 or SEQ ID NO: 30) | Protein Sequence (SEQ ID NO: 16 or SEQ ID NO: 31) |
| --- | --- | --- |
| CDR1 | nucleotides 79-96 | amino acids 27-32 |
| CDR2 | nucleotides 148-156 | amino acids 50-52 |
| CDR3 | nucleotides 265-291 | amino acids 89-97 |

Provided herein are isolated human monoclonal antibodies that bind (for example, specifically bind) HS chains on GPC3, wherein the heavy chain of the antibody comprises at least a portion of the amino acid sequence set forth herein at SEQ ID NO: 14, such as the CDRs of SEQ ID NO: 14; or the light chain of the antibody comprises at least a portion of the amino acid sequence set forth herein as SEQ ID NO: 16 or SEQ ID NO: 31, such as the CDRs of SEQ ID NO: 16 or SEQ ID NO: 31; or both. In some embodiments, the antibodies comprise a heavy chain having one or more (such as all three) CDR sequences from SEQ ID NO: 14 and/or comprise a light chain having one or more (such as all three) CDR sequences from SEQ ID NO: 16, as determined using the Kabat method. In some embodiments, the antibodies comprise a heavy chain having one or more (such as all three) CDR sequences from SEQ ID NO: 14 and/or comprise a light chain having one or more (such as all three) CDR sequences from SEQ ID NO: 31, as determined using the Kabat method.

In some embodiments, the antibodies comprise a heavy chain having one or more (such as all three) CDR sequences from SEQ ID NO: 14 and/or comprise a light chain having one or more (such as all three) CDR sequences from SEQ ID NO: 16, as determined by IMGT. In other embodiments, the antibodies comprise a heavy chain having one or more (such as all three) CDR sequences from SEQ ID NO: 14 and/or comprise a light chain having one or more (such as all three) CDR sequences from SEQ ID NO: 31, as determined by IMGT.

In some embodiments, provided herein is an isolated human monoclonal antibody that binds (for example specifically binds) HS on GPC3, wherein the heavy chain of the antibody comprises amino acid residues 31-35 of SEQ ID NO: 14, amino acid residues 50-66 of SEQ ID NO: 14, or amino acid residues 97-105 of SEQ ID NO: 14, or any combination thereof; or the light chain of the antibody comprises amino acid residues 24-34 of SEQ ID NO: 16 or SEQ ID NO: 31, amino acid residues 50-56 of SEQ ID NO: 16 or SEQ ID NO: 31, or amino acid residues 89-97 of SEQ ID NO: 16 or SEQ ID NO: 31, or any combination thereof.

In some examples, the heavy chain of the antibody comprises amino acid residues 31-35, 50-66 and 97-105 of SEQ ID NO: 14; or the light chain of the antibody comprises amino acid residues 24-34, 50-56 and 89-97 of SEQ ID NO: 16; or both. In other examples, the heavy chain of the antibody comprises amino acid residues 31-35, 50-66 and 97-105 of SEQ ID NO: 14; or the light chain of the antibody comprises amino acid residues 24-34, 50-56 and 89-97 of SEQ ID NO: 31; or both.

In some embodiments, provided herein is an isolated human monoclonal antibody that binds (for example, specifically binds) HS on GPC3, wherein the heavy chain of the antibody comprises amino acid residues 26-33 of SEQ ID NO: 14, amino acid residues 51-58 of SEQ ID NO: 14, or amino acid residues 97-105 of SEQ ID NO: 14, or any combination thereof; or the light chain of the antibody comprises amino acid residues 27-32 of SEQ ID NO: 16 or SEQ ID NO: 31, amino acid residues 50-52 of SEQ ID NO: 16 or SEQ ID NO: 31, or amino acid residues 89-97 of SEQ ID NO: 16 or SEQ ID NO: 31, or any combination thereof.

In some examples, the heavy chain of the antibody comprises amino acid residues 26-33, 51-58 and 97-105 of SEQ ID NO: 14; or the light chain of the antibody comprises amino acid residues 27-32, 50-52 and 89-97 of SEQ ID NO: 16; or both. In other examples, the heavy chain of the antibody comprises amino acid residues 26-33, 51-58 and 97-105 of SEQ ID NO: 14; or the light chain of the antibody comprises amino acid residues 27-32, 50-52 and 89-97 of SEQ ID NO: 31; or both.

In some examples, the heavy chain of the antibody comprises the amino acid sequence of SEQ ID NO: 14; or the light chain of the antibody comprises the amino acid sequence of SEQ ID NO: 16; or both. In other examples, the heavy chain of the antibody comprises the amino acid sequence of SEQ ID NO: 14; or the light chain of the antibody comprises the amino acid sequence of SEQ ID NO: 31; or both.

In some embodiments, the disclosed antibodies bind GPC3 with a $K_d$ of about 2.5 nM or less. In several embodiments, the human monoclonal antibodies bind GPC3 with a binding affinity of about 1 nM or less. In some examples, the human monoclonal antibodies bind GPC3 with a binding affinity of about 0.9 nM, about 0.8 nM, about 0.75 nM, about 0.7 nM, about 0.6 nM, or about 0.5 nM.

In some embodiments, the human monoclonal antibody is a VH single-domain antibody, a Fab fragment, a Fab' fragment, a F(ab)'$_2$ fragment, a single chain variable fragment (scFv), or a disulfide stabilized variable fragment (dsFv). In one non-limiting example, the antibody is a scFv. In other examples, the antibody is an IgG.

The isolated human monoclonal antibodies that bind HS chains on GPC3 disclosed herein can be labeled, such as with a fluorescent, enzymatic, or radioactive label.

Further provided herein are compositions comprising a therapeutically effective amount of the disclosed antibodies and a pharmaceutically acceptable carrier.

Immunoconjugates comprising the human monoclonal antibodies specific for HS on GPC3 disclosed herein and an effector molecule are also provided. The effector molecule can be, for example, a toxin or a detectable label. Examples of immunoconjugates are discussed in greater detail in section V below. Also provided are compositions comprising a therapeutically effective amount of the immunoconjugates disclosed herein and a pharmaceutically acceptable carrier.

Further provided herein are isolated nucleic acid molecules encoding the disclosed human monoclonal antibodies. In some embodiments, the nucleotide sequence encoding the heavy chain of the human monoclonal antibody comprises at least a portion of SEQ ID NO: 13, such as a portion encoding one or more CDRs; or the nucleotide sequence encoding the light chain of the human monoclonal antibody comprises at least a portion of SEQ ID NO: 15 or SEQ ID NO: 30, such as a portion encoding one or more CDRs; or both.

In some examples, the nucleotide sequence encoding the heavy chain of the human monoclonal antibody comprises SEQ ID NO: 13; or the nucleotide sequence encoding the light chain of the human monoclonal antibody comprises SEQ ID NO: 15 or SEQ ID NO: 30; or both. In some examples, the isolated nucleic acid molecule is operably linked to a promoter.

Also provided are expression vectors comprising the isolated nucleic acid molecules disclosed herein. Isolated host cells comprising the nucleic acid molecules or vectors are also provided herein. In some examples, the host cell is a T cell, such as a CTL.

C. Antibodies and Antibody Fragments

The monoclonal antibodies disclosed herein can be of any isotype. The monoclonal antibody can be, for example, an IgM or an IgG antibody, such as IgG$_1$ or an IgG$_2$. The class of an antibody that specifically binds GPC3, or HS on GPC3, can be switched with another (for example, IgG can be switched to IgM), according to well-known procedures. Class switching can also be used to convert one IgG subclass to another, such as from IgG$_1$ to IgG$_2$.

Antibody fragments are also encompassed by the present disclosure, such as single-domain antibodies (e.g., VH domain antibodies), Fab, F(ab')$_2$, and Fv. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFv (also known as a "miniantibody"); and (7) VH single-domain antibody, an antibody fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and/or the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

V. Immunoconjugates

The human monoclonal antibodies specific for GPC3, or HS on GPC3, described herein can be conjugated to a therapeutic agent or effector molecule. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

A human antibody that binds (for example specifically binds) GPC3, or HS chains on GPC3, can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect GPC3 by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the human monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pal et al., *Proc. Natl Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

In some examples, the PE is PE38, comprising the following amino acid sequence:

```
                                      (SEQ ID NO: 27)
GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANGPADSGDALLERNYPTGAEFLGDGGDVSFSTRGTQNWT

VERLLQAHRQLEERGYVFVGYHGTFLEAAQSIVFGGVRARSQDLDAIWRG

FYIAGDPALAYGYAQDQEPDARGRIRNGALLRVYVPRSSLPGFYRTSLTL

AAPEAAGEVERLIGHPLPLRLDAITGPEEEGGRLETILGWPLAERTVVIP

SAIPTDPRNVGGDLDPSSIPDKEQAISALPDYASQPGKPPREDLK
```

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954) having the following amino acid sequence:

```
                                      (SEQ ID NO: 23)
RHRQPRGWEQLPTGAEFLGDGGDVSFSTRGTQNWTVERLLQAHRQLEERG

YVFVGYHGTFLEAAQSIVFGGVRARSQDLDAIWRGFYIAGDPALAYGYAQ

DQEPDARGRIRNGALLRVYVPRSSLPGFYRTSLTLAAPEAAGEVERLIGH

PLPLRLDAITGPEEEGGRLETILGWPLAERTVVIPSAIPTDPRNVGGDLD

PSSIPDKEQAISALPDYASQPGKPPREDLK
```

In other examples, the PE is a variant designated PE-LR/6X (PCT Publication No. WO 2011/032022) having the following amino acid sequence:

```
                                      (SEQ ID NO: 24)
RHRQPRGWEQLPTGAEFLGDGGDVSFSTRGTQNWTVERLLQAHRQLEEGG

YVFVGYHGTFLEAAQSIVFGGVRARSQDLDAIWAGFYIAGDPALAYGYAQ

DQEPDAAGRIRNGALLRVYVPRSSLPGFYATSLTLAAPEAAGEVERLIGH

PLPLRLDAITGPEESGGRLETILGWPLAERTVVIPSAIPTDPRNVGGDLD

PSSIPDSEQAISALPDYASQPGKPPREDLK
```

In other examples, the PE variant is PE with reducing immunogenicity, such as a PE with the following sequence:

(X = G, A or S; SEQ ID NO: 25)
RHRQPRGWEQLPTGAEFLGDGGXVSFSTRGTQNWTVERLLQAHRQLEEXG

YVFVGYHGTFLEAAQSIVFGGVRARSQDLDAIWXGFYIAGDPALAYGYAQ

DQEPDAXGRIRNGALLRVYVPRSSLPGFYXTSLTLAAPEAAGEVERLIGH

PLPLRLDAITGPEEXGGRLETILGWPLAERTVVIPSAIPTDPRNVGGDLD

PSSIPDXEXAISALPDYASQPGKPPREDLK

In other examples, the PE is a variant designated PE-LR/8M (PCT Publication No. WO 2011/032022) having the following amino acid sequence:

(SEQ ID NO: 26)
RHRQPRGWEQLPTGAEFLGDGGAVSFSTRGTQNWTVERLLQAHRQLEEGG

YVFVGYHGTFLEAAQSIVFGGVRARSQDLDAIWAGFYIAGDPALAYGYAQ

DQEPDAAGRIRNGALLRVYVPRSSLPGFYATSLTLAAPEAAGEVERLIGH

PLPLRLDAITGPEESGGRLETILGWPLAERTVVIPSAIPTDPRNVGGDLD

PSSIPDSEAAISALPDYASQPGKPPREDLK

The antibodies described herein can also be used to target any number of different diagnostic or therapeutic compounds to cells expressing GPC3 on their surface. Thus, an antibody of the present disclosure can be attached directly or via a linker to a drug that is to be delivered directly to cells expressing cell-surface GPC3. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-GPC3 antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Compositions and Methods of Use

Compositions are provided that include one or more of the disclosed antibodies that bind (for example specifically bind) GPC3 or HS on GPC3 in a carrier. Compositions comprising immunoconjugates or immunotoxins are also provided. The compositions can be prepared in unit dosage forms for administration to a subject. The amount and timing of administration are at the discretion of the treating clinician to achieve the desired outcome. The antibody can be formulated for systemic or local (such as intra-tumor) administration. In one example, the antibody is formulated for parenteral administration, such as intravenous administration.

The compositions for administration can include a solution of the antibody dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies, compositions and immunoconjugates disclosed herein can be administered to slow or inhibit the growth of tumor cells or inhibit the metastasis of tumor cells, such as HCC cells. In these applications, a therapeutically effective amount of an antibody is administered to a subject in an amount sufficient to inhibit growth, replication or metastasis of cancer cells, or to inhibit a sign or a symptom of the cancer. Suitable subjects may include those diagnosed with a cancer that expresses GPC3, such as, but not limited to, HCC, melanoma, lung cancer or ovarian cancer.

In one non-limiting embodiment, provided herein is a method of treating a subject with cancer by selecting a subject with a cancer that expresses GPC3 and administering to the subject a therapeutically effective amount of an antibody, composition or immunoconjugate disclosed herein.

Also provided herein is a method of inhibiting tumor growth or metastasis by selecting a subject with a cancer that expresses GPC3 and administering to the subject a therapeutically effective amount of an antibody, composition or immunoconjugate disclosed herein.

A therapeutically effective amount of a human GPC3-specific antibody or immunoconjugate will depend upon the severity of the disease and the general state of the patient's health. A therapeutically effective amount of the antibody is that which provides either subjective relief of a symptom(s) or an objectively identifiable improvement as noted by the clinician or other qualified observer.

Administration of the antibodies and immunoconjugates disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting expression of GPC3 in vitro or in vivo. In some cases, GPC3 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with a human monoclonal antibody disclosed herein; and detecting binding of the antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with a human monoclonal antibody disclosed herein; and detecting binding of the antibody to the sample. An increase in binding of the antibody to the sample as compared to binding of the antibody to a control sample confirms the diagnosis of cancer in the subject.

In some examples of the disclosed methods, the human monoclonal antibody is directly labeled.

In some examples, the methods further include contacting a second antibody that specifically binds the human monoclonal antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is HCC, melanoma, lung cancer or ovarian cancer, or any other type of cancer that expresses GPC3.

In some examples, the control sample is a sample from a subject without cancer. In particular examples, the sample is a blood or tissue sample.

In some cases, the human antibody that binds (for example specifically binds) GPC3 (or HS chains on GPC3) is directly labeled with a detectable label. In another embodiment, the human antibody that binds (for example, specifically binds) GPC3 (the first antibody) is unlabeled and a second antibody or other molecule that can bind the human antibody that specifically binds GPC3 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, GPC3 can be assayed in a biological sample by a competition immunoassay utilizing GPC3 standards labeled with a detectable substance and an unlabeled human antibody that specifically binds GPC3. In this assay, the biological sample, the labeled GPC3 standards and the human antibody that specifically bind GPC3 are combined and the amount of labeled GPC3 standard bound to the unlabeled antibody is determined. The amount of GPC3 in the biological sample is inversely proportional to the amount of labeled GPC3 standard bound to the antibody that specifically binds GPC3.

The immunoassays and method disclosed herein can be used for a number of purposes. In one embodiment, the human antibody that specifically binds GPC3 may be used to detect the production of GPC3 in cells in cell culture. In another embodiment, the antibody can be used to detect the amount of GPC3 in a biological sample.

In one embodiment, a kit is provided for detecting GPC3 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble GPC3 protein or fragment. Kits for detecting a polypeptide will typically comprise a human antibody that specifically binds GPC3, such as any of the antibodies disclosed herein. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds GPC3. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting GPC3 in a biological sample generally includes the steps of contacting the biological sample with an antibody which specifically reacts, under immunologically reactive conditions, to a GPC3 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the human antibodies that bind GPC3 (or HS chains on GPCS), as disclosed herein, can be used in these assays. Thus, the antibodies can be used in a conventional immunoassay, including, without limitation, an ELISA, an RIA, FACS, tissue immunohistochemistry, Western blot or immunoprecipitation.

C. Engineered Cytotoxic T Lymphocytes (CTLs)

The disclosed monoclonal antibodies can also be used to produce CTLs engineered to express chimeric antigen receptors (CARs; also known as chimeric T cell receptors, artificial T cell receptors or chimeric immunoreceptors). Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv. Several different endodomains have been used to generate CARs. For example, the endodomain can consist of a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, the monoclonal antibodies disclosed herein can be used to engineer CTLs that express a CAR containing an antigen-binding fragment of a GPC3-specific antibody, thereby targeting the engineered CTLs to GPC3-expressing tumor cells. Engineered T cells have previously used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expressed the target antigen.

Accordingly, provided herein are CARs comprising a GPC3-specific antibody binding fragment, such as a scFv. Also provided are isolated nucleic acid molecules and vectors encoding the CARs, and host cells, such as CTLs, comprising the nucleic acid molecules or vectors. CTLs expressing CARs comprised of a GPC3-specific antibody binding fragment can be used for the treatment of cancers that express GPC3, such as HCC. Thus, provided herein are methods of treating a subject with cancer by selecting a subject with a cancer that expresses GPC3, and administering to the subject a therapeutically effective amount of the CTLs expressing the GPC3-targeted CARs.

D. Bispecific Antibodies

Bispecific antibodies are recombinant proteins comprised of antigen-binding fragments of two different monoclonal antibodies. Thus, bispecific antibodies bind two different antigens. Bispecific antibodies can be used for cancer immunotherapy by simultaneously targeting both CTLs (such as a CTL receptor component such as CD3) and a tumor antigen. The GPC3-specific monoclonal antibodies disclosed herein can be used to generate bispecific antibodies that target both GPC3 and CTLs, thereby providing a means to treat GPC3-expressing cancers.

Provided herein are bispecific monoclonal antibodies comprising a GPC3-specific monoclonal antibody, or antigen-binding fragment thereof. In some embodiments, the bispecific monoclonal antibody further comprises a monoclonal antibody, or antigen-binding fragment thereof, that specifically binds a component of the T cell receptor, such as CD3. Also provided are isolated nucleic acid molecules and vectors encoding the bispecific antibodies, and host cells comprising the nucleic acid molecules or vectors. Bispecific antibodies comprising a GPC3-specific antibody, or antigen-binding fragment thereof, can be used for the treatment of cancers that express GPC3, such as HCC. Thus, provided herein are methods of treating a subject with cancer by selecting a subject with a cancer that expresses GPC3, and administering to the subject a therapeutically effective amount of the GPC3-targeting bispecific antibody.

The following examples are provided to illustrate certain particular features and/or embodiments. These examples should not be construed to limit the disclosure to the particular features or embodiments described.

EXAMPLES

Example 1: HN3—a Human Single-Domain Monoclonal Antibody that Binds Cell Surface-Associated Glypican-3 and Inhibits HCC Cell Proliferation This example describes the generation and characterization of a high-affinity single-domain mAb against tumor-associated GPC3.

A. Materials and Methods

Cell Lines

Human hepatocarcinoma cell lines HepG2, Hep3B, HuH-1, HuH-4, HuH-7, and SK-Hep1 were maintained as adherent monolayer cultures in D-MEM medium (Invitrogen, Carlsbad, Calif.) supplemented with 10% fetal bovine serum (HyClone, Logan, Utah), 1% L-glutamine, and 1% penicillin-streptomycin (Invitrogen, Carlsbad, Calif.) and incubated in 5% $CO_2$ with a balance of air at 37° C. Cells were harvested and the media were changed twice a week. Cells were confirmed to be negative for *mycoplasma*. A431 (human epithelial carcinoma cell line), which is GPC3 negative cell line, was engineered to express high levels of GPC3 by transfection with a plasmid coding for GPC3. Both A431 and the stably transfected cell line (named G1) were maintained in D-MEM as described above.

Phage Display and Panning Method

A combinatorial human VH domain library, with an estimated size of $2.5 \times 10^{10}$, was previously constructed (Chen et al., *J Mol Biol* 382:779-789, 2008). Library bacterial stock was inoculated into 2.5 liters of 2YT media containing 2% glucose and 100 µg/ml ampicillin, and cultured at 37° C. with shaking at 250 rpm. When mid-log phase ($OD_{600}$ between 0.4-0.8) was reached, super-infection was performed by adding helper phage M13KO7 at $5 \times 10^9$ pfu/ml. After one hour of continued growth, cells were collected and resuspended in 2.5 liters of 2YT media containing 100 µg/ml ampicillin and 50 µg/ml kanamycin. The cell culture was then further incubated at 25° C. overnight. The cells were pelleted, and the supernatant was filtered with a 0.22 µm membrane and then stored at 4° C. for panning.

Recombinant GPC3 was expressed in 293F cells and purified by nickel column chromatography as previously reported (Feng et al., *Int J Cancer* 128(9):2246-2247, 2011). For panning, a 96-well ELISA plate (Maxisorb, Nunc/Thermo Fisher Scientific, Rochester, N.Y.) was used to capture various mount of purified GPC3 in phosphate buffered saline (PBS) at 4° C. overnight. The coating buffer was decanted, and the plate was blocked with blocking buffer (2% bovine serum albumin (BSA) in PBS) at room temperature for 1 hour. At the same time, 30 µl phage supernatant (typically contained $10^{10}$-$10^{11}$ cfu) was pre-blocked by mixing with 30 µl blocking buffer in an Ependorf tube. Blocking buffer was removed from the plate and 60 µl pre-blocked phage supernatant was added to one well and incubated for 1 h at room temperature to allow for binding. Unbound phage was removed and the plate was washed 4 times with PBS containing 0.05% tween-20. The bound phage was eluted by 100 mM TEA. For the first round of panning, 5 µg immobilized GPC3 was used; 0.5 µg GP3 was used for the second, third and fourth rounds of panning. After four rounds of panning, single colonies were picked and identified as GPC3 binders by using phage ELISA and phage FACS methods.

HN3-hFc Expression and Purification

HN3-hFc was expressed in HEK-293F cells in a suspension manner. Secreted GPC3 protein was purified using protein A column (GE healthcare) according to the manufacturer's instructions.

Flow Cytometry

Cells were harvested in cell dissociation solution (Invitrogen), washed, and resuspended in ice-cold PBS containing 5% BSA. Cells were incubated with 10 µg/mL of HN3-hFc and an isotype control human IgG (Southern Biotech). Binding was detected with goat anti-human IgG conjugated with phycoerythrin (Sigma-Aldrich, St. Louis, Mo.). The fluorescence associated with the live cells was measured using a FACSCalibur (BD Biosciences, Franklin Lakes, N.J.).

For the cellular binding affinity measurement, various amounts of HN3-hFc were incubated with G1 cells. The geomean values were associated with corresponding HN3-hFc concentration, and kD value was determined by the software Prism 5.0 using one-site binding method.

For the phage FACS, 30 µl phage supernatant was pre-blocked with FACS buffer for 1 hour on ice, and then mixed with G1 cell suspension. Binding was detected by mouse anti-M13 and PE conjugated goat-anti-mouse antibody.

ELISA

Purified GPC3 was used to coat 96-well plate at 1 µg/ml in PBS buffer, 50 µl/well, at 4° C. overnight. After removing the coating buffer, HN3-hFc solution was added and the plate was incubated at room temperature to allow binding to occur. After removing HN3-hFc solution, the plate was washed twice with PBS buffer containing 0.05% Tween 20. The binding was detected by a goat-anti-human-HRP conjugate (Biosource).

For phage ELISA, 30 µl phage supernatant was pre-blocked with blocking buffer, then processed according to the standard ELISA method. Binding was detected by HRP conjugated mouse anti-M13 antibody (GE healthcare).

For the HN3-hFc affinity measurement, various amounts of HN3-hFc were incubated. The $OD_{450}$ values were associated with corresponding HN3-hFc concentration, and kD value was determined by the software Prism 5.0 (GraphPad Software) using one-site binding method.

WST-8 Cell Growth Assay

Cell growth inhibition was assessed by WST-8 assay using the Cell Counting Kit-8 (Dojindo, Gaithersburg, Md.) according to the manufacturer's instructions. Five hundred microliters of cells were seeded on a 24-well plate at $1 \times 10^4$ cells per well, with the addition of HN3-hFc at the indicated concentrations. The cells were incubated at 37° C. for 4 days, followed by the cell viability assay as previously reported (Ho et al., *Int J Cancer* 128:2020-2030, 2011)

B. Results

Isolation of an Anti-GPC3 Single-Domain Human mAb

The single-domain library used in the present study was constructed based on the frame regions of the highly soluble antibody m0 (Chen et al., *J Mol Biol* 382:779-789, 2008), which has a sequence similar to the germ line counterpart DP47. DP47 is highly soluble and refoldable (Jespers et al., *J Mol Bio* 337: 893-903, 2004).

Figure 1B:
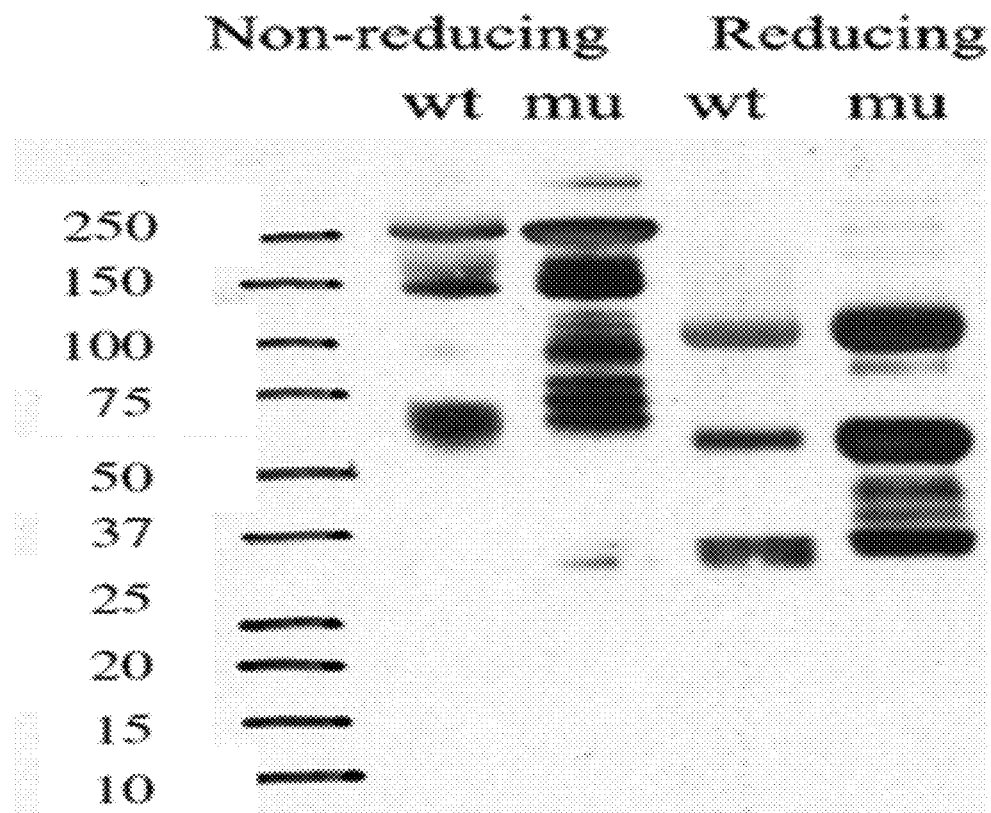

To screen antibodies specific for the core protein or the HS chain of GPC3, two human Fc fusion proteins were constructed and produced: GPC3-hFc and GPC3 (AA)-hFc proteins. The Fc fragment contains the hinge region with the CH2 and CH3 domains. GPC3 (AA)-hFc contains the two point mutations (S495A and S502A) which abolish the HS chains on GPC3. The molecular weights and purity of the proteins were validated by SDS-PAGE and Western blot (FIG. 1). The purity was greater than 90%. The single-domain phage display library was then screened on 5 µg of GPC3 coated on a flat 96-well ELISA plate for the first round and then against 0.5 µg of GPC3 in the following 3 rounds of panning. After the first round of phage panning, about 9000 individual phage clones were obtained. At the end of the fourth round of panning, more than 95% of clones were GPC3 binders; HN3 was the dominant clone that was highly enriched. Sequence analysis showed that HN3 shared the same sequence in the frame region as that of m0 and DP47 (FIG. 2).

High Affinity Binding of HN3 to Cell Surface-Associated GPC3

Figure 3A:
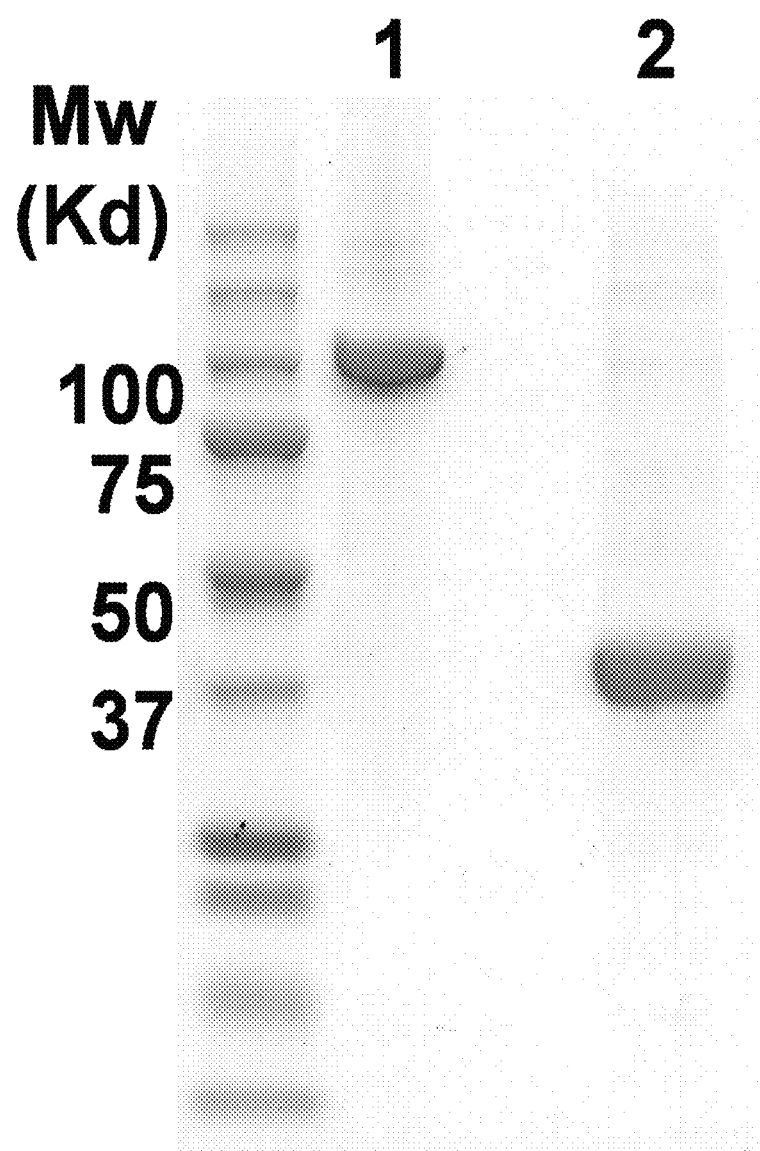
FIG. 3A is a gel showing SDS-PAGE analysis of HN3-hFc. Lane 1, 5 μg non-reducing; Lane 2, 5 μg reducing.

To examine the binding properties of HN3 on cancer cells, the HN3-human Fc fusion protein (HN3-hFc) was constructed and purified using a Protein A column. SDS-PAGE analysis showed that it formed a dimer with a molecular weight of approximately 80 kDa. Under reduced conditions, the molecular weight was approximately 40 kDa (FIG. 3A).

Figure 3B:
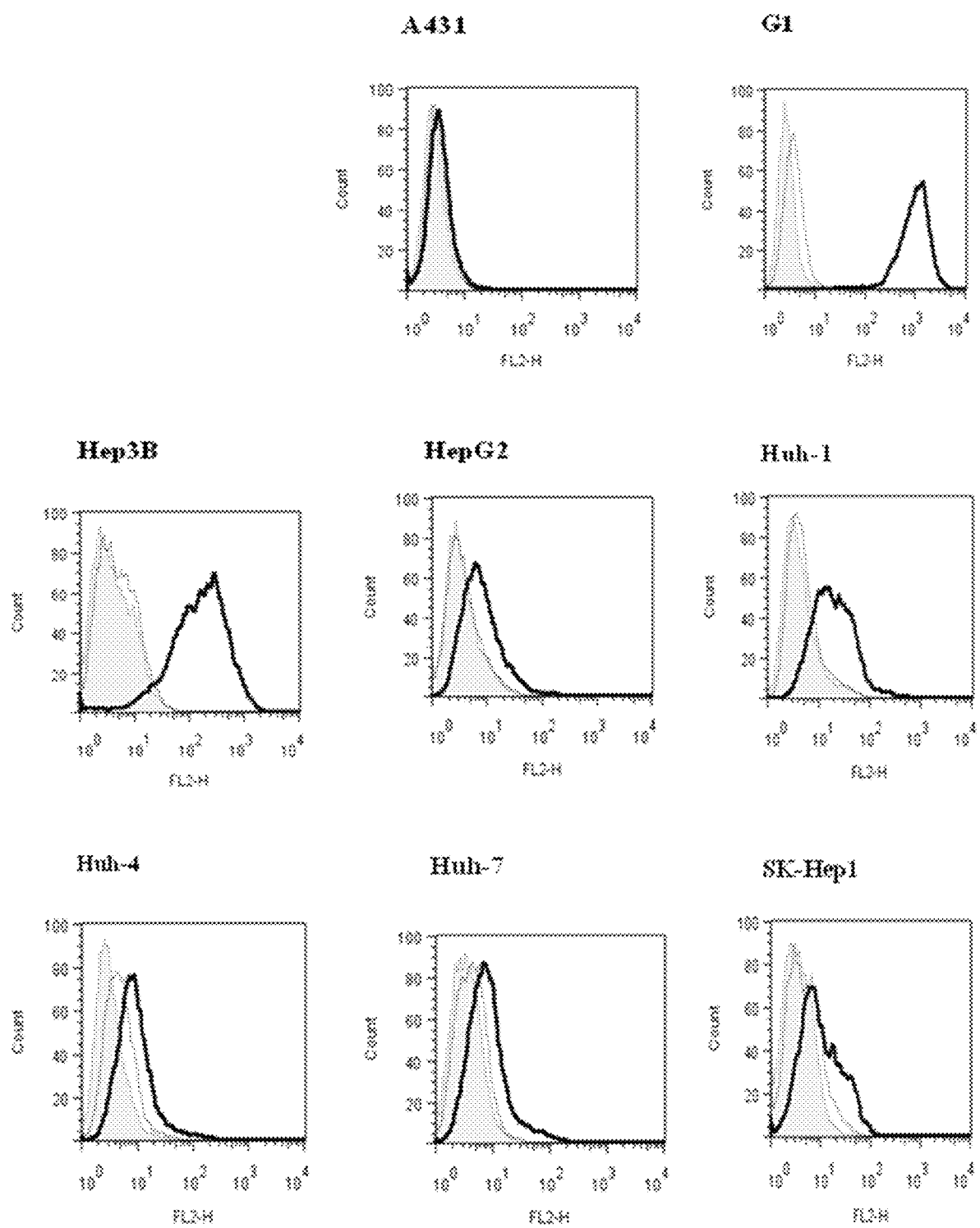
FIG. 3B is a series of flow cytometry plots showing that HN3 binds GPC3-positive G1 cells, but not GPC3-negative A431 cells. HN3 also binds a panel of HCC cell lines (Hep3B, HepG2, Huh-1, Huh-4, Huh7 and SK-Hep1).
Figure 4A:
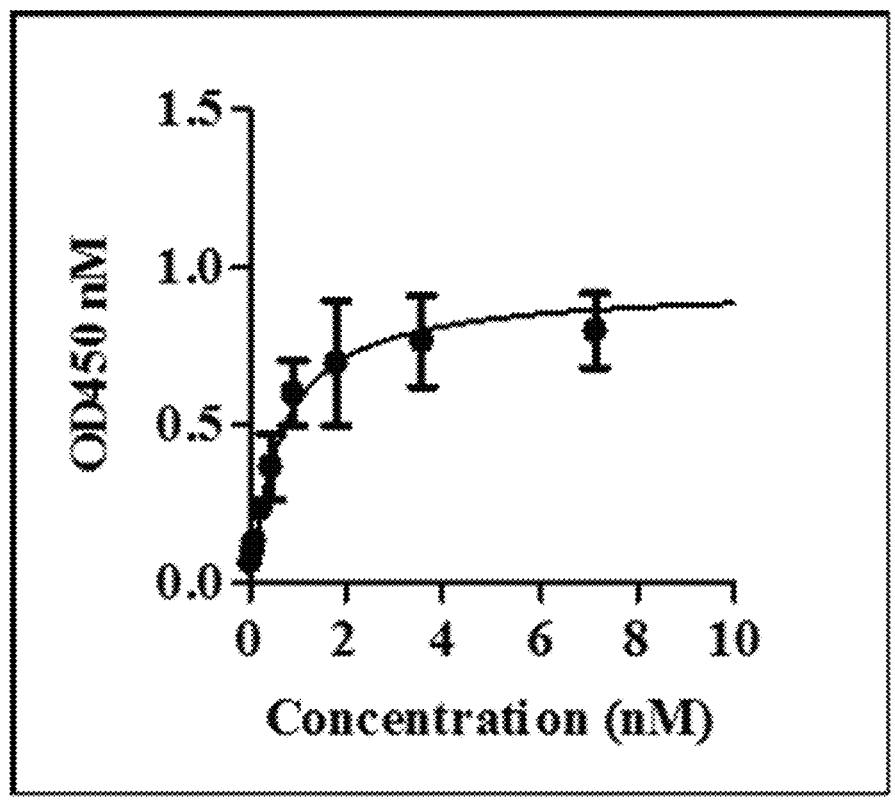
FIGS. 4A and 4B are graphs showing high binding affinity of HN3 for GPC3.

HN3-hFc was then used to test six HCC cell lines, one negative cell line A431, and the A431-derived cell line G1. The G1 cell line stably and highly expresses GPC3 on the cell surface. HN3 showed specific binding on HCC cells and G1 cells, but no binding on GPC3-negative A431 cancer cells (FIG. 3B). The binding affinities of HN3 to GPC3 protein and GPC3-positive cells were measured by ELISA and flow cytometry, respectively. The binding affinities for both GPC3 protein and cells were very strong, with calculated $K_D$ values of 0.64 nM for GPC3 protein and 0.15 nM for cell surface-associated GPC3 (FIG. 4). HN3 bound cell surface-associated GPC3 stronger than soluble GPC3 protein, probably due to the native conformation of GPC3 on the cell surface. HN3 did not recognize denatured GPC3 by Western Blot, indicating the binding of HN3 might be conformation-dependent.

Figure 5A:
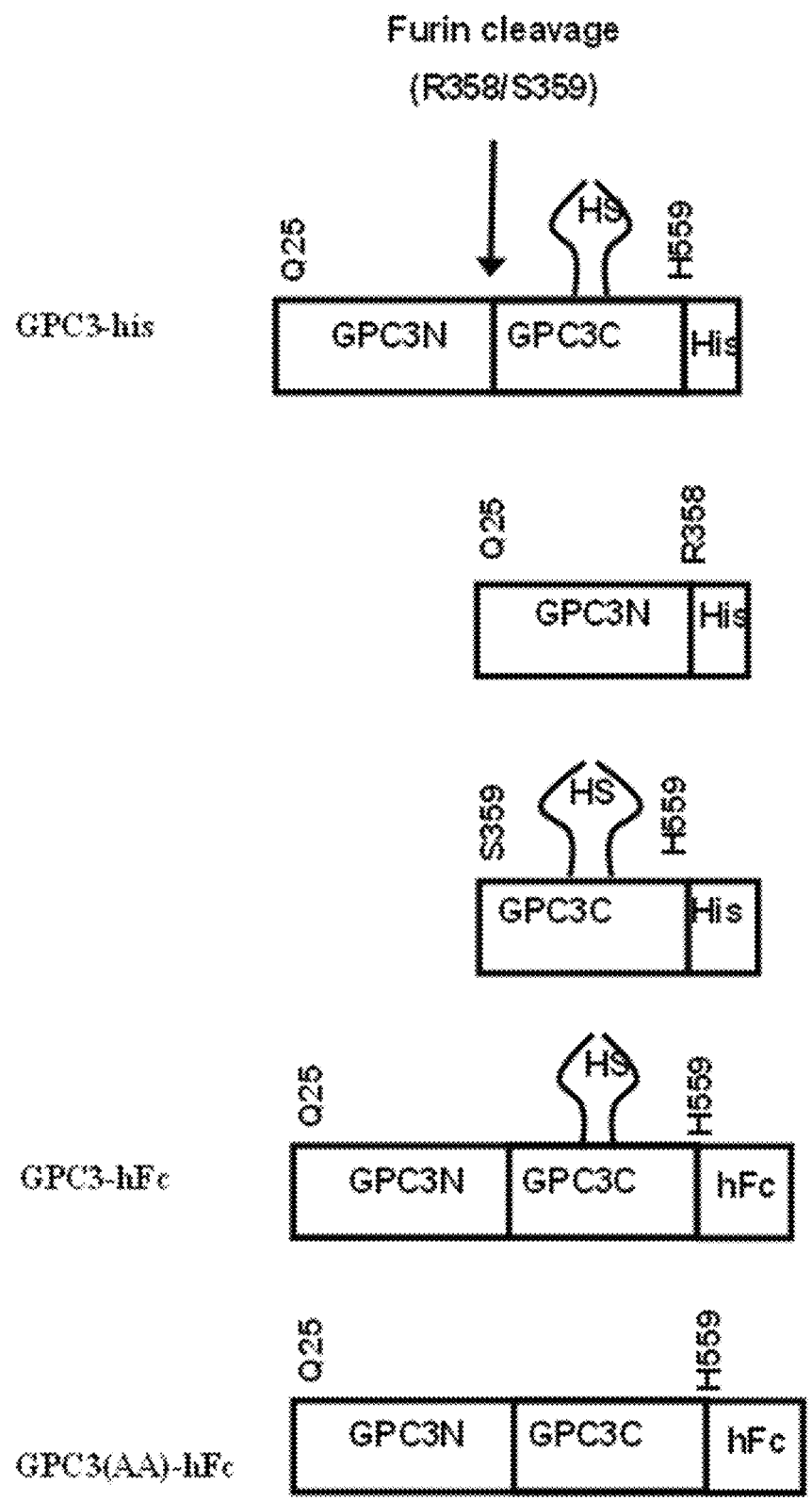
FIG. 5A is a schematic diagram of the primary structures of various recombinant GPC3 proteins. His, six histidine tag; hFc, human IgG1 Fc tag; HS, heparan sulfate glycosaminoglycan. IAB-hFc was used as a hFc isotype control.
Figure 5B:
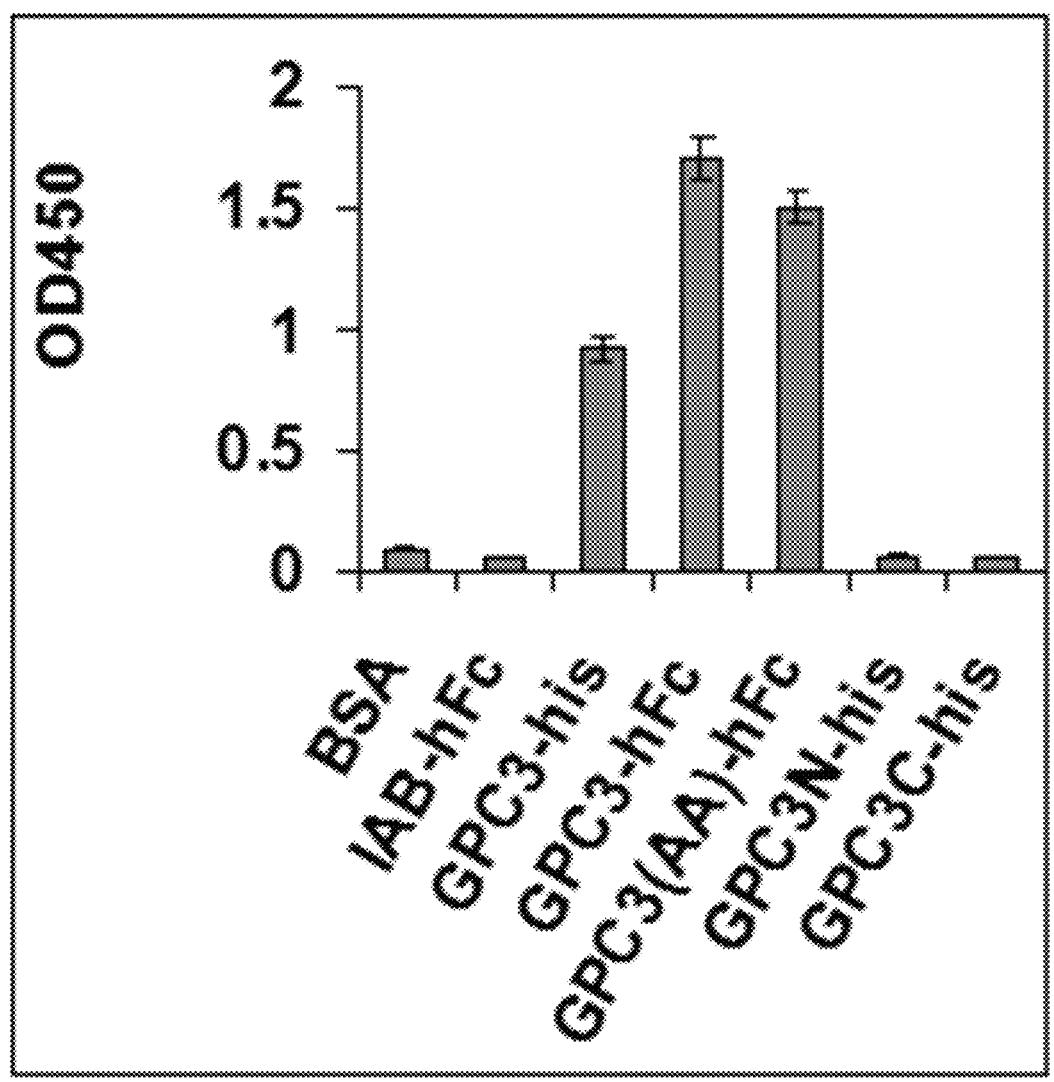
FIG. 5B is a graph showing results of a phage ELISA demonstrating that clone HN3 binds to the full-length GPC3 independent of its tags (Fc or His), but not the GPC3 fragments (N- or C-terminus alone).

Epitope mapping results showed that HN3 bound the wild type GPC3 protein as strong as the mutant GPC3 without the HS chains. Therefore, HN3 binds to the core protein of GPC3. The binding was independent of the HS chains. Moreover, HN3 didn't bind either the N-terminal fragment or the C-terminal fragment, indicating again HN3 recognized a native conformation in the core protein of GPC3 (FIG. 5).

Figure 6A:
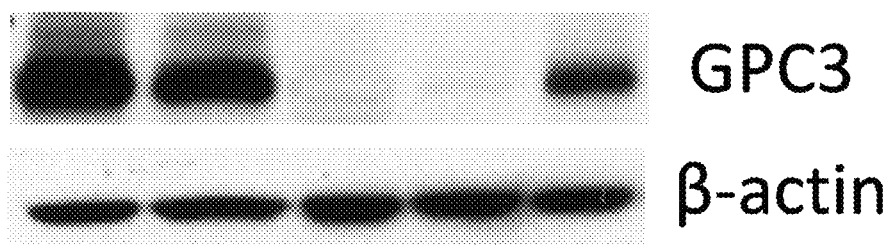
FIGS. 6A-6D are a series of figures showing HN3 inhibits HCC cell proliferation in vitro.
Figure 6B:
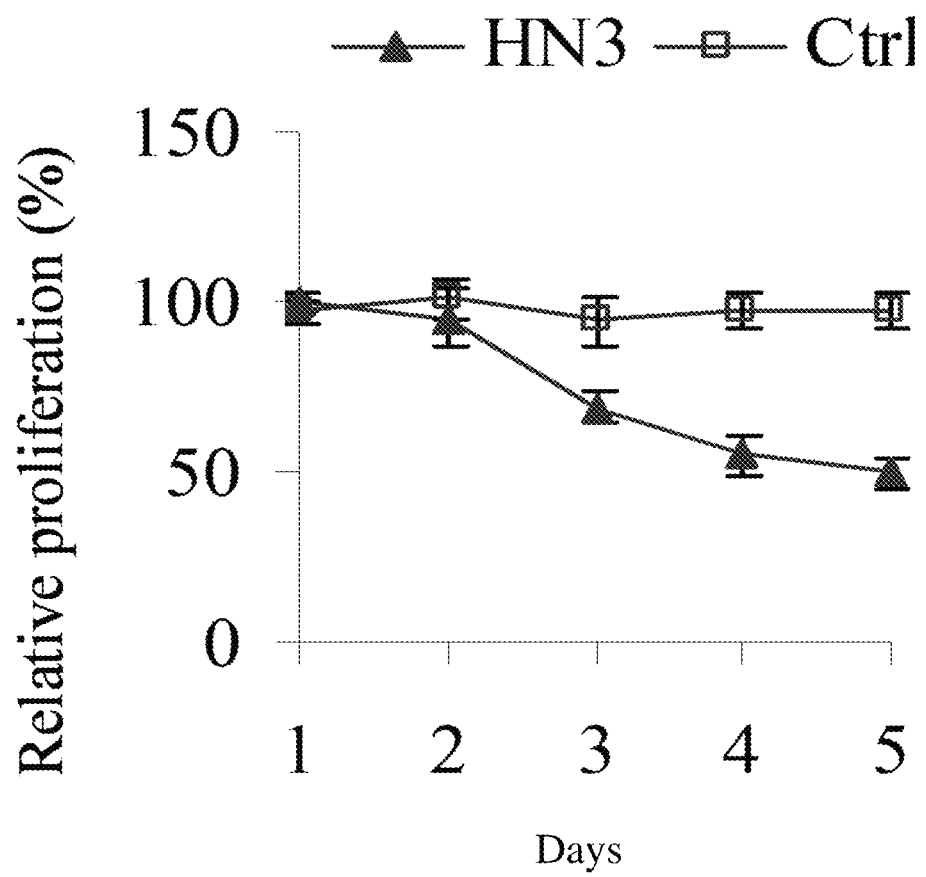
Figure 6C:
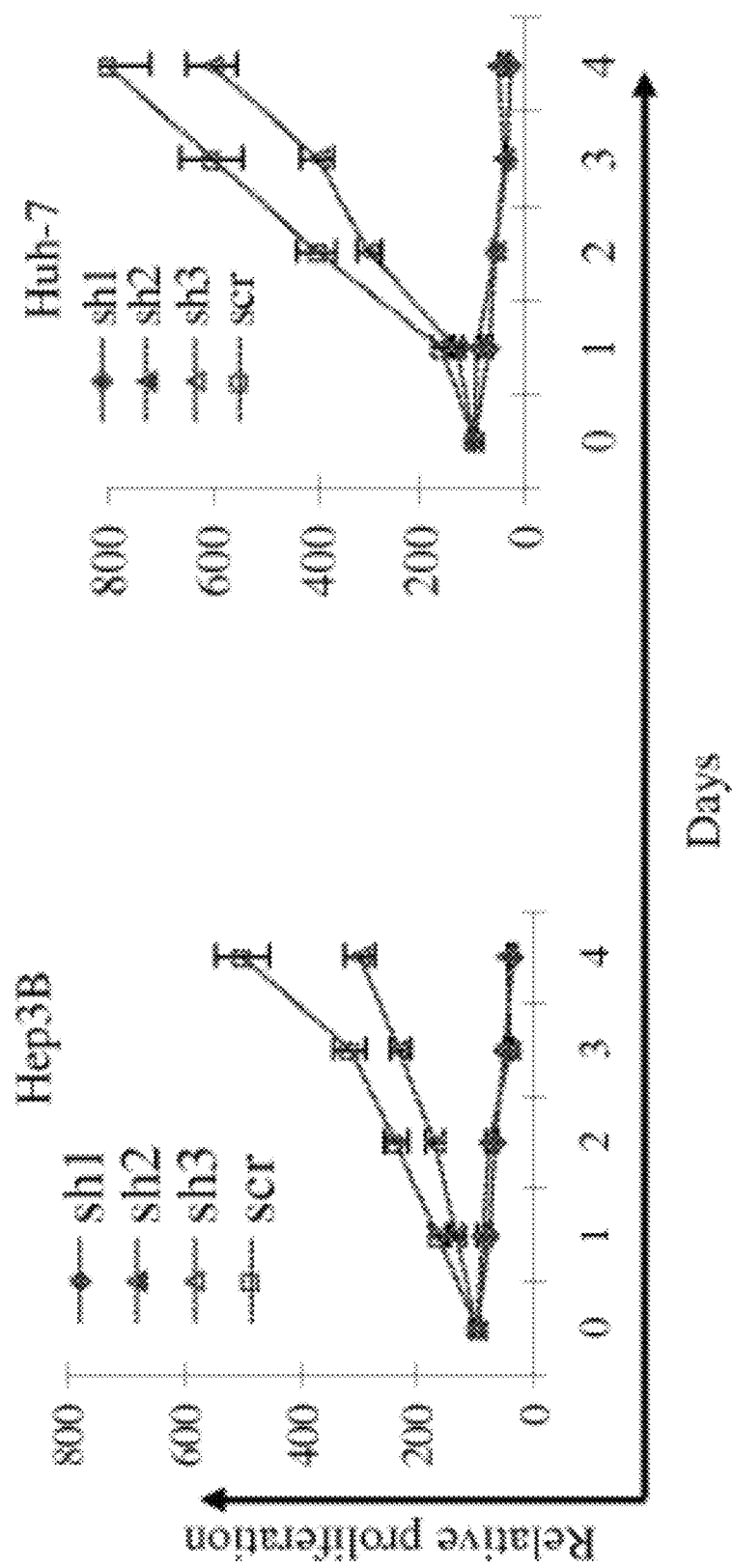

HN3 Treatment Inhibited HCC Cell Proliferation by Causing Cell Cycle Arrest and Apoptosis To determine the effects of specific GPC3 depletion on the proliferation and survival of human HCC tumor cell lines, three different GPC3-specific shRNAs were used to knock down GPC3 mRNA/protein. The cell lines studied for sensitivity included Hep3B and Huh-7, both HCC cell lines. Efficient knockdown of GPC3 protein by specific shRNA was verified by immunoblotting (FIG. 6A). The shRNAs sh-1 and sh-2 reduced >90% of GPC3 expression in HCC cells while the shRNA sh-3 only moderately reduced ~10% of GPC3 expression in HCC cells (FIG. 6A). Exposure of Hep3B and Huh-7 cell lines to GPC3-specific shRNA (sh-1 and sh-2) in culture resulted in a profound inhibition of proliferation (FIGS. 6B and 6C). In contrast, exposure of the same cells to a control (scrambled) shRNA did not affect proliferation.

Figure 6D:
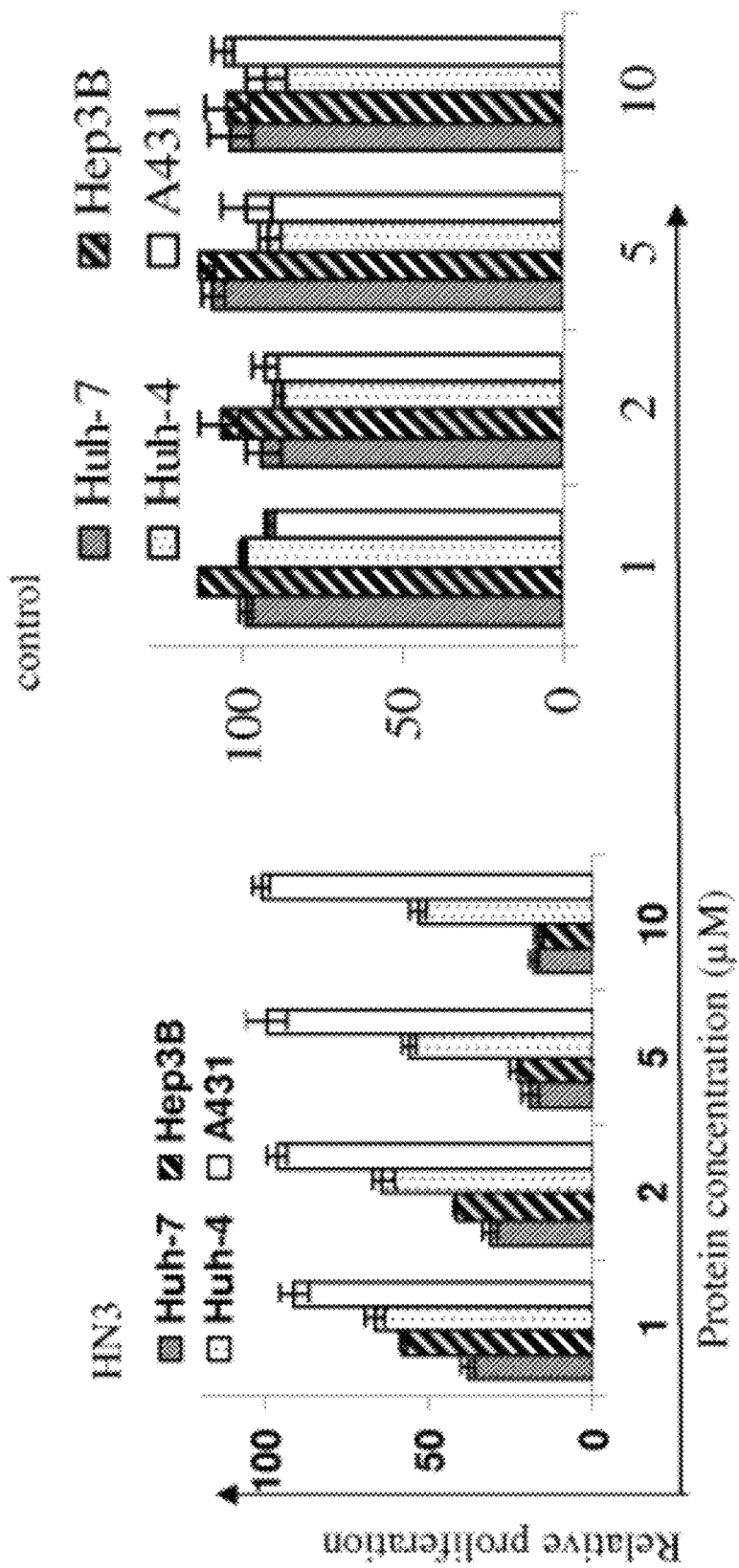

To determine whether HN3 could directly inhibit HCC proliferation by neutralizing GPC3 proliferative effects, cell growth inhibition assays were performed on five GPC3-positive HCC cell lines and one GPC3-negative epithelial cancer cell line (A431). It was found that HN3 strongly inhibited the growth of Hep3B and Huh-7 cell lines with an $IC_{50}$ of ~50 µg/ml, and partially inhibited HepG2, Huh-4 and Huh1 cell growth (FIG. 6D). HN3 did not inhibit A431 cells and other GPC3-negative cells. Other anti-GPC3 human and mouse mAbs in the lab were tested and none of them could inhibit HCC cell proliferation, indicating the epitope recognized by the HN3 human mAb was a novel functional domain specifically involved in HCC cell proliferation.

Figure 7B:
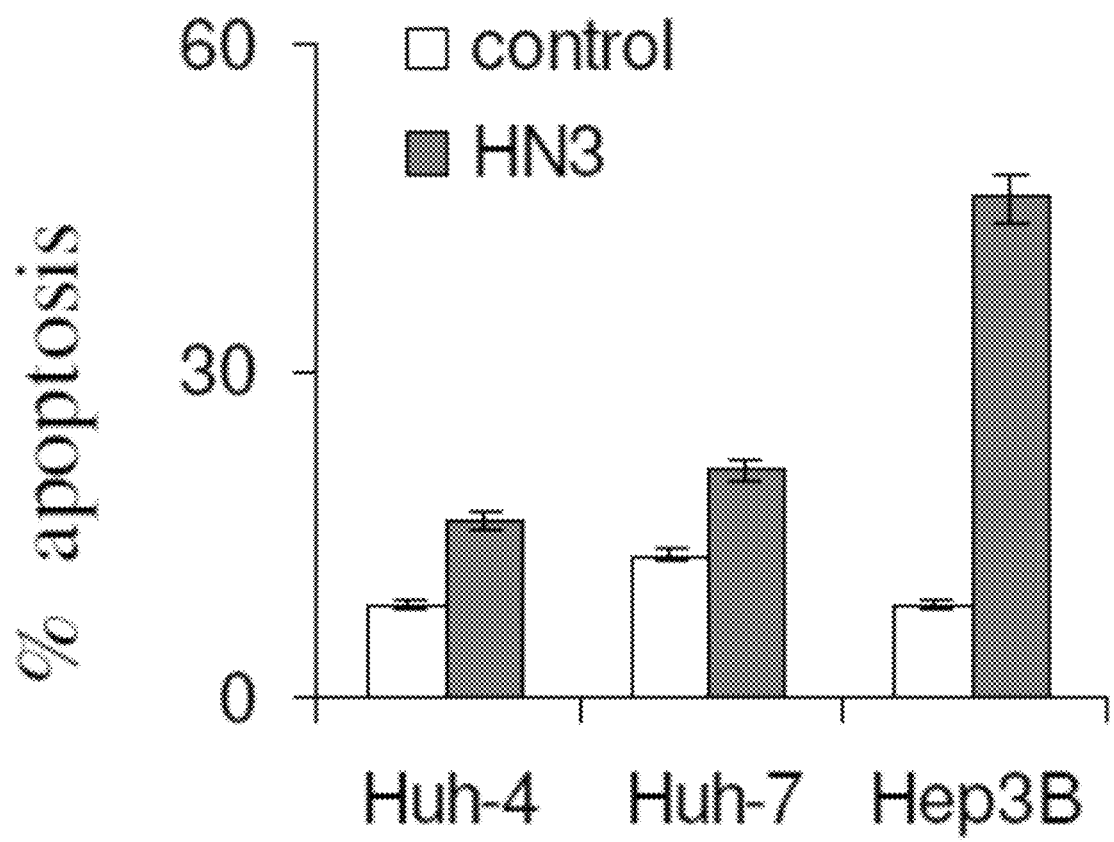
Figure 7C:
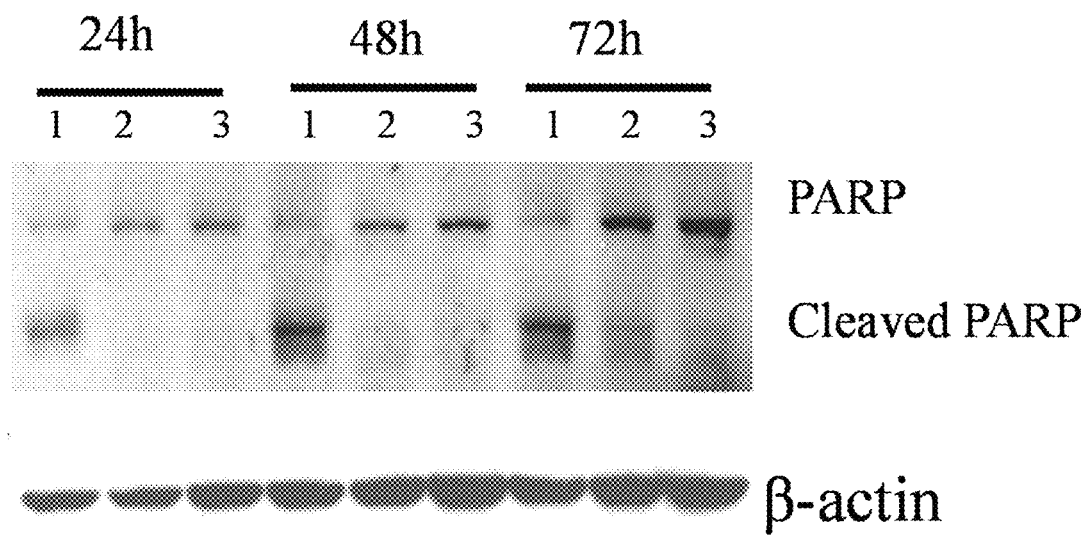

To study the mechanisms underlying the inhibition of HCC cell proliferation by the HN3 human antibody, cell cycle and apoptosis were analyzed. In Huh4 and Huh7, HN3 treatment significantly increased the G1 population, and decreased the S phase (FIG. 7A). Apoptosis was also examined in HN3-treated HCC cells. The induction of apoptosis was observed in HN3-treated Huh-4, Huh-7 and Hep3B cells (FIG. 7B). Cleavage of apoptotic marker PARP was observed after 48 h treatment of the HN3 human mAb (FIG. 7C).

Hippo/Yap, TGFβ and Wnt signaling pathways were further investigated because these three pathways have been suggested to play important roles in HCC pathogenesis, particularly cell proliferation and survival. It was found that target genes of Wnt and TGF signaling did not change, indicating these two pathways might not be involved in the HN3-induced cell cycle arrest and apoptosis. However, Yap may be involved in the mechanism underlying cell proliferation inhibition by the HN3 human mAb.

Figure 7D:
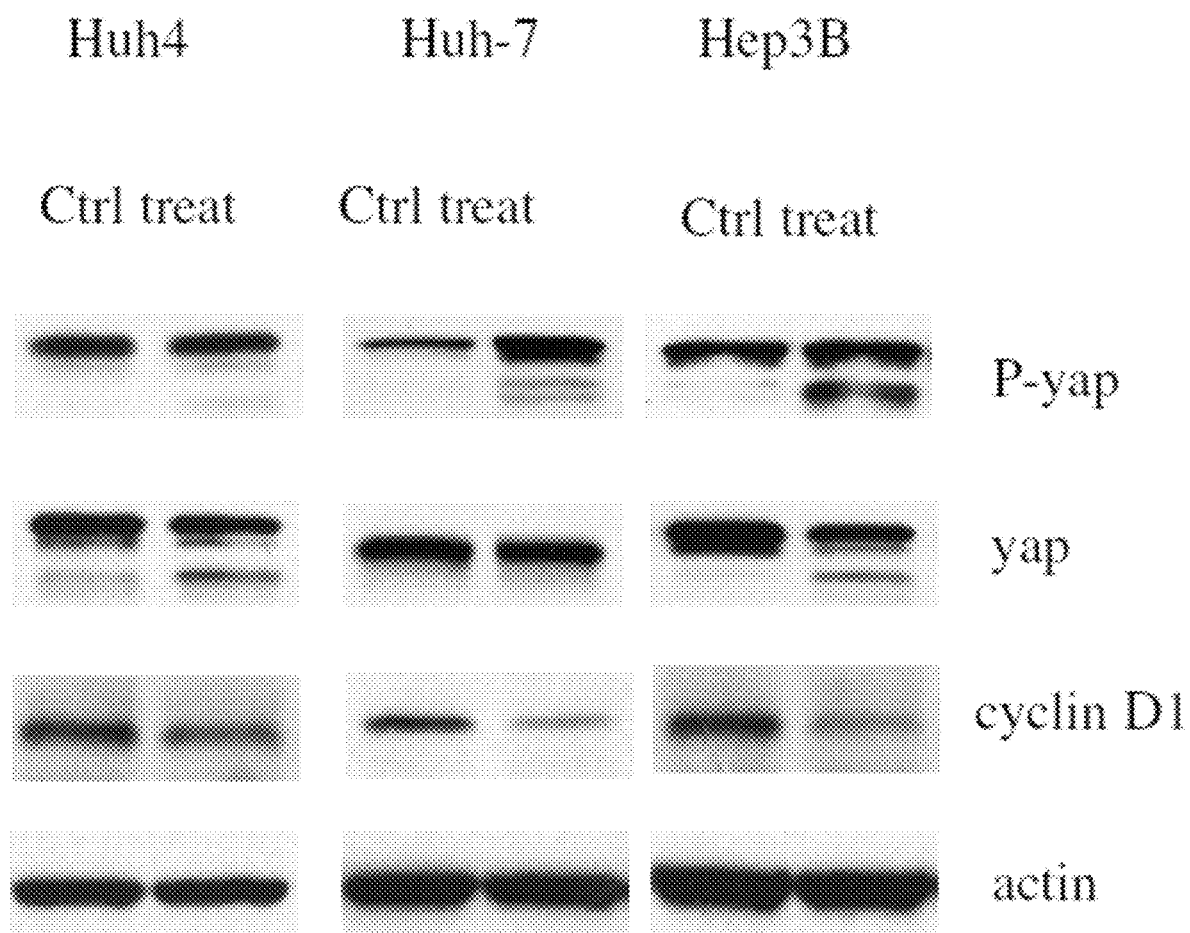

It was recently recognized that hippo pathway actively controls liver size from over growth. Deregulation of hippo pathway was frequently seen in HCC, as resulting from constitutively active yap, the major downstream effector of hippo pathway. To detect the possibility that HN3 inhibits cell proliferation through inactivating yap, molecular changes were measured in a panel of three HCC cell lines (Huh-4, Huh-7 and Hep3B) after HN3 treatment by western blot (FIG. 7D). It was found that yap was inactivated because of the increase of phosphorylated yap and degradation. The total yap was also decreased in treated Hep3B. Consistent with yap inactivation, the yap target gene, cyclin D1, the gene involved in G1 arrest, was also decreased. These observations indicate yap may mediate HN3 function.

C. Discussion

Disclosed herein is the isolation of HN3, a human single-domain mAb targeting GPC3, by phage display. HN3 reacts strongly and specifically to a novel conformation-sensitive epitope of GPC3 on cancer cells with sub nanomolar binding affinity. The binding is independent of the HS chains on GPC3. Furthermore, HN3 can directly inhibit HCC cell proliferation in vitro. The present disclosure is the first report of a human mAb against GPC3 and shows for the first time that drugs targeting GPC3 can inhibit HCC growth.

Antibody-based therapy targeting GPC3 has recently been explored. The mouse mAb GC33 which recognizes a C terminal peptide has been made and humanized GC33 is currently being evaluated in clinical trials for liver cancer therapy. HN3 has at least three advantages over GC33. First, HN3 is a fully human protein. Immunotherapy targeted against GPC3-expressing cancers cannot be fully exploited without a human mAb with high affinity against GPC3 on cancer cells. Second, HN3 is a single-domain antibody. Single-domain mAbs have several advantages over conventional IgG antibodies: (a) better penetration in solid tumors due to its small size (~15 kDa), (b) relative ease and reduced cost of production in E. coli, yeast, or even plants, and (c) the potential to be more feasible in bispecific antibodies, immunotoxins, immunoconjugates, engineered cytotoxic T cells, and nanoparticles. Third, HN3 binds cell surface-associated GPC3 with sub-nanomolar affinity and directly inhibits HCC cell proliferation. The results disclosed herein demonstrate that HN3 can be used as a therapeutic agent for the treatment of liver cancer.

HN3 does not bind to denatured full-length GPC3, but it binds cell-surface associated GPC3 molecules with high affinity. These findings strongly suggest that HN3 recognizes a specific conformation-sensitive epitope structure present in the native form of GPC3 on cells.

HN3 can also be used for diagnostics of HCC by ELISA, immunohistochemistry, and tumor imaging. Filmus and colleagues developed the 1G12 mAb specific for the C terminus of GPC3 and established an ELISA method to measure serum GPC3 in HCC patients (Capurro et al., *Gastroenterology* 125:89-97, 2003). They found GPC3 was significantly increased in the serum of 53% of patients with HCC but undetectable in healthy donors and patients with hepatitis. Hippo et al. developed mAbs specific for the N terminus (residues: 25-358) of GPC3 and found GPC3 was significantly increased in the serum of 51% of HCC patients (Hippo et al., *Cancer Res* 64:2418-2423, 2004).

The present disclosure describes the generation and characterization of a high-affinity single-domain mAb against tumor-associated GPC3. Because HN3 is entirely of human origin and has high affinity, it is expected to be much less immunogenic than murine mAb and to be efficient in targeting GPC3-expressing tumors. HN3 is the first GPC3 binder that shows direct inhibition of HCC growth. Consequently, HN3 is a viable therapeutic reagent for the treatment of liver cancer.

Example 2: HS20—a Human Monoclonal Antibody that Binds the Heparan Sulfate Chains on GPC3 and Inhibits Hepatocellular Carcinoma Cell Migration This example describes the generation and characterization of a human mAb that binds heparin sulfate on GPC3.

A. Materials and Methods

Cell Lines

A panel of six human HCC cell lines (SK-Hep1, HepG2, Hep3B, Huh-1, Huh-4, and Huh-7) was obtained from the National Cancer Institute (NCI) Laboratory of Human Carcinogenesis, Bethesda, Md. A431 (human epithelial carcinoma cell line) was obtained from American Type Culture Collection (ATCC; Manassas, Va.). The cell lines were cultured in RPMI or DMEM supplemented with 10% fetal bovine serum, 100 U/mL penicillin, 0.1 mg/mL streptomycin, and 2 mmol/L L-glutamine. Cells were harvested and the media was changed twice a week. Cells were confirmed to be negative for *mycoplasma*.

Generation of a Human Cell Stably Expressing GPC3

A431 cells were transfected with the pReceiver vector containing a full-length GPC3 cDNA (Genecopia, Rockville, Md.) using LIPOFECTAMINE™ 2000 (Invitrogen, Carlsbad, Calif.). Cell line G1, which highly expresses GPC3, was obtained by single cell sorting with a FACSVantage SE (BD Biosciences, San Jose, Calif.). Briefly, the GPC3 cDNA was transfected into A431 cells. After 3 days, the GPC3 harboring cells were selected by neomycin for 10 days. In a standard protocol for flow cytometric analysis, neomycin-selected cells were incubated with 1 μg/ml of a mouse anti-GPC3 antibody (IG12) (Santa Cruz Biotechnology, Inc. Santa Cruz, Calif.) in DMEM. After incubation for 1 hour at 4° C., the cells were washed once with DMEM and incubated with 1:200 dilution of PE-labeled goat anti-mouse IgG (Invitrogen, Carlsbad, Calif.) for 1 hour. After washing twice, the cells were suspended in 0.5 ml of DMEM, and the top 0.1% GPC3-positive cells were sorted and individual cells were growth in separate wells. The G1 clone had the highest GPC3 protein expression on the cell surface.

Production of Recombinant Human GPC3 Proteins

Four different kinds of recombinant GPC3 were made in various mammalian cells, including HEK-293T, HEK-293F and CHO cells. Primers for rabbit Fc (rFc)-GPC3-his were designed to incorporate flanking EcoRI and NotI restriction enzyme sites to facilitate in-frame cloning into a modified pSecTag2 vector (Invitrogen, Carlsbad, Calif.). Constructs contained an Ig-κ leader sequence followed by the rabbit IgG Fc and the full-length sequence of the extracellular domain of human GPC3 and a His6 tag. The human GPC3 with His tag (named GPC3-his) and two human Fc fusion clones (GPC3-hFc and GPC3(AA)-hFc) were constructed in the pVRC vector containing the IL-2 signal sequence at the N-terminus. GPC3-hFc (AA) was a mutant without the HS chains by replacement of Ser495 and Ser509 with Alanine. The plasmids for rFc-GPC3 and GPC3-his were produced in CHO and HEK-293T cells, respectively. GPC3-hFc and GPC3-hFc (AA) were made in HEK-293F cells. The proteins were harvested from the culture supernatant and purified with a Nickel column (GE Healthcare, Piscataway, N.J.). GPC3-hFc and GPC3(AA)-hFc were purified with a protein A column. The purified recombinant GPC3 proteins were analyzed with ELISA using the 1G12 mouse anti-GPC3 antibody.

Selection of Phage Antibodies

The Tomlinson I and J phage display libraries (Genservice Ltd., Cambridge, UK) used in this study have the size of $1 \times 10^8$ diversity (de Wildt et al., *Nat Biotechnol* 18(9):989-994, 2000). Phage were subjected to three rounds of panning on Nunc immuno plate (Maxisorp, Thermo Fisher Scientific, Rochester, N.Y.) according to an established protocol. The phage display libraries are based on a single human framework for VH (V3-23/DP-47 and JH4b) and Vκ (012/02/DPK9 and Jκ1) with side chain diversity (NNK encoded) incorporated in complementary determining regions (CDRs) 2 and 3 at positions in the antigen binding site that make contacts antigen in known structures and are highly diverse in the mature repertoire (18 different amino acid). An immuno plate (Maxisorb, Nunc/Thermo Fisher Scientific, Rochester, N.Y.) was coated with the GPC3-his protein overnight at 4° C. using 100 μl of 100 μg/ml protein in phosphate buffered saline (PBS) (10 mM phosphate/150 mM NaCl, pH 7.4) for three rounds of panning. The plate was blocked with 3% skimmed milk in PBS (MPBS) for 1 hour at room temperature and $10^{12}$ cfu of phage were pre-blocked by 3% skimmed milk in PBS for 1 hour at room temperature before adding into the immune plate. After 2 hours of incubation at room temperature, the unbound bound phage were removed using 10 washes with PBS/0.1% Tween-20 and 10 washes with PBS. The specifically bound phage were eluted two times with 120 μl elution buffer (100 mM HCl, adjusted to pH 2.2 with solid glycine and containing 0.1% BSA) for 5 minutes at room temperature. The eluted phage were combined, neutralized with 200 μl of 1M Tris (pH 8.0), and used to infect freshly prepared 5 ml of *E. coli* TG1 cells. The phage were amplified and rescued for the next round of panning. The eluted phages obtained from each round of panning were used for tittering for consideration of enrichment.

Phage ELISA

Phage binding was characterized at the end of each round of panning as populations ("polyclonal phage ELISA") and individual clones ("monoclonal phage-ELISA"). Ninety-six randomly picked phage clones at the end of each round of panning were analyzed for GPC3 binding. A MaxiSorp 96-well plate was coated with 50 μl/well of 1 μg/ml of recombinant GPC3 overnight at 4° C. Wells were washed 3 times with PBS and blocked with MPBS for 1 hour at 37° C. Samples (50 μl/well) were pre-incubated with 6% MPBS equal volume of MPBS, and the plate was incubated for 1 hour at room temperature. After washing 3 times with PBS-T, 100 μl of anti-M13-HRP (1:5000 dilution; GE Healthcare, Piscataway, N.J.) was added to each well, and the plate was incubated for 1 hour at room temperature. After washing 3 times with PBS-T, 50 μl/well 3,3',5,5'-tetramethylbenzidine detection reagent (KPL, Gaithersburg, Md.) was added, and the plate was incubated for 10 minutes at room temperature and absorbance was read at 450 nm with a SPECTRAMAX™ Plus plate reader (Molecular Devices, Sunnyvale, Calif.).

Sequence Analysis

For analysis of Ig variable region, phagemid clones were sequenced using primers VH-R for heavy chain (CGAC-CCGCCACCGCCGCTG; SEQ ID NO: 21) and Vk-R for light chain (CTATGCGGCCCCATTCA; SEQ ID NO: 22). CDR3 was determined by comparison with human Ig genes using IMGT/V-QUEST in the International Immunogenetics Database.

Construction of the HS Human IgG

PCR Primers for heavy chain (VH) were used by flanking EcoRI contained IL-8 signal sequence and NheI restriction enzyme sites. The PCR product was inserted at the EcoRI and NheI sites of the expression vector pFUSE-CHIg-HG1 (Invivogen, San Diego, Calif.) and named pMH144. The VL region was PCR amplified using the forward primer contained IL-8 signal sequence and AgeI restriction enzyme site and reverse primer contained NcoI restriction enzyme site. The PCR product was inserted into the AgeI and NcoI sites in the expression vector pFUSE2-CLIg-hk (Invivogen, San Diego, Calif.) and named pMH145. Using LIPOFECTAMINE™ 2000, the plasmids were co-transfected transiently into HEK-293T cells (Invitrogen, Carlsbad, Calif.) in DMEM and the supernatant was changed to FreeStyle serum-free medium (Invitrogen, Carlsbad, Calif.) to eliminate bovine IgG in the purification step. After three days, the medium was collected after centrifugation, replaced for an additional 3-4 days, and collected again. Pooled supernatants were then processed and antibody was purified using a 1-mL recombinant Protein A Hi-Trap column (GE Healthcare, Piscataway, N.J.). The quality and quantity of purified IgG1 was determined by SDS-PAGE and A280 absorbance on a NANODROP™ spectrophotometer (Thermo Scientific/Nanodrop, Wilmington, Del.). The HS20 IgG was analyzed by ELISA on GPC3-his.

Western Blot Assay

Reactivity of HS20 to GPC3 was assessed by immunoblotting. The cell lysates of G1, A431 and HepG2 cells were loaded into 4-20% SDS-PAGE gels for electrophoresis. Proteins were transferred to Hybond-P PDVF membrane (GE Healthcare, Piscataway, N.J.). The membrane was blocked with 5% skim milk in PBS-T for 1 hour at room temperature and washed 4 times with PBS-T. After blocking the PVDF membrane, the membrane was incubated with HS20 (1 µg/ml) for 2 hours at room temperature. The membrane was washed 4 times with PBS-T and incubated with 1:5000 diluted HRP-conjugated anti-human IgG for 2 hours. Signals were visualized by using the Enhanced Chemiluminescence Kit (GE Healthcare, Piscataway, N.J.).

Flow Cytometry

To determine binding of HS20 to cell surface-associated GPC3 proteins, cancer cells (G1, A431 and HepG2 cells) were incubated with HS20 in fluorescence-activated cell sorting (FACS) buffer (5% BSA, 0.01% NaN3) for 1 hour on ice. Bound antibodies were detected by incubating with a 1:200 dilution of goat anti-human IgG-PE (Invitrogen, Carlsbad, Calif.) secondary antibody in FACS buffer for 0.5 hour on ice. Cells were analyzed using FACSCalibur (BD Biosciences).

Immunohistochemistry

Formalin-fixed and paraffin-embedded tissue blocks from 10 patients with hepatic cancer were retrieved from the files of the Armed Forces Institute of Pathology. Consecutive sections at 5-7 µm thickness were prepared and placed on positively charged slides. Sections were deparaffinized with three-changes of xylene, and washed with descending concentrations of alcohol and water, and subjected to antigen retrieval following a previously published protocol (Man and Tavassoli, *Appl Immunohistochem* 4:139-141, 1996). Immunostaining was carried out as previously described (Hsiao et al., *J Cancer* 1:93-97, 2010) with HN3, HS20 and an isotype control human IgG (Southern Biotech, Birmingham, Ala.). The secondary antibody conjugated with peroxidase, diaminobenzidine and 3-amino-9-ethylcarbazole chromogen kits were obtained from Vector Laboratories (Burlingame, Calif.). To assess the specificity of the immunostaining, different negative controls were used, including the substitution of the primary antibody with the same isotype or pre-immune serum of the antibody, and omission of the secondary antibody. In addition, the immunostaining procedure was repeated at least twice using the same protocol and under the same conditions. Immunostained sections were independently evaluated by two investigators. A given cell was considered immunoreactive if distinct immunoreactivity was consistently seen in its cytoplasm, membrane, or nucleus, while all negative controls lacked distinct immunostaining.

Cell Morphology and Migration

Cell migration was assessed by wound healing scratch assay and culture insert. Hep3B cells were seeded in wells of a 24-well plate and grown to 100% confluence. A wound was created in the cell monolayer in each well using a sterile P200 micropipette tip. The wells were then washed with 1 ml of growth medium, which was removed and replaced with 0.5 ml of growth medium with various concentration of IgG-20. After 24 hours incubation at 37° C. in a 5% $CO_2$ incubator, each scratch was examined and photographed. For the time course of migration assay, an ibidi culture insert (Applied BioPhysics, Troy, N.Y.) was used in 24-well plates. After growth of cells to 100% confluence, the culture insert was removed and the plate was filled with 0.5 ml of growth media contained HS20 (50 µg/ml). The first image of each scratch was acquired at time zero through a phase contrast microscope at 10× magnification. The 24-well plates were then incubated at 37° C., 5% $CO_2$ for 48 hours and scratches at each time point were examined and photographed at the same location. The images were analyzed using the Tscratch program.

Statistics

The GraphPad Prism program (Graphpad software, San Diego, Calif.) was used to statistically analyze the results. Cell migrations were analyzed by one way analysis of variance with Dunnett's and Newman-Keuls multiple comparison post tests. P-values<0.05 were considered statistically significant.

B. Results

Isolation of the HS20 Fv

Figure 8A:
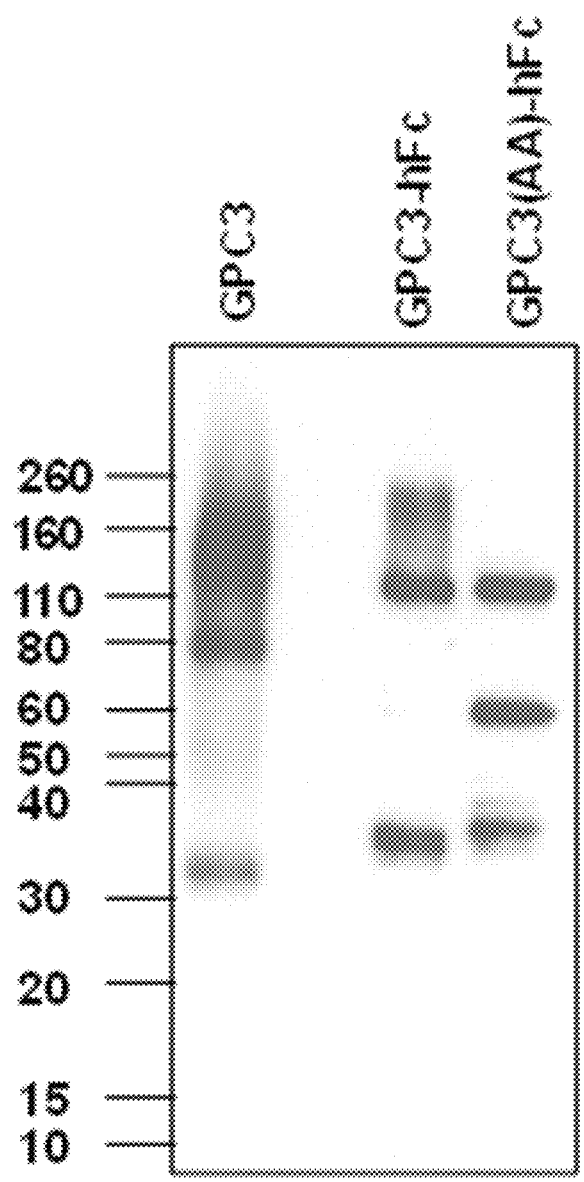
FIG. 8A is a Western blot of purified recombinant GPC3 proteins. GPC3-hFc, GPC3-human Fc fusion; GPC3(AA)-hFc, GPC3-human Fc fusion without the HS chains.
Figure 8B:
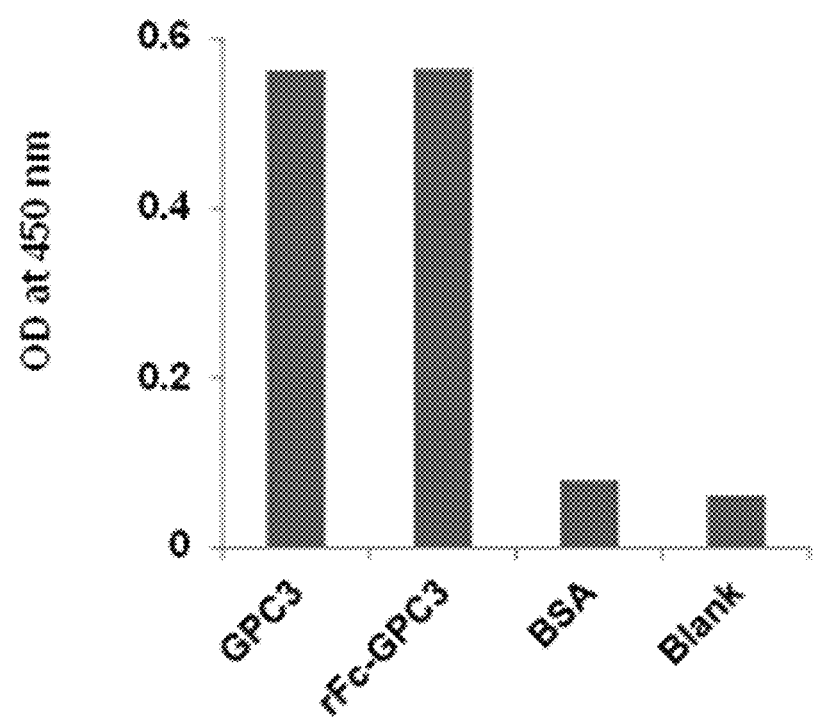
FIG. 8B is a graph showing results of an ELISA. One μg of the purified recombinant proteins were coated on 96-well plates and probed with the 1G12 anti-GPC3 mAb. rFc-GPC3, rabbit Fc-GPC3 fusion.
Figure 9A:
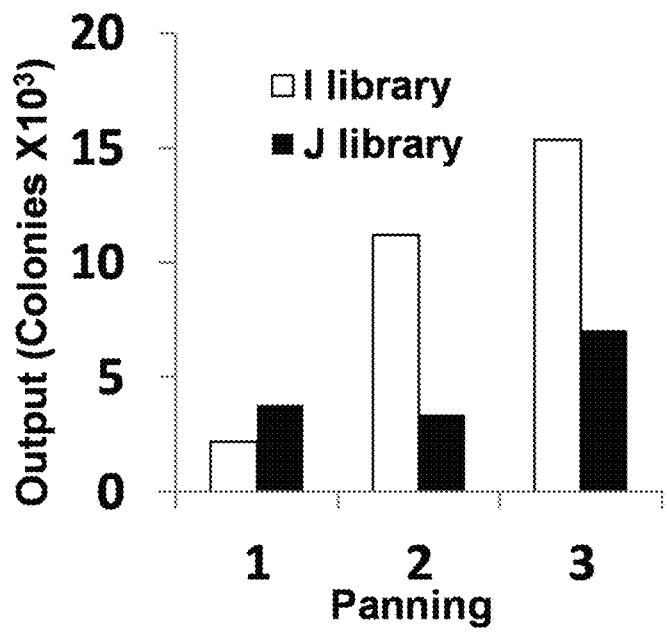
FIGS. 9A and 9B are graphs showing enrichment of phage Fvs against GPC3.
Figure 9B:
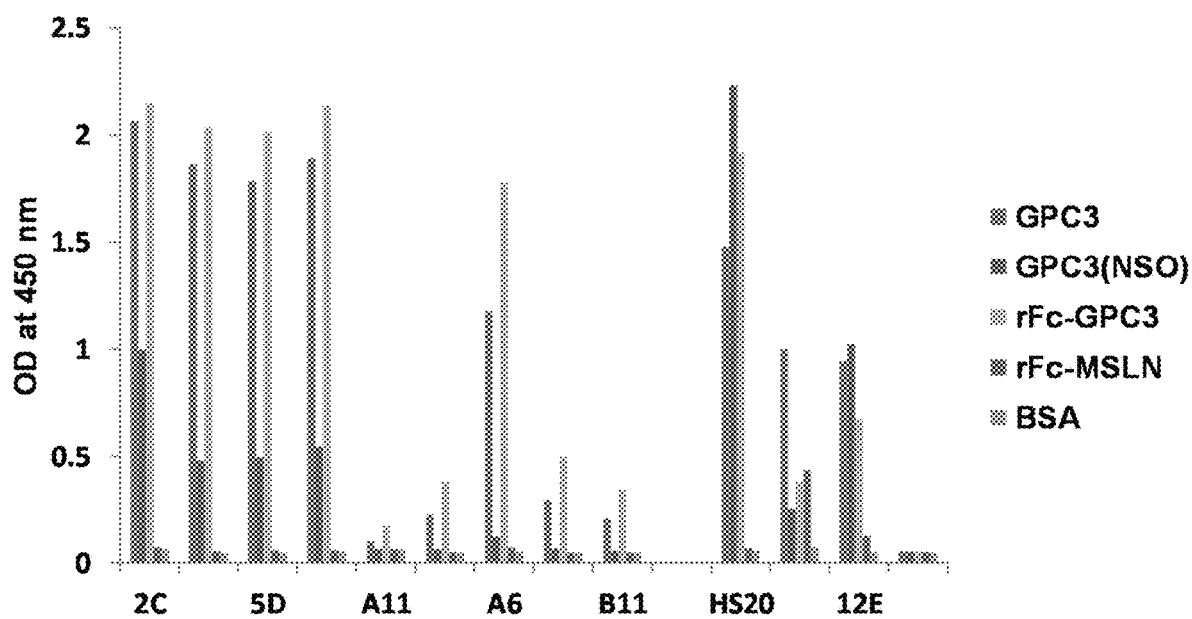

To generate mAbs to GPC3, several recombinant proteins were made in mammalian cells. First, a rabbit IgG Fc-GPC3 fusion protein (rFc-GPC3) was made in CHO cells. Second, GPC3 with a six-histidine tag (GPC3) was expressed in human HEK-293 cells. Third, GPC3-huFc and GPC3(AA)-huFc, two human Fc fusion proteins, were produced in HEK-293 cells. GPC3(AA)-huFc does not contain the HS chains because two serine residues (Ser495 and Ser509) are replaced with two alanine residues. All recombinant proteins were validated by SDS-PAGE followed by Western blot and ELISA using a commercially available mouse anti-GPC3 mAb (clone 1G12) (FIG. 8). Human scFv phage display libraries were screened against 100 µg/mL of recombinant GPC3 coated on MaxiSorp 96-well plates for 3 rounds of panning. After the first round of phage panning, about 4000 individual phage clones were obtained. Polyclonal ELISA of the bound phage was used to monitor the enrichment of high binders after each panning step (FIG. 9A). The gradual enrichment of phage suggests that a small number of high affinity binders existed in the primary libraries I and J and were gradually enriched during the process of panning. At the end of the third round, more than 50% of clones randomly selected were GPC3 binders (FIG. 9B). The clone 20 (named HS20) was chosen for further characterization because it bound all the recombinant GPC3 proteins with strong signals.

Sequence analysis of HS20 showed somatic mutations in heavy (H) chain and light (L) chain CDRs, particularly in HCDR2, HCDR3 and LCDR3 and LCDR3. It may indicate that the key residues for the antigen binding are mostly located in CDR2 and CDR3 in heavy and light chains. Since the Fv was isolated from a synthetic library (de Wildt et al., *Nat Biotechnol* 18(9):989-994, 2000), somatic mutations were not found in the framework regions, outside the CDRs.

After a search of all of the known public databases, it was confirmed that HS20 has a unique Fv sequence. The VH sequence is the closest to the two known VH sequences with known specificities: ABQ50854.1 (a peptide mimotope of the group B *Streptococcus* type III polysaccharide) and ADP21081.1 (canine dendritic cells). The VL sequence is closest to ABD59019.1 (TREM-like transcript-1) and ABQ50855.1 (a peptide mimotope of the group B *Streptococcus* type III polysaccharide). The Fv of HS20 is the most homologous to the Fv known to bind a polysaccharide on *Streptococcus*, which suggested that the HS20 epitope is associated with a carbohydrate site.

Binding Properties of HS20 on Cancer Cells

Figure 11A:
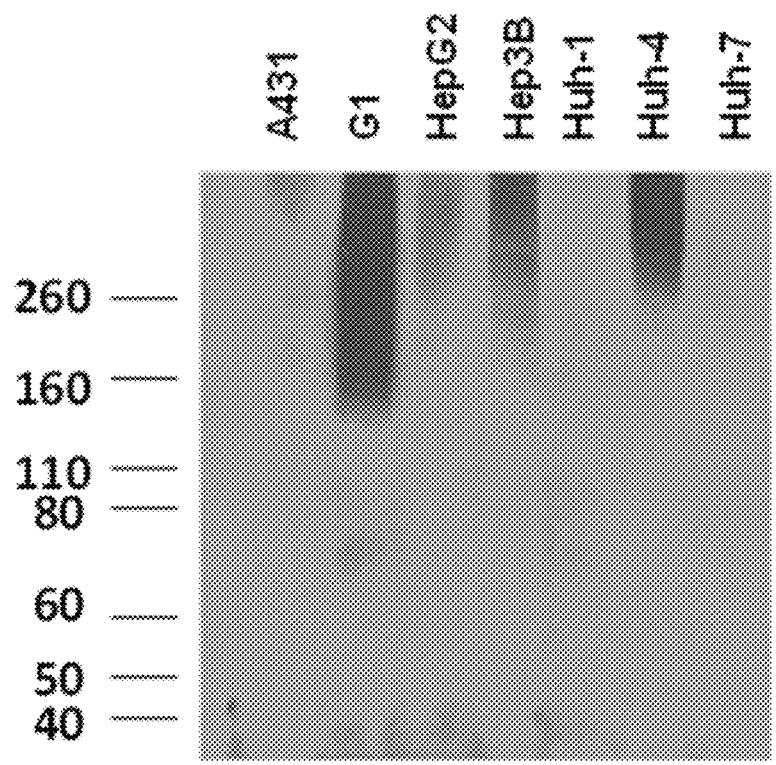
FIG. 11A is a Western blot showing binding of HS20 on recombinant and native GPC3 in cell lysates.
Figure 11B:
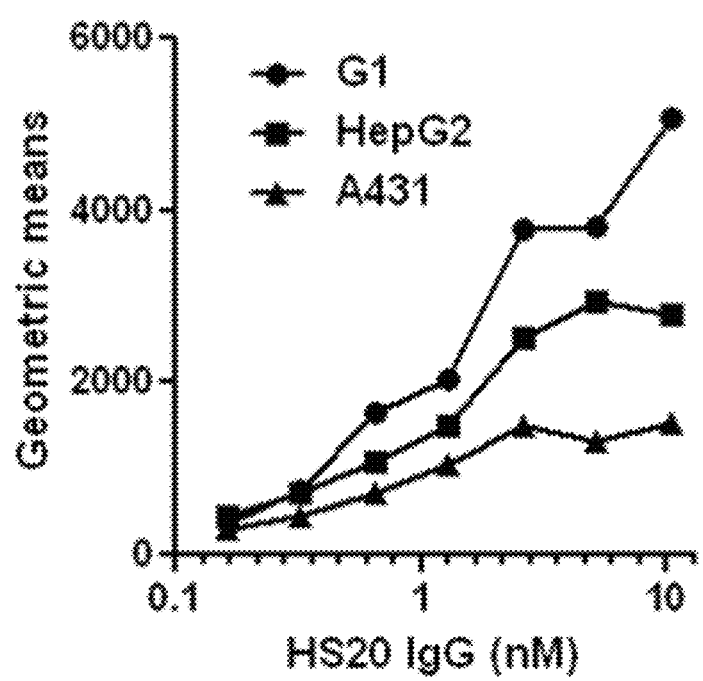
FIG. 11B is a graph showing results of flow cytometric analysis of HS20 on cells. Cells (A431, G1 and HepG2) were probed with HS20 with various concentrations. The binding was visualized with a goat anti-human IgG PE-conjugated secondary antibody by flow cytometry.

To characterize the binding properties of HS20, the HS20 Fv was converted into a human IgG. A human IgG molecule was constructed by fusing the VH with the constant region of heavy chain γ1 and the VL with the constant region of human κ chain. The final human IgG molecule is IgGγ1κ. The cell lysates of A431 (GPC3-), G1 (GPC3+), and a panel of human HCC cell lines (HepG2, Huh-1, Huh-4 and Huh-7) was probed by western blot using the HS20 IgG (FIG. 11A). G1 is the A431 stable line that highly expressing GPC3 on the cell surface. HS20 bound G1 with much stronger signals than A431. The bands in G1 recognized by HS20 formed a large smear, indicating possible heterogeneity of glycosylation patterns. Binding of HS20 was also detected on HepG2, Hep3B and Huh-4, but not Huh-1 and Huh-7. To determine whether HS20 binds cell surface-associated GPC3, flow cytometric analysis was performed (FIG. 10B). HS20 bound G1 and the HepG2 cell line with strong signals. HS20 had relatively weak signals on A431 cells, indicating the binding signals were associated with the GPC3 protein expression at the cell surface.

Figure 12:
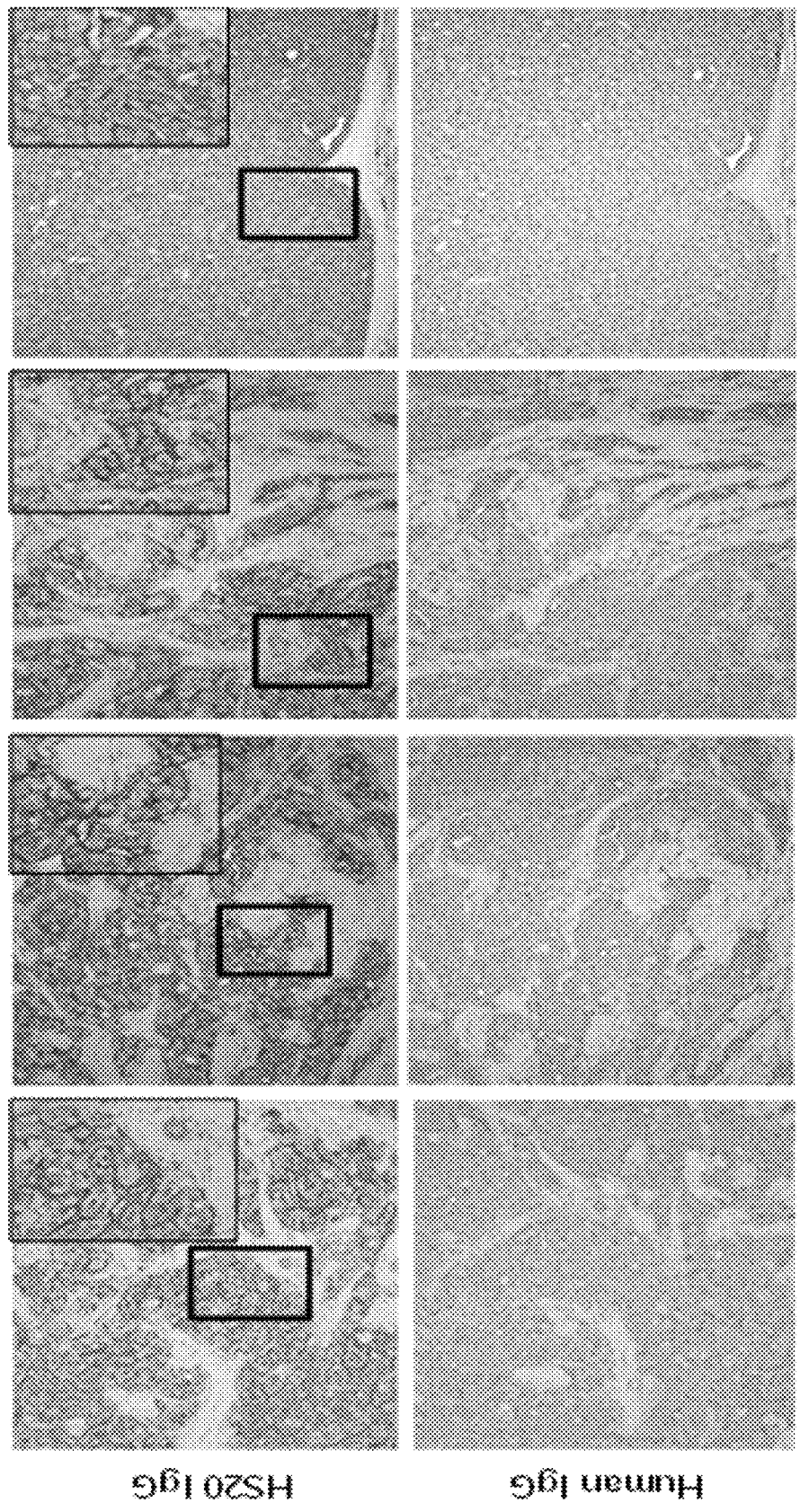
FIG. 12 is a series of images showing immunohistochemical analysis of HS20 in HCC tissues.

To further analyze the binding HS20 on HCC tissues, immunohistochemistry was performed on tumor specimens (FIG. 12). HS20 had a strong and highly specific immunostaining on the plasma membrane of HCC cells but no staining on GPC3-negative cells such as stroma cells.

HS20 Binds a HS Site on GPC3 with Subnanomolar Affinity

Figure 13A:
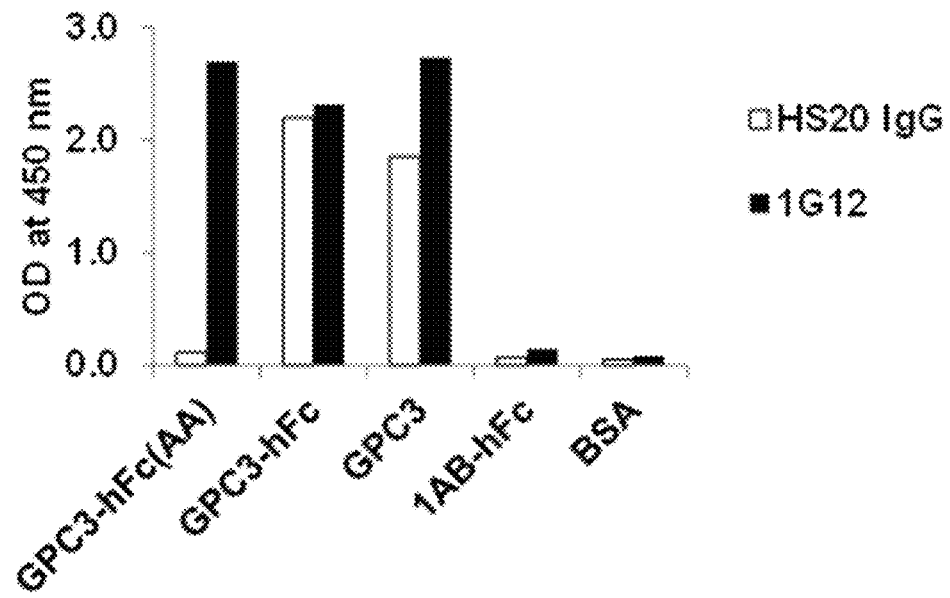
FIGS. 13A-13D are figures showing the binding properties of H520.
Figure 13B:
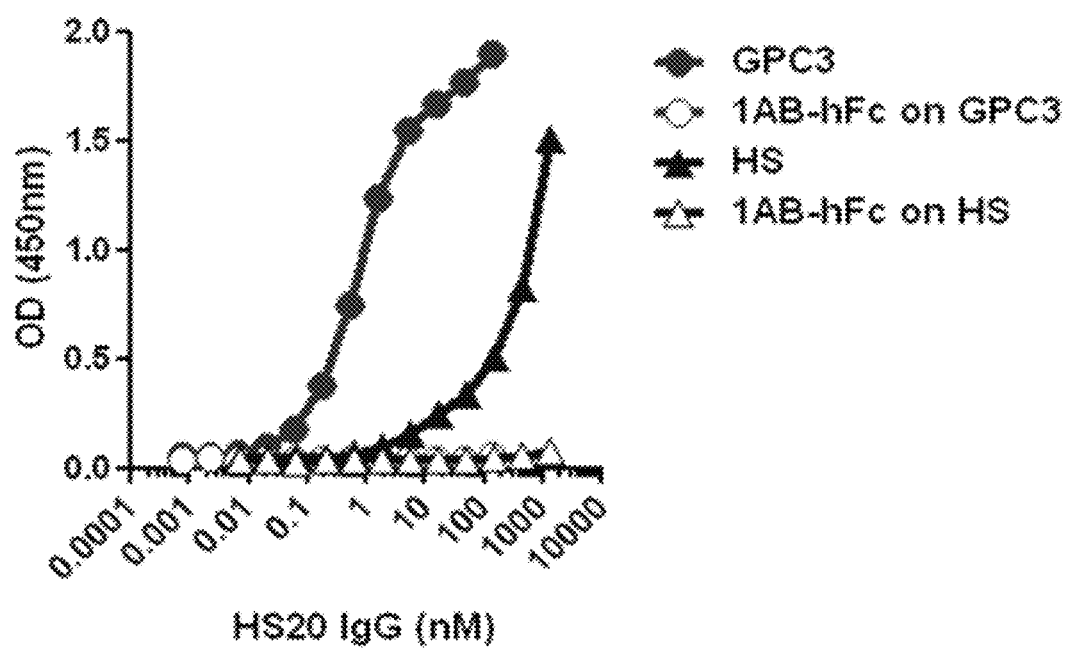

To reveal the binding site of HS20 on GPC3, an ELISA was performed using recombinant GPC3-hFc and mutant GPC3(AA)-hFc (FIG. 13A). The control GPC3 mAb (1G12) bound all recombinant GPC3 proteins, which is consistent with the fact that 1G12 bound the C terminal core protein of GPC3 (Capurro et al., *Gastroenterology* 125:89-97, 2003). HS20 bound GPC3-hFc but not mutant GPC3(AA)-hFc, indicating that HS20 binds to a HS site on GPC3. The binding of HS20 on recombinant GPC3 protein was also compared with binding on HS molecules. HS20 bound at least 1000-fold stronger on GPC3-associated HS than HS alone. This result indicates that HS20 binds HS and such binding may be enhanced by the core protein of GPC3. Based on the ELISA results (FIG. 13B), the binding affinity (equilibrium $K_D$) of HS20 for GPC3 was estimated to be 0.75 nM. The data sets exhibited a strong correlation ($R2=0.997$).

Figure 13C:
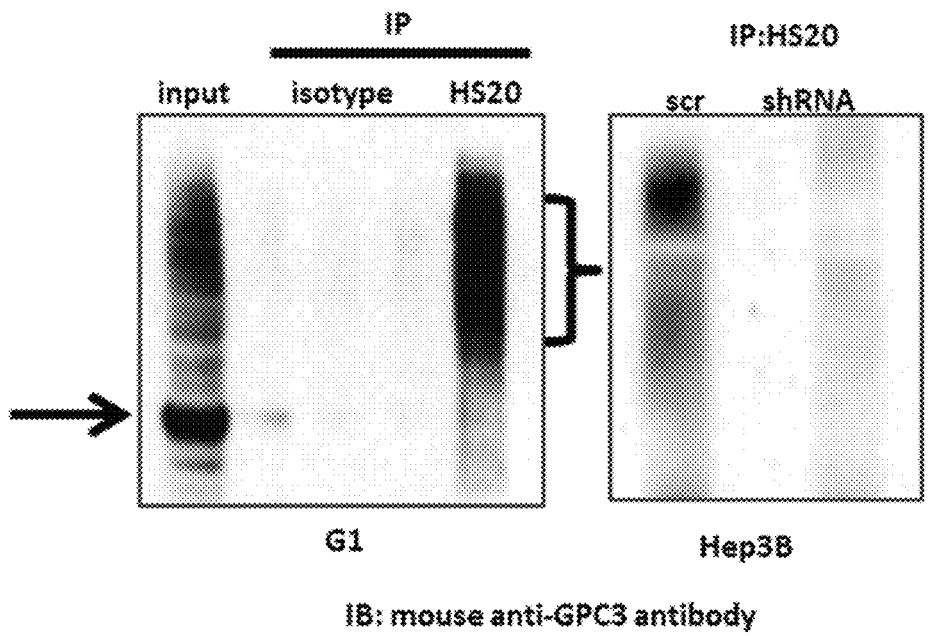

It was also determined that the binding of HS20 was confirmation-dependent. The HS20 human antibody did not bind denatured GPC3 on Western blot using cell lysates; however, it was possible to pull down endogenous GPC3 proteins from G1 cells by HS20 (FIG. 13C). A similar result was also observed in Hep3B cells, a native HCC cell line. It was found that no significant GPC3 protein could be pulled down from GPC3 knock-down Hep3B cells (FIG. 13C, right).

Figure 13D:
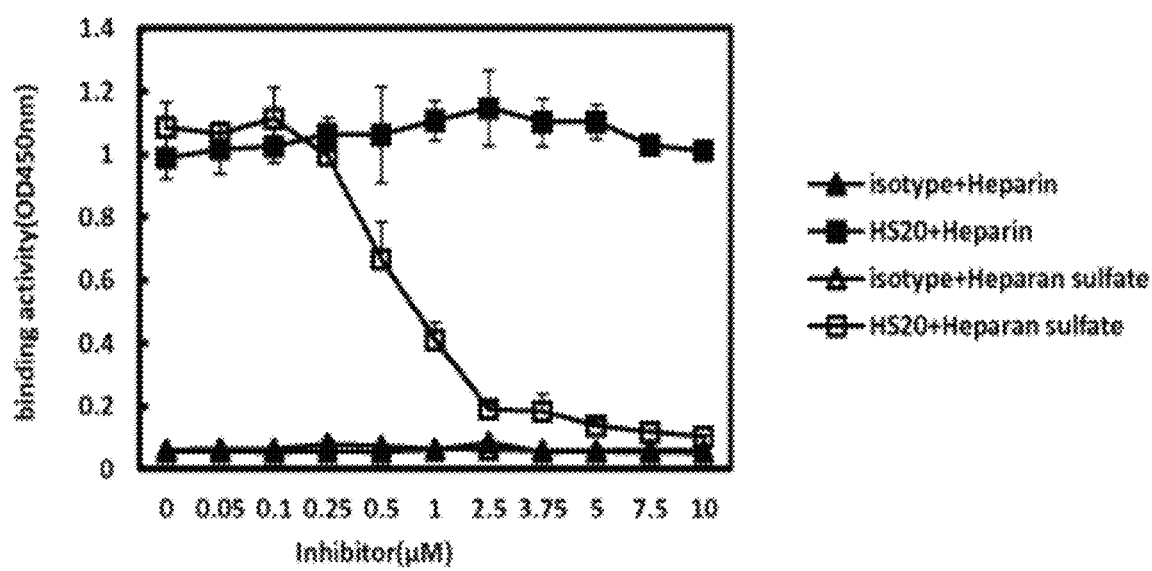

Heparan sulfate belongs to the glycosaminoglycan family and has highly closely related structure to heparin. They both have sulfated repeating disaccharide units. However, recent studies show that the structure of heparan sulfate is very different from heparin. To evaluate the binding properties of HS20, competition ELISA experiments were performed. HS20 was pre-incubated with heparan sulfate (HS) or heparin and it was found that only HS was able to block the HS20-GPC3 binding (FIG. 13D). Collectively, it is believed that the HS20 human antibody (i) dominantly binds the HS chains on GPC3; (ii) excess amounts of heparin molecules or enzymatic digestion of heparinase cannot abolish the binding of the HS20 mAb to GPC3 and (iii) the core protein of GPC3 may play a role in supporting or stabilizing a distinct conformation recognized by the HS20 mAb.

HS20 Inhibits HCC Cell Migration by Disturbing the GPC3 and Wnt3a Interaction

Figure 4B:
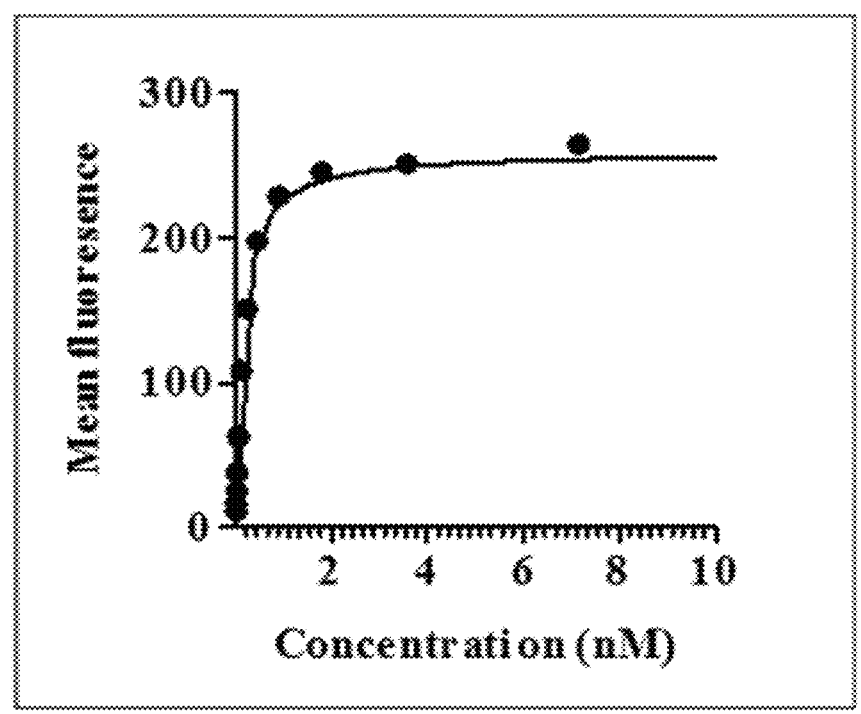
Figure 14A:
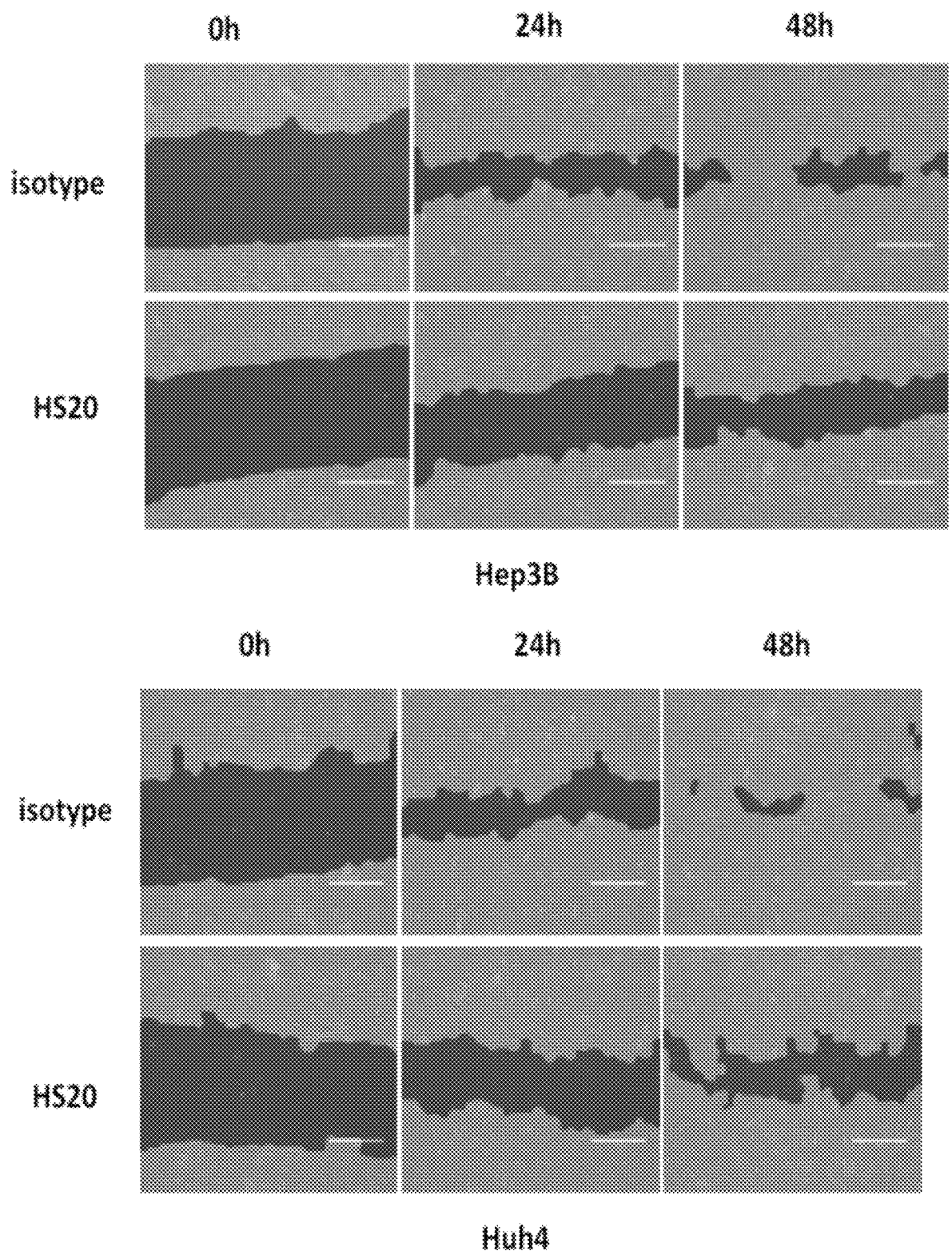
Figure 14B:
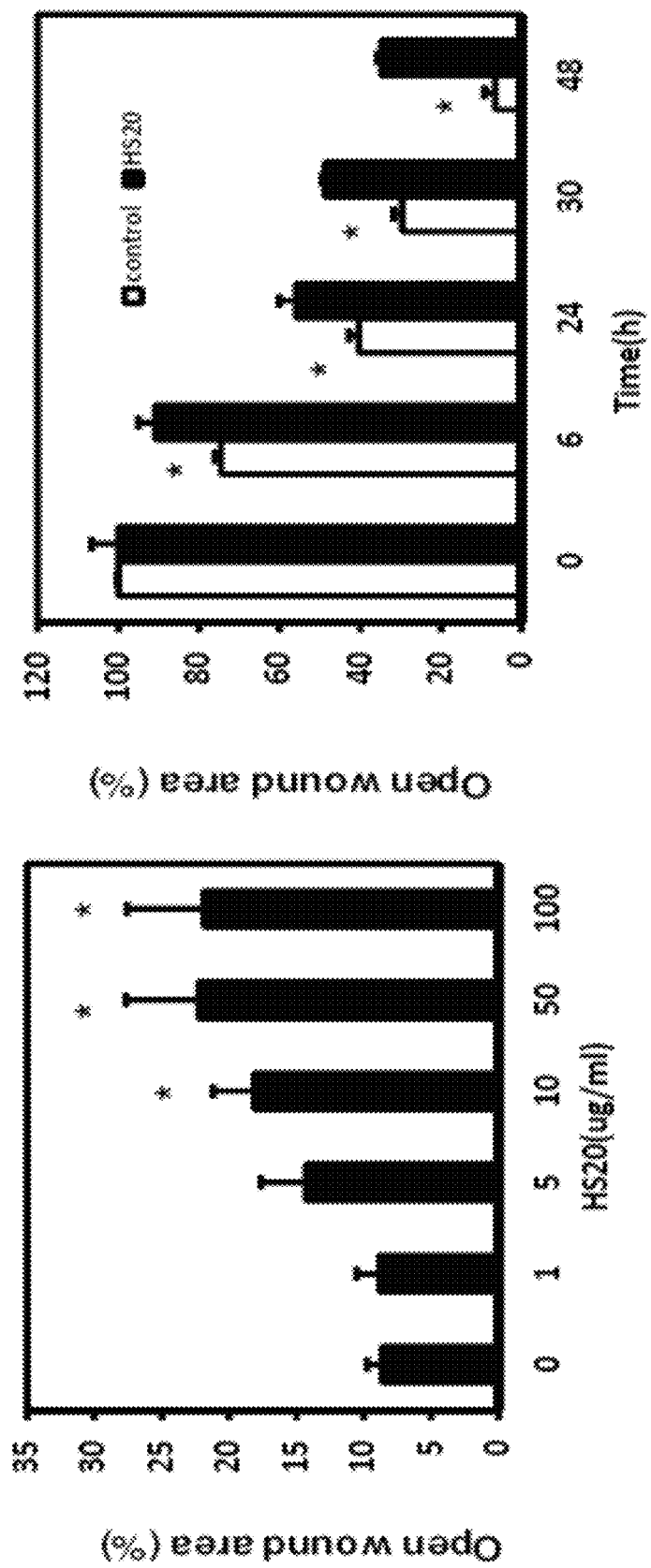
Figure 14C:
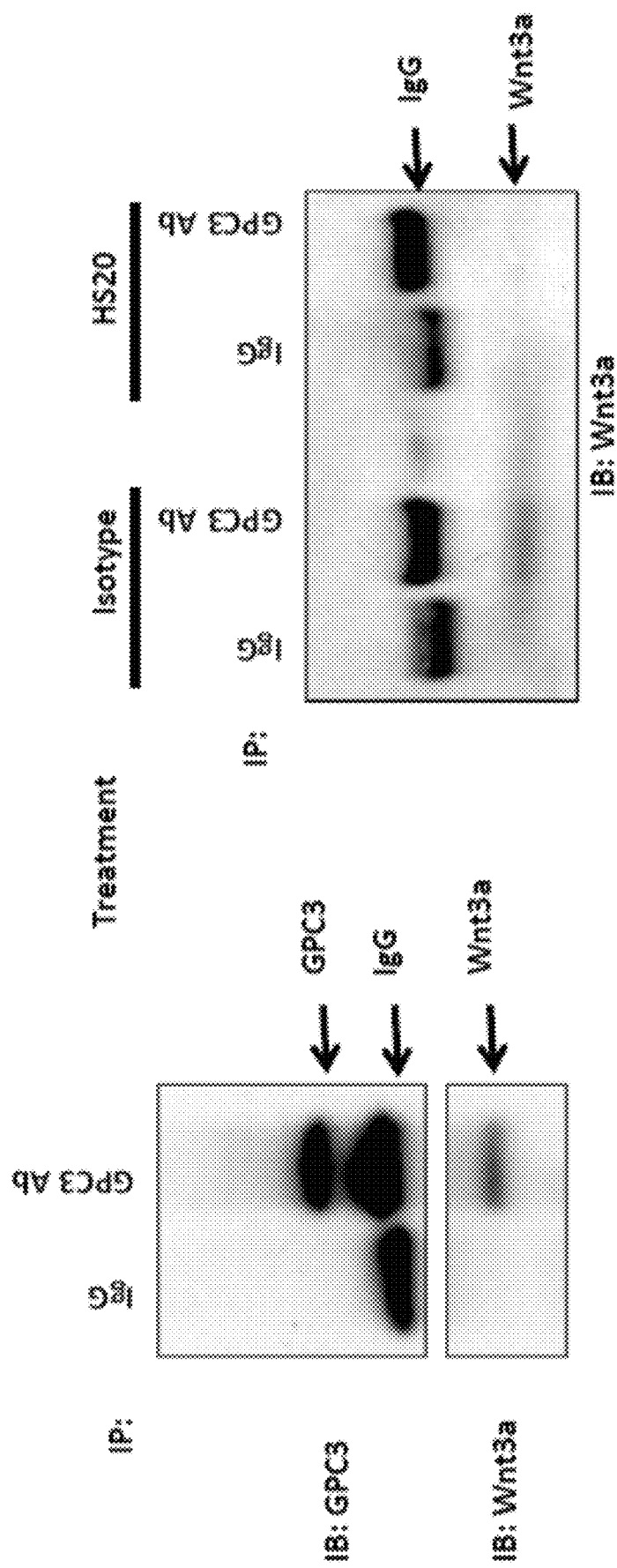
Figure 14D:
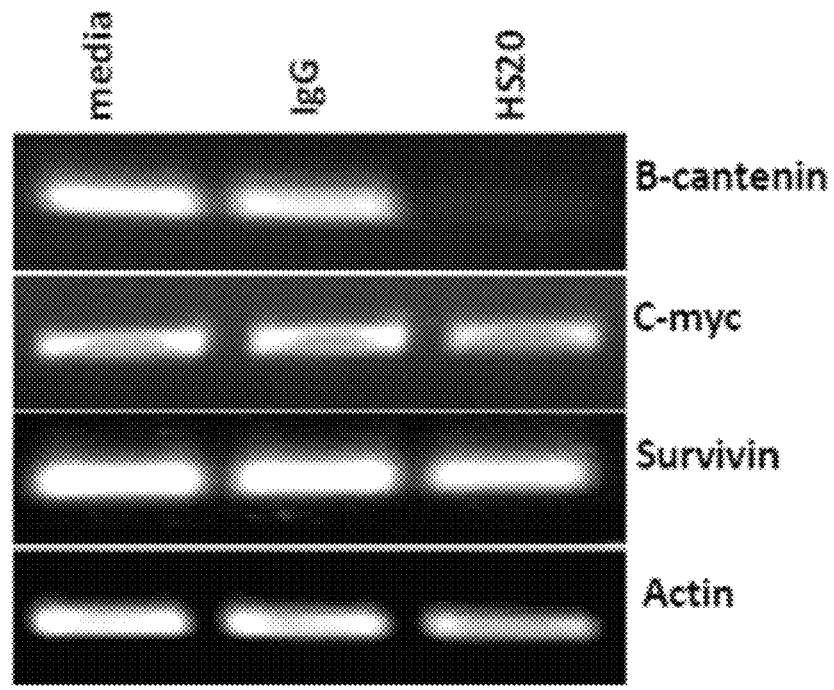
Figure 14E:
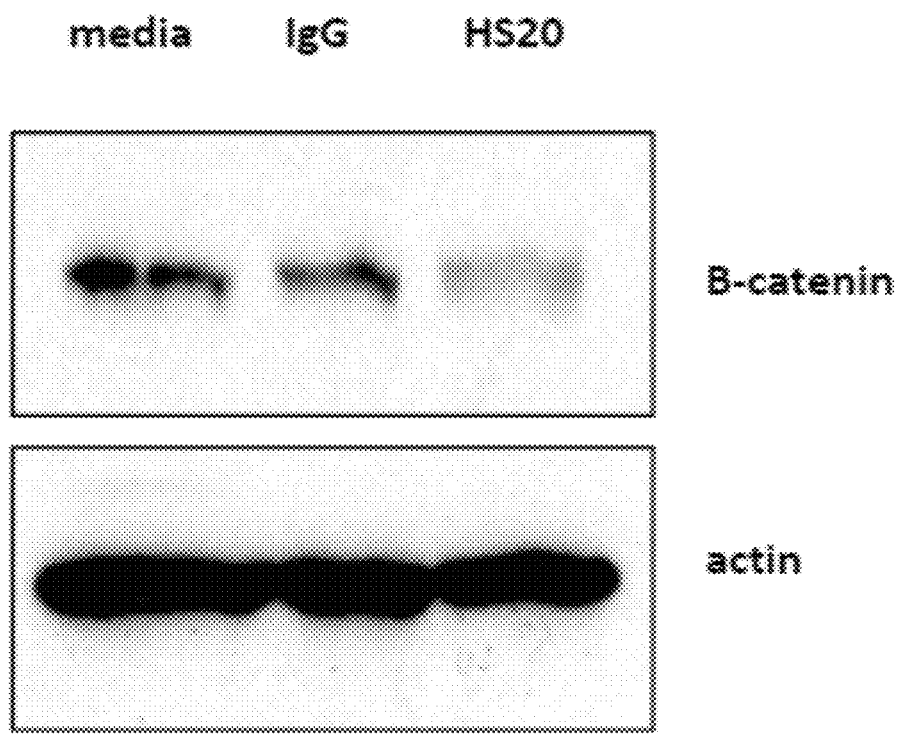

To determine whether HS20 can neutralize the function of GPC3, HCC cells were treated with the HS20 mAb and the HS20 mAb was tested in cell proliferation and cell migration assays. The HS20 human mAb did not inhibit HCC cell proliferation in vitro. However, the cell migration ability of HCC cells was significantly reduced after HS20 treatment. Wound-healing assay indicated that both Hep3B cells and Huh-4 cells showed slower migration, especially 48 hours after HS20 treatment (FIG. 14A). Whereas the migration ability of SK-hep1, which was the GPC3 negative cell line, did not change. The inhibition showed a dose-dependent manner (FIG. 4B left) and significant inhibition was found after 6 hours at 50 µg/ml of HS20. The wound closure efficiency of HS20-treated cells was decreased by more than 30% as compared to the control group (FIG. 4B right).

Wnt signaling has been suggested to play an important role in HCC progression. Previous studies show that Wnt3a may be involved in HCC pathogenesis. GPC3 might work as the storage site for Wnt ligand and make it accessible to its receptor Frizzle. Hep3B cells were treated with the HS20 human mAb and then the interaction of GPC3 and Wnt3a was examined. HS20 blocked the interaction of Wnt3a and GPC3 (FIG. 4C), suggesting that HS20 might block the Wnt signaling by disrupting the interaction of GPC3 and Wnt3a. To further evaluate downstream effects of Wnt signaling, the Wnt targeting genes were evaluated by RT-PCR. The expression of many genes related to cell metastasis or migration decreased whereas those related to cell growth did not change significantly. It was notable that after HS20 treatment, β-catenin expression decreased at both the mRNA level and protein levels (FIGS. 4D and 4E). Taken together, these data indicate that HS20 binding to GPC3 inhibits Wnt signaling, leading to the degradation of β-catenin and finally to the inhibition of HCC cell migration.

C. Discussion

Metastasis resistant to therapy is the major cause of death from cancer. Despite almost 200 years of study, the process of tumor metastasis remains elusive. Stephen Paget initially proposed the "seed and soil" hypothesis which has been supported by numerous experimental reports (Paget, *Lancet* 133:571-573, 1889; Talmadge and Fidler, *Cancer Res* 70(14):5649-5669, 2010). Recent studies have provided the evidence that heparan sulfates play important roles in regulating cell migration in melanoma (Balijinnyam et al., *Am J Physiol Cell Physiol* 297(4):C802-C813, 2009) and breast cancer (Khurana et al., *Cancer Res* 71(6):2152-2161, 2011). In the present study, a human mAb specific for the HS site on GPC3 was developed and this antibody was found to inhibit HCC cell migration.

Cell movement is important pathologically in wound healing and cancer metastasis. In order for these processes to occur, the extracellular matrix (ECM) must be degraded to allow for the free movement of cells (Kim et al., *J Endocrinol* 209(2):139-151, 2011). These processes are accomplished by proteases and the HS-degrading enzyme heparanase. The present disclosure demonstrates that a drug targeting the HS chain on GPC3, a cancer-specific HSPG, can inhibit cancer cell migration.

Example 3: Mutation of HS20 to Remove an N-Glycosylation Site does not Alter Binding Affinity and Specificity This example describes modification of the H220 mAb to remove an N-glycosylation site identified in the VL domain.

Figure 15A:
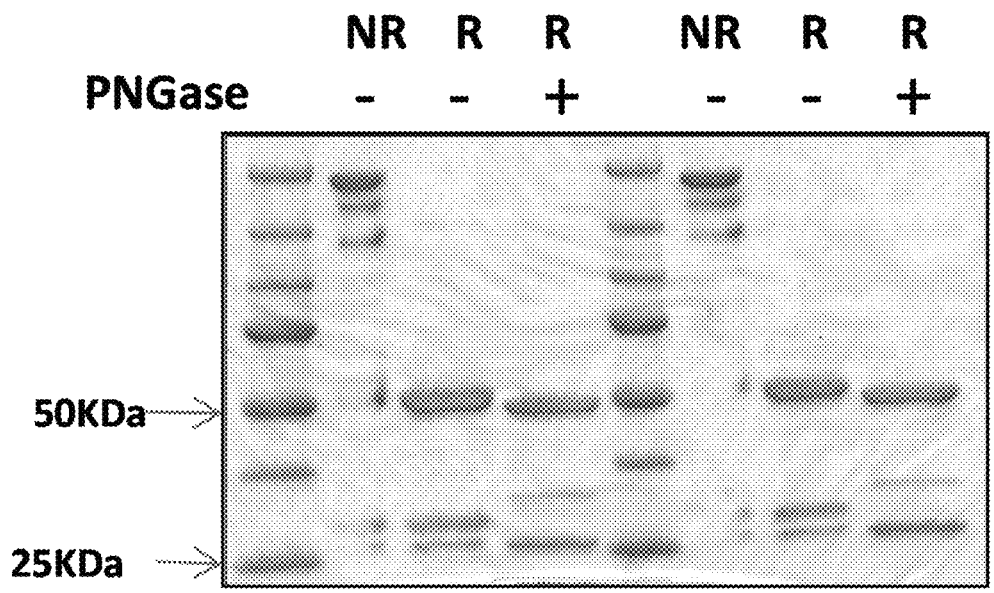
FIG. 15A shows SDS-PAGE of HS20 wild-type (Wt) mAb treated with (+) or without (−) the endoglycosidase PNGase. Five μg of purified protein was used for each sample. NR=non-reduced; R=reduced.
Figure 15B:
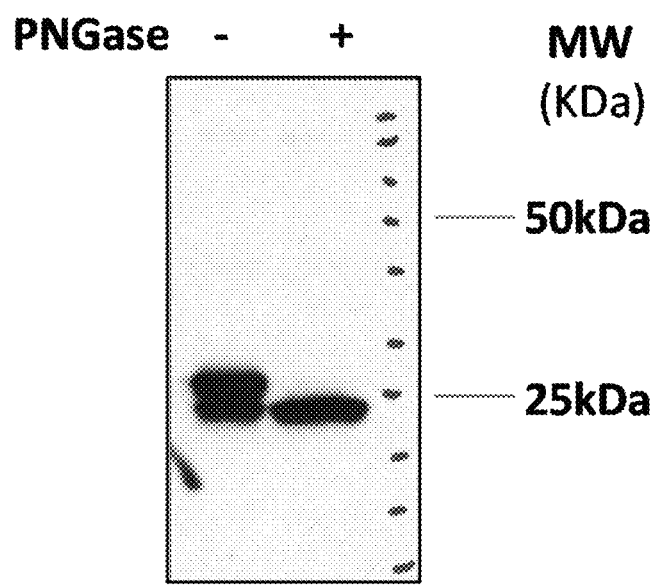
FIG. 15B is a Western blot for HS20 Wt mAb treated with (+) or without (−) PNGase. HS20 light chain was detected using goat anti-human kappa chain antibody.

Two light chains bands were observed in the HS20 IgG expressed in the HEK-293-based mammalian expression system, suggesting the presence of an N-glycosylation site. By analyzing the sequence of the light chain, a potential N-glycosylation site was identified in CDR2 of the VL domain of HS20 (amino acid residue 50 of SEQ ID NO: 16). The presence of the N-glycosylation site produced an extra band of approximately 30 kDa when analyzed by SDS-PAGE; however, a single band was observed when the purified HS20 IgG was treated with the endoglycosidase PNGase to remove all N-glycosylation (FIG. 15A). A Western blot of H250 mAb treated with PNGase also demonstrated a single VL band, while untreated antibody resulted in two bands for the VL domain (FIG. 15B).

Figure 15C:
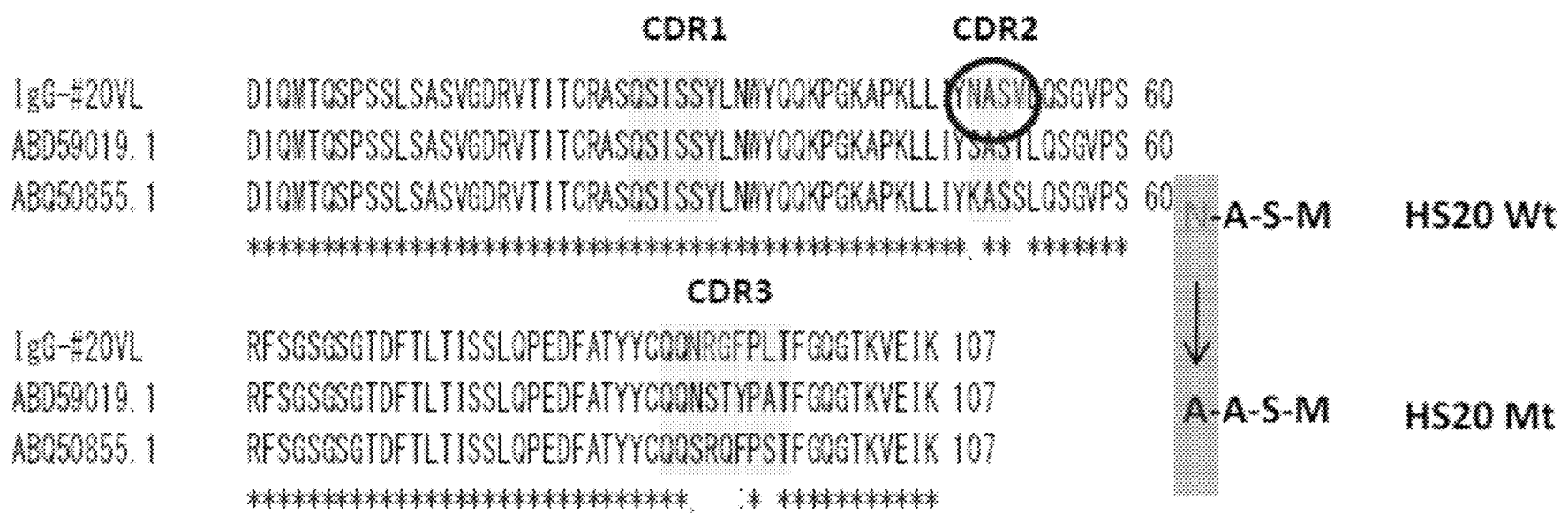
Figure 16A:
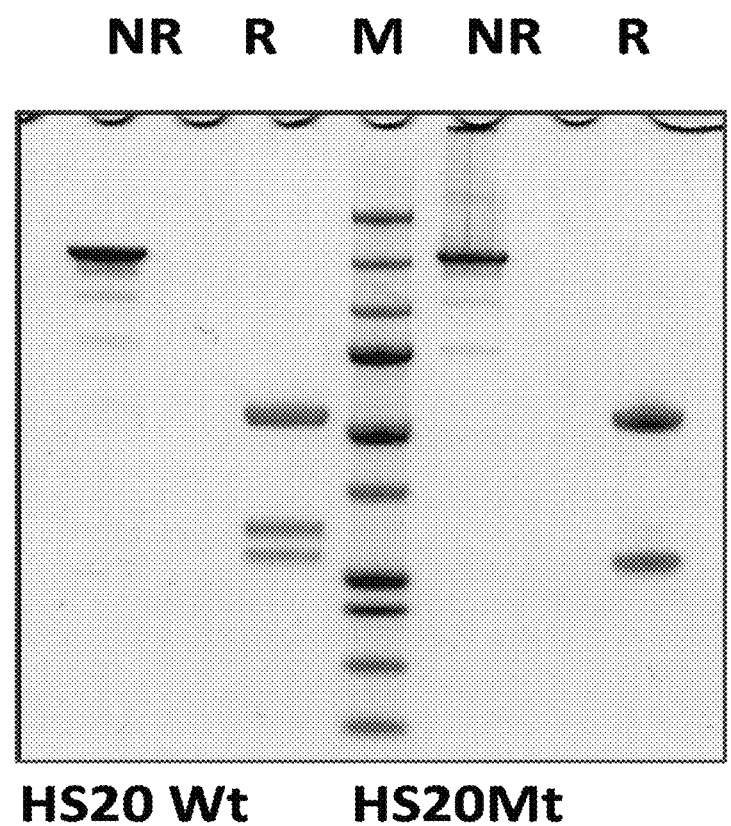
FIG. 16A shows SDS-PAGE of HS20 Wt and HS20 Mt under reducing (R) and non-reducing (NR) conditions. Five μg of purified protein was used for each sample. M=molecular weight marker.
Figure 16B:
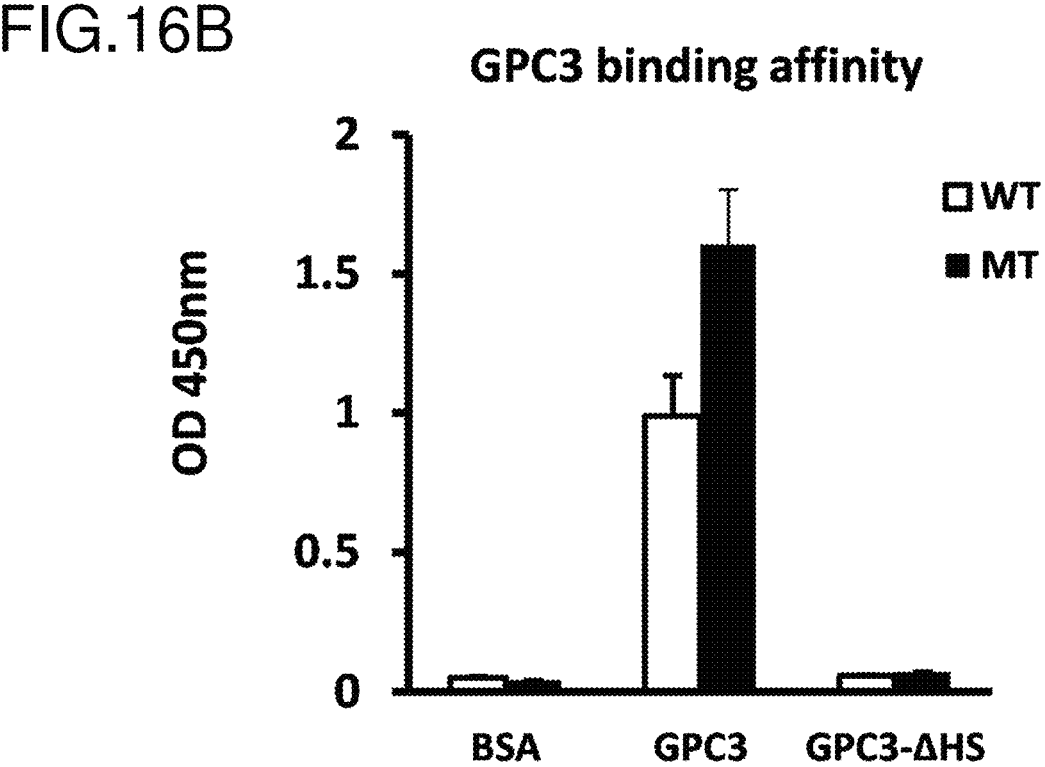
FIG. 16B is a graph showing the results of an ELISA to evaluate binding affinity of HS20 Wt and HS20 Mt for GPC3. The ELISA plate was coated with 5 μg/mL GPC3-hFc or GPC3(ΔHS)-hFc and incubated with 1 μg/mL HS20 Wt or HS20 Mt. Goat anti-human kappa chain-HRP was used as the secondary antibody at a dilution of 1:5000.
Figure 16C:
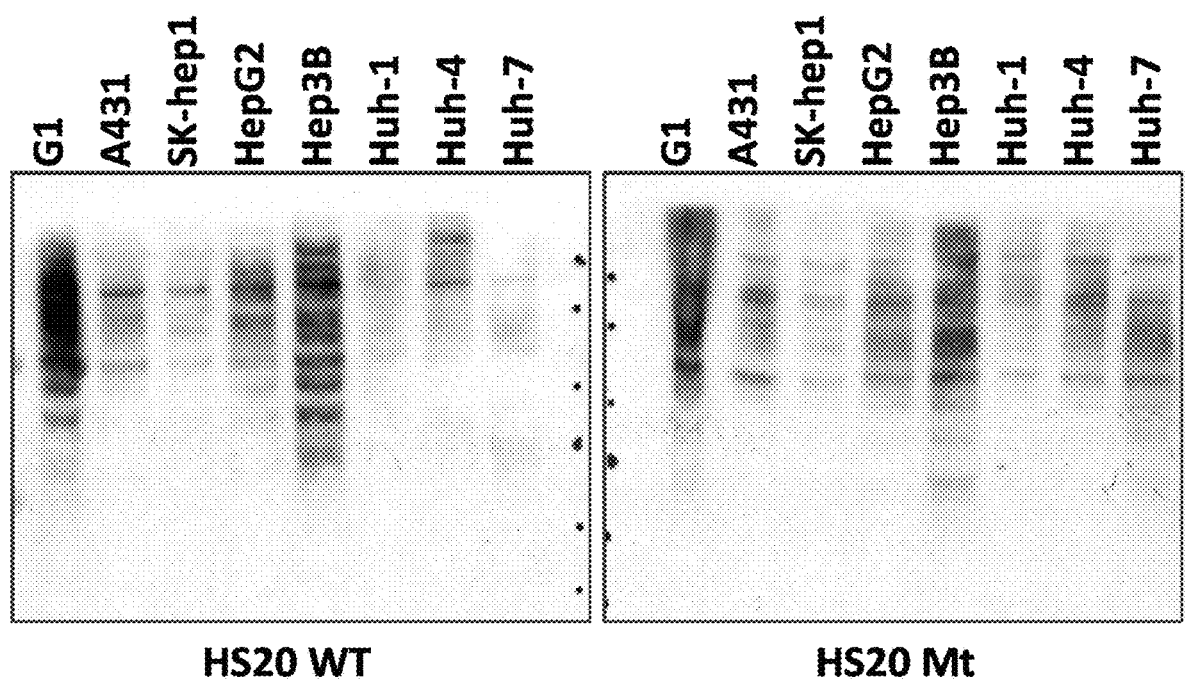
FIG. 16C is a Western blot showing binding of HS20 Wt or HS20 Mt to extracts of a variety of cell lines (30 μg of total protein for each sample). Five μg/ml of HS20 Wt or HS20 Mt was used as the primary antibody and goat anti-human kappa chain-HRP was used as the secondary antibody at a dilution of 1:5000.

To remove the N-glycosylation site, an asparagine (N) residue in CDR2 of the VL domain was changed to an alanine (A) residue (FIG. 15C). The modified version of HS20 is referred to as "HS20 Mt." The mutated form of HS20 does not exhibit altered binding specificity or affinity to the heparan sulfate chains on GPC3 (FIGS. 16A-16C).

The nucleotide and amino acid sequences of the modified HS20 VL domain are set forth in the sequence listing as SEQ ID NOs: 28 and 29, respectively.

Example 4: HS20 Inhibits HCC Tumor Growth In Vivo

Figure 17A:
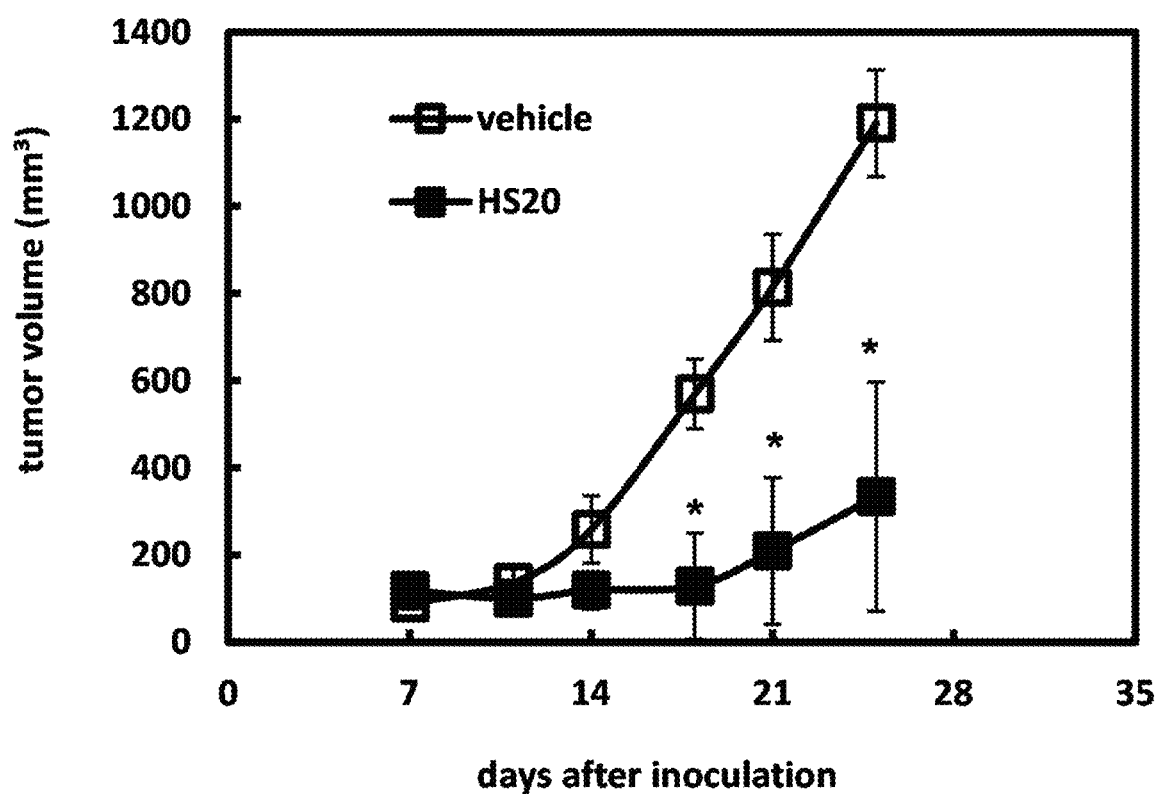
FIGS. 17A-17C are a series of figures showing that HS20 inhibits tumor growth in an HCC xenograft mouse model.
Figure 17B:
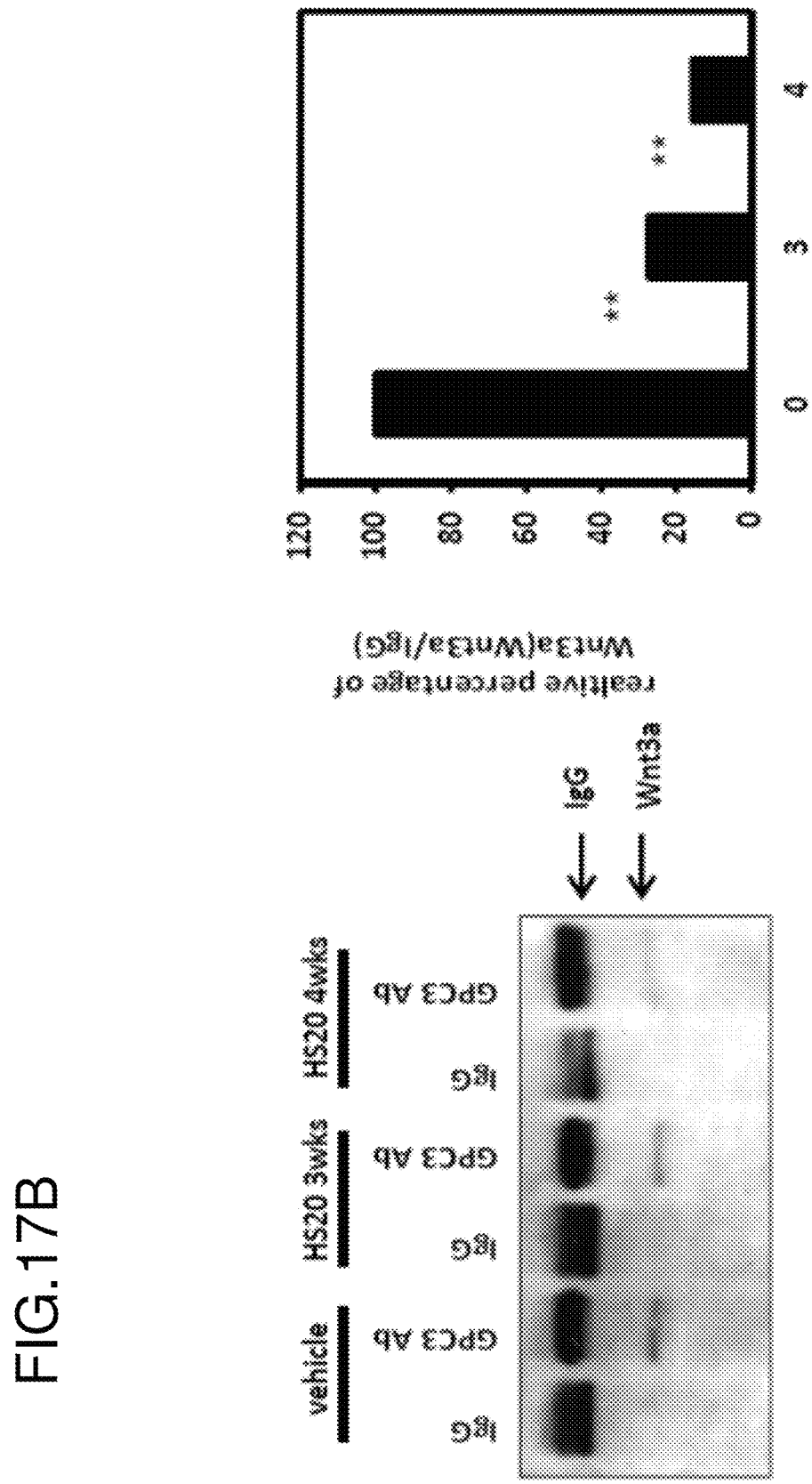
Figure 17C:
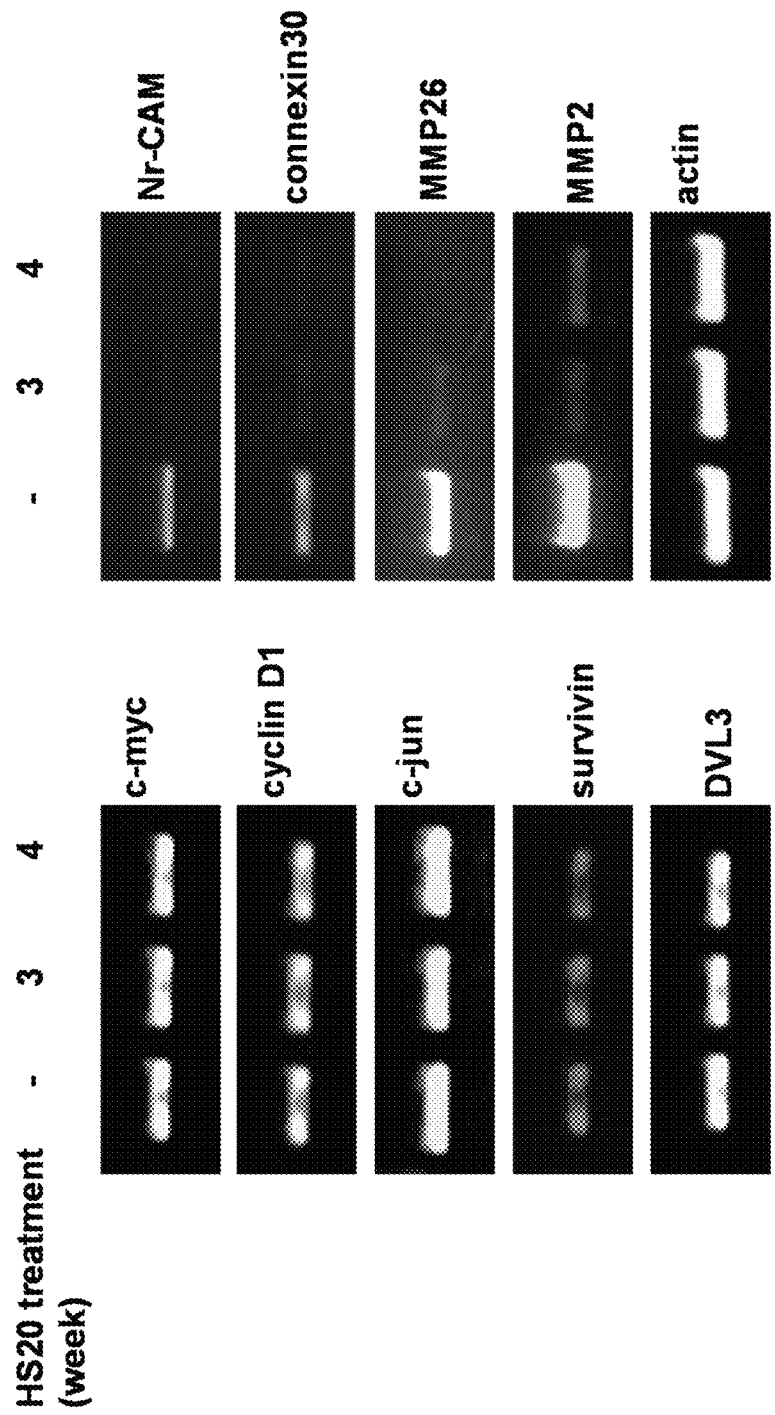

To evaluate the HS20 human antibody as a therapeutic antibody candidate, a HCC xenograft model was established in nude mice and the anti-tumor activity of the HS20 human antibody was tested. The study described in this example used the mutated form of HS20 (SEQ ID NOs: 28-31), which lacks the N-glycosylation site. HepG2 cells were inoculated into nude mice subcutaneously. As shown in FIG. 17A, the HS20 antibody inhibits tumor growth significantly. Using the xenograft tumor tissues, it was shown that the interaction of GPC3 and Wnt3a was significantly decreased after HS20 treatment. After treating the mice for three weeks, the interaction was blocked by 70% and even further for four weeks treatment (FIG. 17B). Downstream genes of Wnt signaling were also detected by RT-PCR. Several genes related to cell migration and metastasis, like Nr-CAM, Connexin30, MMP2 and MPP26 decreased significantly. However, those genes involved in cell proliferation did not change (FIG. 17C). These data were consistent with what was found using the in vitro cell models, and suggested that the HS20 human antibody was able to inhibit HCC tumor growth by blocking the interaction of GPC3 and Wnt3a via Wnt signaling.

Example 5: The HN3 Human Antibody Inhibits HCC Tumor Growth In Vivo

Figure 18A:
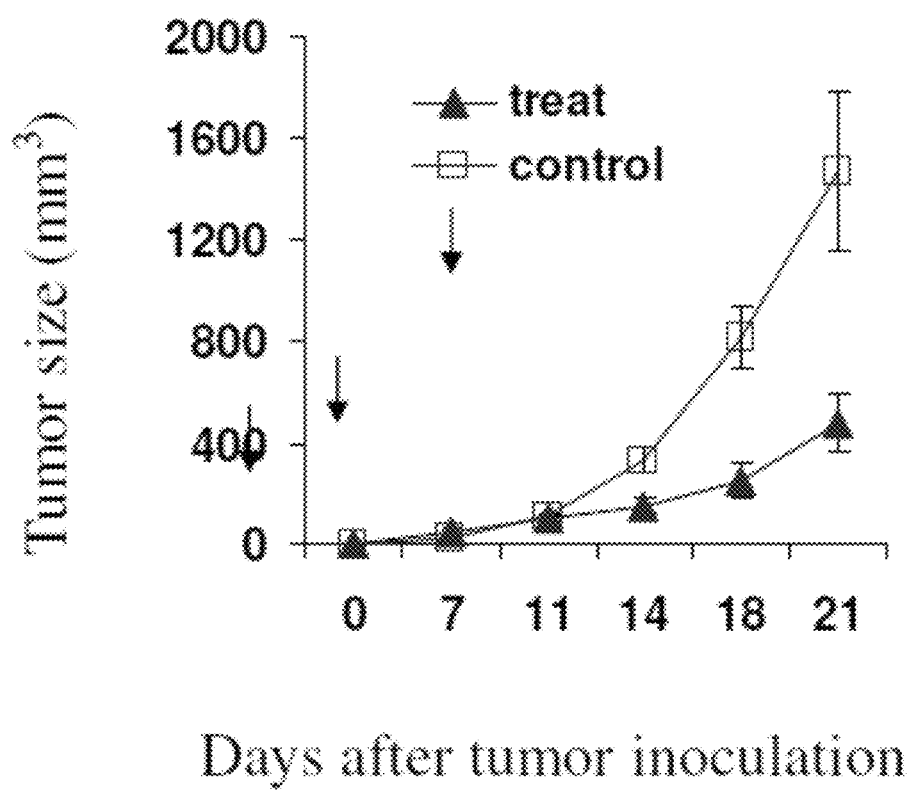

To investigate whether the HN3 human antibody can be used as a cancer therapeutic candidate, the in vivo efficacy of HN3 was investigated in mice. Huh7 cells were subcutaneously inoculated into nude mice. After the tumor size reached about 100 mm$^3$, the mice were treated by intravenous injection of HN3 at dose of 60 mg/kg, twice a week. The tumor size was measured and compared with the control group. HN3 treatment significantly inhibited HCC tumor growth in mice (FIG. 18A).

To confirm whether yap signaling also plays a role in HN3-treated HCC tumors in vivo, yap signaling changes were compared in HN3-treated and untreated HCC tumors from mice (FIG. 18B). Yap was inactivated because of the increase of phosphorylated yap in HN3-treated tumors. Consistent with in vitro data, the yap target gene, protein expression of cyclin D1 was also decreased. These observations further supported that yap signaling may mediate the inhibition of HCC cell proliferation by the HN3 human mAb.

Example 6: A Recombinant Immunotoxin Targeting Glypican-3 in Hepatocellular Carcinoma This example describes the generation of an antibody toxin fusion protein targeting GPC3 on HCC cells. The heavy chain variable region (VH) of HN3 was linked to PE38, a modified form of *Pseudomonas* exotoxin.

Generation of HN3(VH)-PE38 Immunotoxin

Figure 19A:
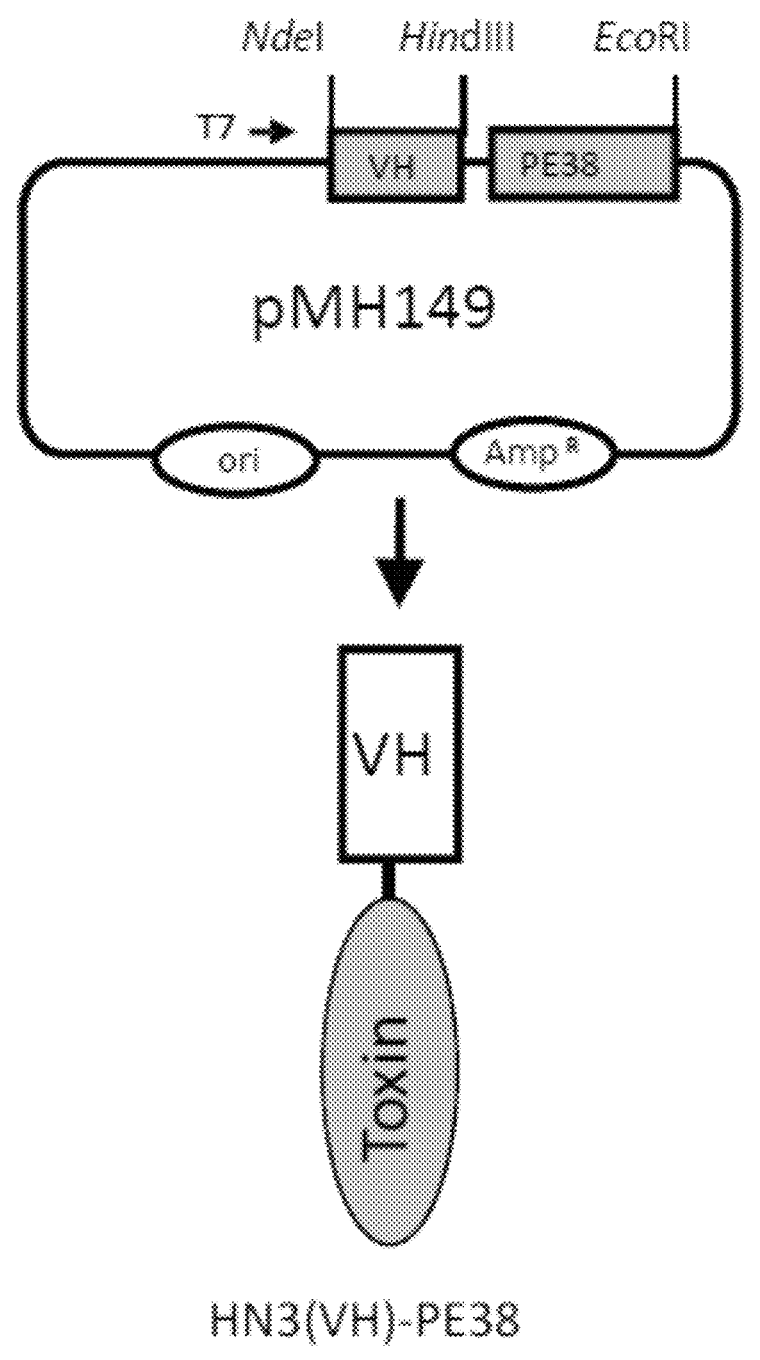
Figure 19B:
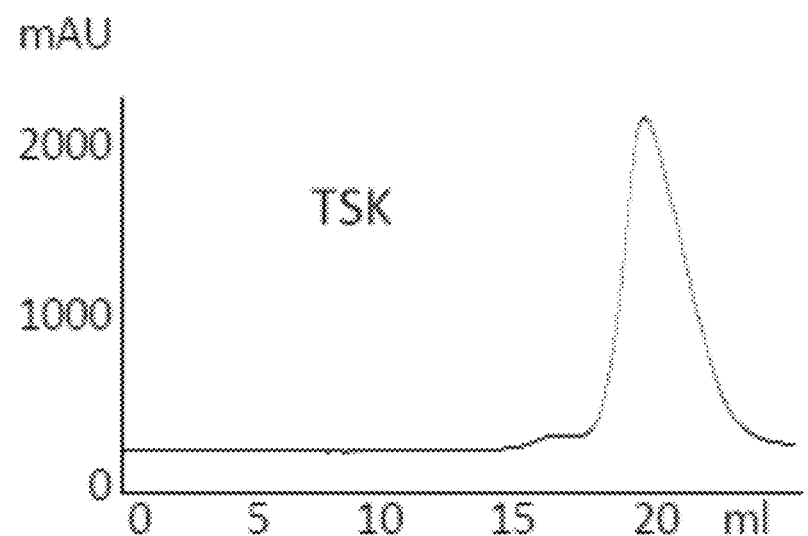
FIG. 19B is a graph showing that the HN3(VH)-PE38 immunotoxin protein eluted from a mono-Q column was run over a TSK gel filtration size-exclusion column.
Figure 19C:
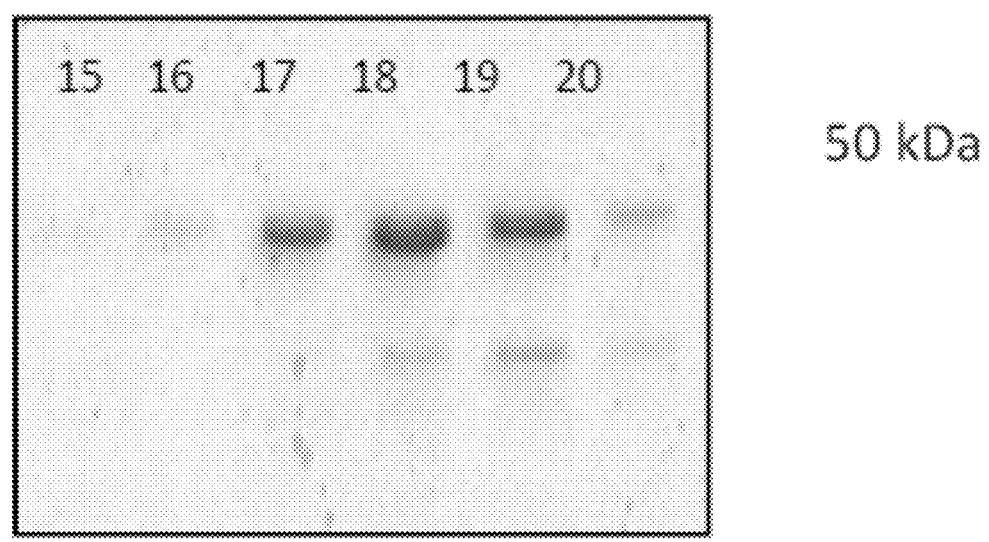
FIG. 19C shows SDS-PAGE analysis. Fractions of the HN3(VH)-PE38 immunotoxin collected from a TSK column were loaded on the gel.

To investigate the potential of HN3 as a novel antibody therapeutic for cancer therapy, the HN3 VH domain was converted into an anti-GPC3 immunotoxin. As shown in FIG. 19, the HN3 VH was fused to PE38 (SEQ ID NO: 27), a truncated form of *Pseudomonas* exotoxin.

The HN3 immunotoxin was prepared by cloning the nucleotide sequence of the single domain (VH) HN3 antibody and the nucleotide sequence of the *Pseudomonas* exotoxin 38 (PE38) into the pRB98 vector. The nucleotide and amino acid sequences of a portion of the immunotoxin that includes HN3, vector sequence (underlined) and the N-terminal portion of PE38 are shown below.

```
HN3-PE38 DNA Sequence
                                       (SEQ ID NO: 28)
CAGGTGCAGCTGGTGCAGTCTGGGGGAGGCTTGGTACAGCCTGGAGGGTC

CCTGAGACTCTCCTGTGCAGCCTCTTATTTCGATTTCGATTCTTATGAAA

TGAGCTGGGTCCGCCAGGCTCCAGGGAAGGGCCTAGAGTGGATTGGGAGT

ATCTATCATAGTGGGAGCACCTACTACAACCCGTCCCTCAAGAGTCGAGT

CACCATCTCCAGAGACAATTCCAAGAACACGCTGTATCTGCAAATGAACA

CCCTGAGAGCCGAGGACACAGCCACGTATTACTGTGCGAGAGTAAATATG

GACCGATTTGACTACTGGGGCCAGGGAACCCTGGTCACCGTCTCCTCAAG

TGCGGCCAAAGCTTCCGGAGGTCCCGAGGGCGGCAGCCTGGCCGCGCTGA

CCGCGCACCAGGCTTGCCACCTGCCGCTGGAGACTTTCACCCGTCATCGC

CAGCCGCGCGGCTGGGAACAACTGGAGCAGTGCGGCTATCCGGTGCAGCG

GCTGGTCGCCCTCTACCTGGCGGCGCGGCTGTCGTGGAACCAGGTCGACC

AGGTGATCCGCAACGCCCTGGCCAGCCCCGGCAGCGGCGGCGACCTGGGC

GAAGCGATCCGCGAGCAGCCGGAGCAAGCCCGTCTGGCCCTGACCCTGGC

CGCCGCCGAGAGCGAGCGCTTCGTCCGGCAGGGCACCGGCAACGACGAGG

CCGGCGCGGCCAACGGCCCGGCGGACAGCGGCGACGCC
Nucleotides 1-351 = HN3 DNA sequence
Nucleotides 352-378 (underlined) = vector sequence
Nucleotides 379-738 = partial PE38 sequence HN3-PE38 Protein Sequence
                                       (SEQ ID NO: 29)
QVQLVQSGGGLVQPGGSLRLSCAASYFDFDSYEMSWVRQAPGKGLEWIGS

IYHSGSTYYNPSLKSRVTISRDNSKNTLYLQMNTLRAEDTATYYCARVNM

DRFDYWGQGTLVTVSSSAAKASGGPEGGSLAALTAHQACHLPLETFTRHR

QPRGWEQLEQCGYPVQRLVALYLAARLSWNQVDQVIRNALASPGSGGDLG

EAIREQPEQARLALTLAAAESERFVRQGTGNDEAGAANGPADSGDAP
Residues 1-117 = HN3 sequence
Residues 118-126 (underlined) = derived from the
vector sequence
Residues 127-246 = partial PE38 sequence
```

The purity of the immunotoxin was above 90%, and the correct molecular weight (53 kDa) was confirmed by SDS-PAGE. The immunotoxin was expressed in *Escherichia coli*, refolded in vitro, and purified to ~95% purity with a high yield of >15%. To evaluate potential aggregation of the immunotoxin, the purified protein was run on a TSK size exclusion column (FIG. 19B). A distinct peak was found, indicating that the purified HN3(VH)-PE38 molecules as monomers were correctly folded.

Cytotoxicity of HN3(VH)-PE38 Immunotoxin Against HCC Cell Lines

Figure 20:
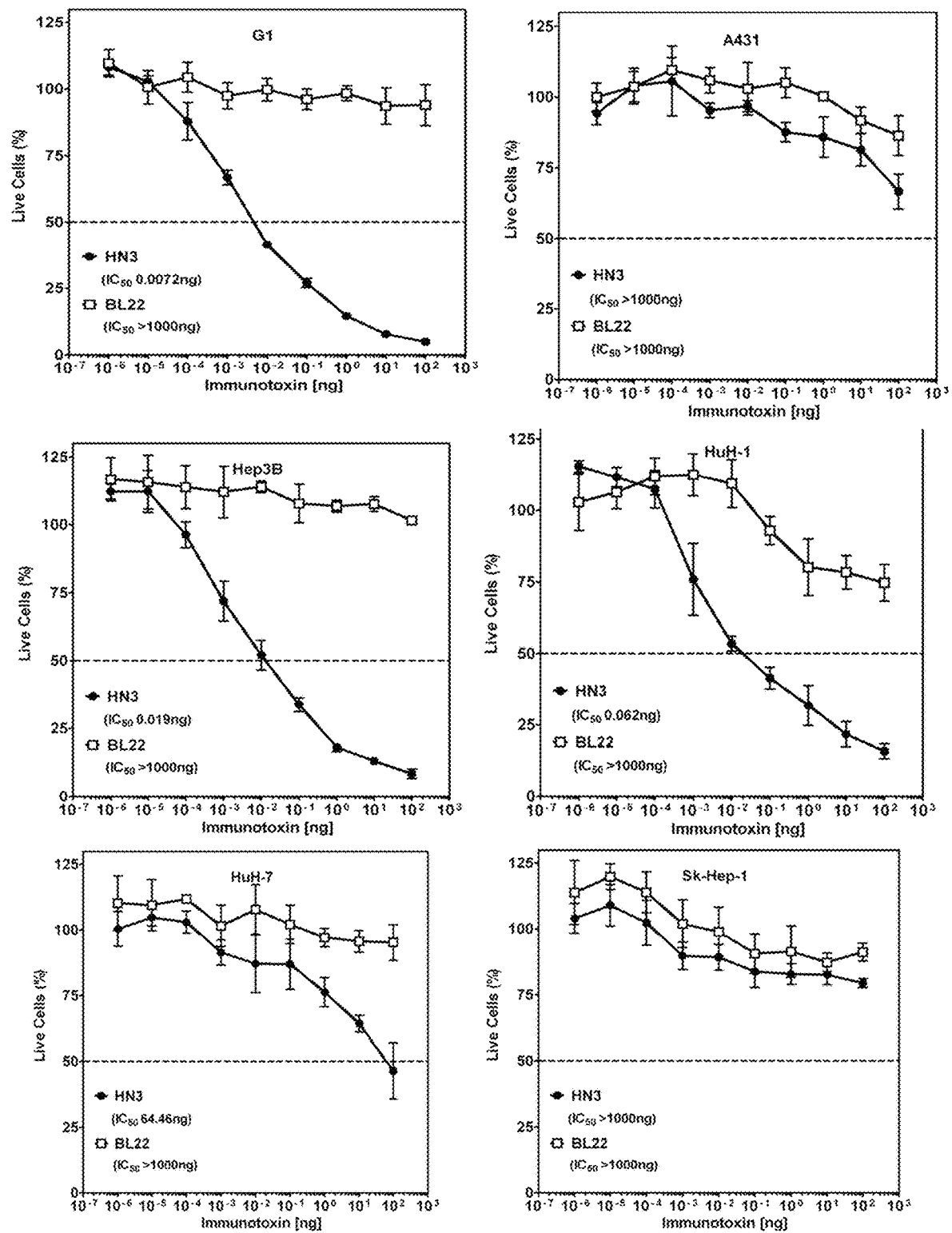
FIG. 20 is a series of graphs showing inhibition of cell proliferation on HCC cell lines by the HN3(VH)-PE38 immunotoxin. Cancer cells incubated with various concentrations of the anti-GPC3 immunotoxins containing HN3 (VH)-PE38 or BL22 for 72 hr. Cell proliferation was determined by a WST assay. The dashed line indicates 50% inhibition of cell proliferation, which is the toxin concentration that reduced cell viability by 50% compared with the cells that were not treated with the toxin. BL22: an immunotoxin specific for CD22 used as a nonspecific control.

To assess the cell killing of GPC3-expressing cancer cells by the HN3(VH)-PE38 immunotoxin, the inhibition of cell proliferation was examined on a panel of six HCC cell lines (Hep3B, Huh-1, HepG2, Huh-4, Huh-7 and SK-Hep-1) by WST assay (FIG. 20 and Table 4). The HN3(VH)-PE38 immunotoxin had very high and specific cytotoxic activity against the G1 cell line with forced expression of GPC3 ($IC_{50}$=0.01 ng/ml or 0.2 pM), but had no activity on the human A431 epidermoid carcinoma cell line with no GPC3 expression. In Hep3B and Huh-1, the three HCC cell lines with the highest GPC3 expression on the cell surface (>$10^4$ sites/cell), HN3(VH)-PE38 was very active with $IC_{50}$ of 0.02 ng/mL or 0.4 pM for Hep3B ($3.5 \times 10^4$ sites per cell), $IC_{50}$ of 0.06 ng/ml or 1.2 pM for Huh-1 ($1 \times 10^4$ sites per cell) and $IC_{50}$ of 64 ng/mL or 1.3 nM for Huh-7 ($1.2 \times 10^4$ sites/cell). In the HepG2 cell line with low GPC3 expression ($2.5 \times 10^3$ sites/cell), lower but significant cytotoxic activity ($IC_{50}$=549 ng/mL or 10 nM) was observed. The HN3(VH)-PE38 can't kill the Huh-4 and SK-Hep-1 cell lines because the data (flow cytometry, RT-PCR and Western blot) show that these two lines do not express GPC3. A recent study indicated that SK-HEP-1 was not a HCC cell line because it did not have properties of hepatocytes and was endothelial in origin. The cytotoxic activity of HN3(VH)-PE38 was similar or better than the immunotoxins SS1P and BL22 currently being evaluated in clinical trials for the treatment of other human cancers such as mesothelioma, pancreatic cancer and B-cell leukemias. BL22, the control immunotoxin targeting CD22-expressing leukemias, was not cytotoxic to all the HCC cell lines tested.

TABLE 4

Cytotoxicity of the HN3(VH)-PE38 immunotoxin and GPC3 expression in HCC cell lines

| Cell line | Tumor type | GPC3 sites/cell | HN3(VH)-PE38 (ng/mL) | BL22 (ng/mL) |
| --- | --- | --- | --- | --- |
| A431 | Epidermoid carcinoma | Negative* | >1000 | >1000 |
| G1 | Forced expression of GPC3 in A431 | $3.4 \times 10^5$ | 0.01 | >1000 |
| Hep3B | HCC | $3.5 \times 10^4$ | 0.02 | >1000 |
| Huh-1 | HCC | $1 \times 10^4$ | 0.06 | >1000 |
| Huh-7 | HCC | $1.2 \times 10^4$ | 64 | >1000 |
| HepG2 | HCC | $2.5 \times 10^3$ | 549 | >1000 |
| Huh-4 | HCC | $2 \times 10^3$ | >1000 | >1000 |
| SK-Hep-1 | Endothelial origin (formerly HCC) | Negative* | >1000 | >1000 |

*Negativity was also confirmed by RT-PCR and Western blot

Cytotoxicity was measured by cell proliferation assays (WST-8). Briefly, cells were seeded at $5 \times 10^4$/well in 96-well plate 12 h before the assay. Immunotoxins were added to the plate, and cells were incubated at 37° C. for 48-72 h and the cell viability measured with WST-8. Each assay was done in triplicate. $IC_{50}$ (mean values expressed in ng/ml) is the toxin concentration that reduced cell viability by 50% compared with the cells that were not treated with the toxin. The results are represented as means±SD of triplicate determinations, and assays were repeated two or three times. The number of GPC3 sites per cell was measured by flow cytometry using an anti-GPC3 mouse monoclonal antibody and BD Quantibrite PE beads.

Intravenous HN3(VH)-PE38 Immunotoxin Inhibits Tumor Growth

Figure 21:
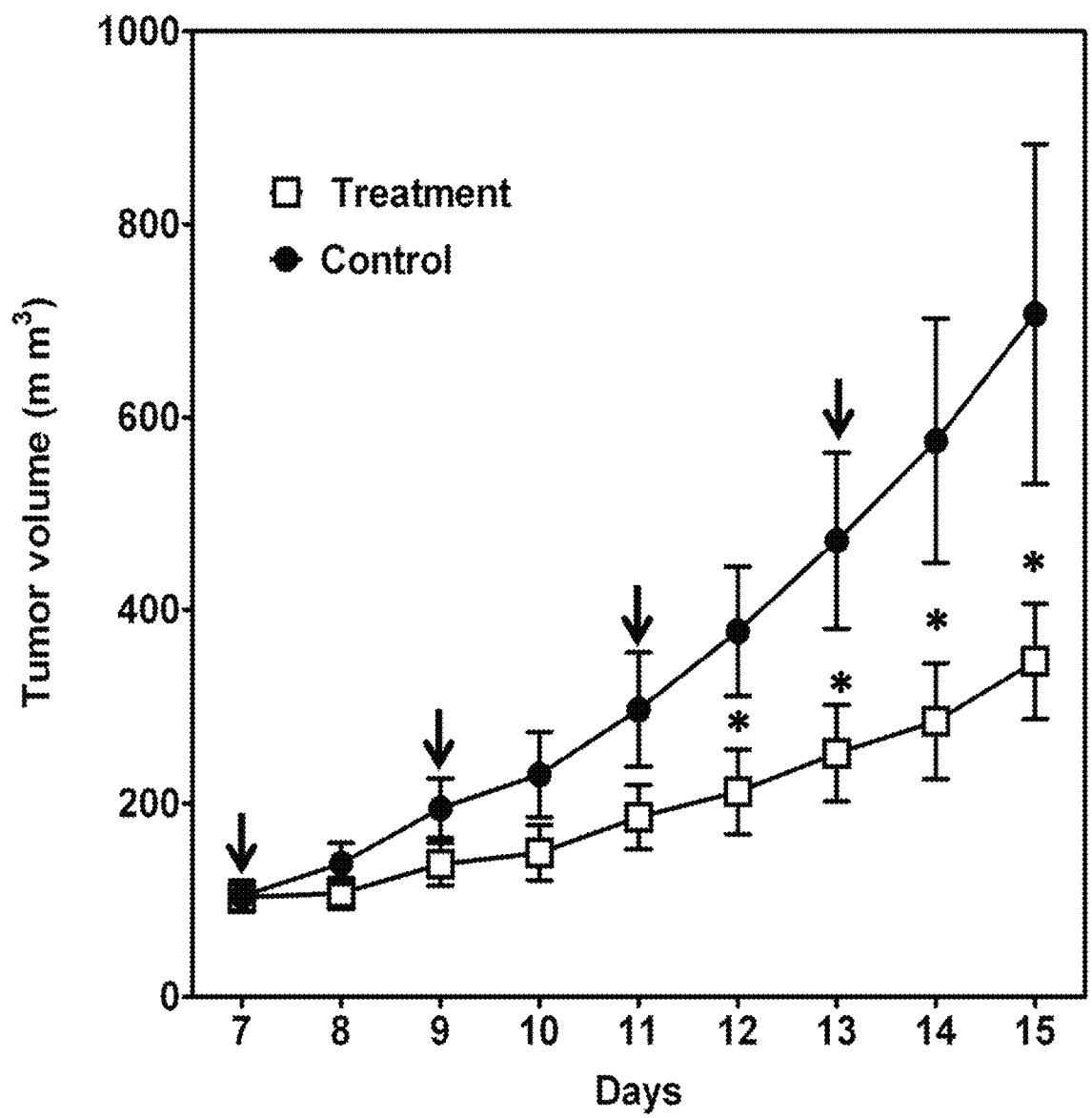
FIG. 21 is a graph showing anti-tumor activity of the HN3(VH)-PE38 immunotoxin in the xenograft model. BALB/c nu/nu mice were s.c. inoculated with 3 million G1 cells. When tumors reached an average volume of 100 mm³, mice were administered 0.4 mg/kg of the HN3(VH)-PE38 immunotoxin every other day for about one week. Arrow: HN3(VH)-PE38 injection. Quantification of tumor size by formula V=ab²/2 (where a and b represent tumor length and width, respectively). *$p<0.05$.

To explore HN3(VH)-PE38 as a potential cancer therapeutic, it was examined whether the anti-GPC3 immunotoxin caused tumor growth inhibition in tumor xenografts in mice. The G1 cell line was used as a cell model to establish a tumor xenograft model in nude mice (FIG. 21). The number of GPC3 sites in the G1 line is comparable to that of HCC cells endogenously expressing GPC3 and their implantation in mice consistently results in aggressive tumor growth. When tumors reached an average volume of 100 $mm^3$ on day 7, mice were administered 0.4 mg/kg of the HN3(VH)-PE38 every other day for one week. The administration of HN3(VH)-PE38 significantly inhibited the growth of the tumor in mice since day 12 (after three injections of the immunotoxin). Therefore, the HN3(VH)-PE38 as a single agent exhibited strong antitumor activity against GPC3-expressing tumor xenografts in vivo.

Taken together, these results show that an immunotoxin targeting cell surface-associated GPC3 proteins in HCC has been successfully generated. The HN3(VH)-PE38 immunotoxin is cytotoxic against GPC3-expressing HCC cell lines but is not cytotoxic to target-negative cells. Furthermore, the immunotoxin exhibited significant tumor growth inhibition of subcutaneously transplanted GPC3-expressing tumor xenografts in nude mice, suggesting that the new immunotoxin holds potential as a therapeutic candidate for liver cancer therapy.

Example 7: GPC3-Specific Monoclonal Antibodies for Detecting Cancer in a Subject or Confirming the Diagnosis of Cancer in a Subject This example describes the use of human monoclonal antibodies that bind GPC3 or HS chains on GPC3 for the detection of cancer in a subject. This example further describes the use of these antibodies to confirm the diagnosis of cancer in a subject.

A sample (such as a biopsy) is obtained from the patient diagnosed with, or suspected of having a GPC3-positive cancer (i.e., a cancer that expresses or overexpresses GPC3, such as HCC, melanoma, lung cancer, or ovarian cancer). A sample taken from a patient that does not have cancer can be used as a control. Immunohistochemistry (IHC) is performed to detect the presence of GPC3-expressing cells in the sample. IHC are well known in the art. For example, a GPC3-specific antibody conjugated to a fluorescent marker can be used to directly detect GPC3. An increase in fluorescence intensity of the patient sample, relative to the control sample, detects the presence of GPC3-expressing cells in the sample. Detection of GPC3-positive cells in the sample indicates the patient has a GPC3-positive cancer, or confirms diagnosis of cancer in the subject.

Example 8: GPC3-Specific Monoclonal Antibodies for the Treatment of Cancer

This example describes the use of GPC3-specific human monoclonal antibodies for the treatment of cancers that express or overexpress GPC3, such as HCC, melanoma, lung cancer, or ovarian cancer. Patients diagnosed with a GPC3-positive cancer can be treated according to standard procedures in the art.

In this example, patients diagnosed with a GPC3-positive cancer are administered an immunoconjugate comprising a GPC3-specific human monoclonal antibody linked to *Pseudomonas* exotoxin (PE). Preparation of PE immunoconjugates is described in Example 6 and has been previously described in the art (see, for example, U.S. Pat. No. 7,081,518 and U.S. Patent Application Publication No. 2005/0214304). In some patients, the immunoconjugate is administered by intravenous bolus injection every other day for a total of three to six doses. In other patients, the immunoconjugate is administered by continuous intravenous infusion over the course of ten days. The dose of immunoconjugate administered to a patient varies depending on the weight and gender of the patient, and mode and time course of administration. Following treatment, patients are evaluated for cancer progression (including tumor growth and metastasis) and other clinical signs of illness.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated human variable heavy (VH) domain monoclonal antibody that binds glypican-3 (GPC3), comprising the complementarity determining region (CDR) 1, CDR2 and CDR3 sequences of SEQ ID NO: 2.

2. The human VH single-domain monoclonal antibody of claim 1, comprising residues 31-35, 50-65 and 96-105 of SEQ ID NO: 2.

3. The human VH single-domain monoclonal antibody of claim 1, wherein the antibody is labelled.

4. The human VH single-domain monoclonal antibody of claim 3, wherein the label is a fluorescence, enzymatic or radioactive label.

5. A composition comprising a therapeutically effective amount of the human VH single-domain antibody of claim 1 in a pharmaceutically acceptable carrier.

6. An isolated immunoconjugate comprising the human VH single-domain monoclonal antibody of claim 1 and an effector molecule.

7. The isolated immunoconjugate of claim 6, wherein the effector molecule is a toxin.

8. The isolated immunoconjugate of claim 7, wherein the toxin is *Pseudomonas* exotoxin or a variant thereof.

9. The isolated immunoconjugate of claim 8, wherein the toxin is PE38 comprising the amino acid sequence of SEQ ID NO: 27.

10. A composition comprising a therapeutically effective amount of the isolated immunoconjugate of claim 6 in a pharmaceutically acceptable carrier.

11. A method of treating a subject with cancer, comprising selecting a subject with a cancer that expresses GPC3 and administering to the subject a therapeutically effective amount of the composition of claim 5, thereby treating the cancer in the subject.

12. The method of claim 11, wherein the cancer is a liver cancer, melanoma, lung cancer or ovarian cancer.

13. The method of claim 12, wherein the liver cancer is hepatocellular carcinoma (HCC) or hepatoblastoma.

14. A method of inhibiting tumor growth or metastasis, comprising selecting a subject with a cancer that expresses GPC3 and administering to the subject a therapeutically effective amount of the composition of claim 5, thereby inhibiting tumor growth or metastasis.

15. The method of claim 14, wherein the cancer is a liver cancer, melanoma, lung cancer or ovarian cancer.

16. The method of claim 15, wherein the liver cancer is HCC or hepatoblastoma.

17. A method of detecting GPC3 in a tissue sample, comprising:
    contacting the sample with the human VH single-domain monoclonal antibody of claim 1; and
    detecting binding of the antibody to the sample,
    wherein an increase in binding of the antibody to the sample as compared to binding of the antibody to a control sample detects GPC3 in the tissue sample.

18. An isolated nucleic acid molecule encoding the human VH single-domain monoclonal antibody of claim 1.

19. The isolated nucleic acid molecule of claim 18, operably linked to a promoter.

20. An expression vector comprising the isolated nucleic acid molecule of claim 19.

21. An isolated host cell transformed with the expression vector of claim 20.

\* \* \* \* \*